(12) United States Patent
Elbaz et al.

(10) Patent No.: US 11,504,571 B2
(45) Date of Patent: *Nov. 22, 2022

(54) DEVICE AND METHODS FOR TUNING A SKELETAL MUSCLE

(71) Applicant: APOS MEDICAL ASSETS LTD., Tel Aviv (IL)

(72) Inventors: Avi Elbaz, Dimona (IL); Amit Mor, Rehovot (IL)

(73) Assignee: APOS MEDICAL ASSETS LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/994,603

(22) Filed: Aug. 16, 2020

(65) Prior Publication Data
US 2020/0376323 A1   Dec. 3, 2020

Related U.S. Application Data

(63) Continuation of application No. 16/025,100, filed on Jul. 2, 2018, now Pat. No. 10,744,368, which is a
(Continued)

(51) Int. Cl.
*A63B 21/00* (2006.01)
*A43B 5/00* (2022.01)
(Continued)

(52) U.S. Cl.
CPC ............ *A63B 21/4015* (2015.10); *A43B 5/00* (2013.01); *A43B 7/00* (2013.01); *A43B 7/144* (2013.01);
(Continued)

(58) Field of Classification Search
CPC .............. A63B 21/4015; A63B 26/003; A63B 21/0004; A63B 22/18; A63B 23/04;
(Continued)

(56) References Cited

U.S. PATENT DOCUMENTS

| 1,021,142 A | 3/1912 | Freeman |
| 1,061,353 A | 5/1913 | Block |

(Continued)

FOREIGN PATENT DOCUMENTS

| DE | 1907894 | 1/1965 |
| DE | 29701013 | 3/1997 |

(Continued)

OTHER PUBLICATIONS

Cerruto et al. "The Effect of Ankle Inclination in Upright Position on the Electromyigraphic Activity of Pelvic Floor Muscles in Women With Stress Urinary Incontinence". European Urology Supplements, vol. 6, No. 2. (Mar. 2007), pp. 102.
(Continued)

*Primary Examiner* — Garrett K Atkinson
(74) *Attorney, Agent, or Firm* — The Roy Gross Law Firm, LLC; Roy Gross

(57) ABSTRACT

A method of differentially tuning a lower limb muscle in a human in need thereof is provided. The method includes placement of at least two calibrated, differential disturbances or protuberances under the human's feet thereby tuning a lower limb muscle.

8 Claims, 19 Drawing Sheets

Related U.S. Application Data continuation of application No. 13/807,948, filed as application No. PCT/IL2011/000512 on Jun. 27, 2011, now Pat. No. 10,010,743.

(60) Provisional application No. 61/360,940, filed on Jul. 2, 2010.

(51) Int. Cl.

| | | |
|---|---|---|
| A43B 7/00 | (2006.01) | |
| A43B 13/14 | (2006.01) | |
| A61F 3/00 | (2006.01) | |
| A43B 7/144 | (2022.01) | |
| A43B 7/1445 | (2022.01) | |
| A63B 22/18 | (2006.01) | |
| A63B 23/04 | (2006.01) | |
| A63B 26/00 | (2006.01) | |

(52) U.S. Cl.
CPC .......... *A43B 7/1445* (2013.01); *A43B 13/143* (2013.01); *A43B 13/145* (2013.01); *A61F 3/00* (2013.01); *A63B 21/0004* (2013.01); *A63B 22/18* (2013.01); *A63B 23/04* (2013.01); *A63B 26/003* (2013.01); *A63B 2022/185* (2013.01); *A63B 2208/0204* (2013.01); *A63B 2225/09* (2013.01); *A63B 2225/093* (2013.01)

(58) Field of Classification Search
CPC ...... A63B 2022/185; A63B 2208/0204; A63B 2225/09; A63B 2225/093; A43B 7/144; A43B 7/1445; A43B 13/145; A43B 5/00; A43B 7/00; A43B 13/143; A61F 3/00
See application file for complete search history.

(56) References Cited

U.S. PATENT DOCUMENTS

| | | |
|---|---|---|
| 1,529,421 A | 3/1925 | Dowdell |
| 1,736,576 A | 11/1929 | Cable |
| 2,133,302 A | 10/1938 | Mccormick |
| 2,303,744 A | 12/1942 | Jacobs |
| 2,311,925 A | 2/1943 | Boos |
| 2,518,033 A | 8/1950 | Lucas |
| 3,082,549 A | 3/1963 | Dolceamore |
| 3,402,485 A | 9/1968 | Mcmorrow |
| 3,526,976 A | 9/1970 | Jacobs |
| 3,552,043 A | 1/1971 | Moffa |
| 3,782,011 A | 1/1974 | Fisher |
| 3,859,736 A | 1/1975 | Hill et al. |
| 3,867,929 A | 2/1975 | Joyner et al. |
| 3,916,538 A | 4/1975 | Loseff |
| 3,940,128 A | 2/1976 | Ragone |
| 4,030,213 A | 6/1977 | Daswick |
| 4,071,963 A | 2/1978 | Fukuoka |
| 4,241,523 A | 12/1980 | Daswick |
| 4,262,434 A | 4/1981 | Michelotti |
| 4,348,821 A | 9/1982 | Daswick |
| RE31,173 E | 3/1983 | Daswick |
| 4,586,706 A | 5/1986 | Chen |
| 4,629,181 A | 12/1986 | Krive |
| 4,653,748 A | 3/1987 | Seel et al. |
| 4,660,548 A | 4/1987 | Bucher |
| 4,660,826 A | 4/1987 | Lee |
| 4,739,986 A | 4/1988 | Kucharik et al. |
| 4,821,432 A | 4/1989 | Reiber |
| 4,841,648 A | 6/1989 | Shaffer et al. |
| 4,892,090 A | 1/1990 | Kaeser |
| 5,014,706 A | 5/1991 | Philipp |
| 5,018,511 A | 5/1991 | Yokoi |
| 5,035,418 A | 7/1991 | Harabayashi |
| 5,103,806 A | 4/1992 | McLeod et al. |
| 5,113,850 A | 5/1992 | Larremore et al. |
| 5,188,578 A | 2/1993 | Voigt |
| 5,203,321 A | 4/1993 | Donovan et al. |
| 5,211,160 A | 5/1993 | Talish et al. |
| 5,337,494 A | 8/1994 | Ricker |
| 5,400,528 A | 3/1995 | Skinner et al. |
| D357,347 S | 4/1995 | Leick |
| 5,518,476 A | 5/1996 | McLeon |
| 5,520,612 A | 5/1996 | Winder et al. |
| 5,533,282 A | 7/1996 | Kataoka et al. |
| 5,549,527 A | 8/1996 | Yu |
| 5,584,787 A | 12/1996 | Guidry |
| 5,603,334 A | 2/1997 | Sharp |
| 5,643,145 A | 7/1997 | Lo et al. |
| 5,647,145 A * | 7/1997 | Russell ................ A43B 3/0052 36/25 R |
| 5,682,690 A | 11/1997 | Chang |
| 5,685,807 A | 11/1997 | Tong et al. |
| 5,730,705 A | 3/1998 | Talish et al. |
| D394,343 S | 5/1998 | Marshall et al. |
| D394,541 S | 5/1998 | Burgess |
| 5,848,954 A | 12/1998 | Steams et al. |
| 5,860,228 A | 1/1999 | Bathum |
| 5,897,464 A | 4/1999 | Mcleod |
| 5,902,214 A | 5/1999 | Makikawa et al. |
| D412,393 S | 8/1999 | Aquino |
| D416,672 S | 11/1999 | Curley, Jr. et al. |
| 6,019,712 A | 2/2000 | Duncan |
| 6,063,046 A | 5/2000 | Allum |
| 6,102,832 A | 8/2000 | Tani |
| 6,126,577 A | 10/2000 | Chang |
| 6,170,173 B1 | 1/2001 | Caston |
| 6,176,817 B1 | 1/2001 | Carey et al. |
| D439,733 S | 4/2001 | Savoie |
| 6,277,057 B1 | 8/2001 | Hayden |
| 6,283,897 B1 | 9/2001 | Patton |
| D448,920 S | 10/2001 | Montross et al. |
| 6,311,416 B1 | 11/2001 | Cohen |
| 6,315,786 B1 | 11/2001 | Smuckler et al. |
| 6,349,487 B1 | 2/2002 | Mice |
| 6,393,735 B1 | 5/2002 | Berggren |
| 6,432,070 B1 | 8/2002 | Talish et al. |
| 6,464,654 B1 | 10/2002 | Montgomery et al. |
| 6,511,404 B2 | 1/2003 | Tu |
| 6,519,873 B1 | 2/2003 | Buttigieg et al. |
| 6,551,225 B1 | 4/2003 | Romero |
| 6,652,432 B2 | 11/2003 | Smith |
| D482,851 S | 12/2003 | McClaskie |
| 6,692,419 B2 | 2/2004 | Chen |
| D488,915 S | 4/2004 | Girbaud et al. |
| 6,742,289 B2 | 6/2004 | Celmo |
| 6,792,703 B2 | 9/2004 | Cohen |
| 6,793,609 B1 | 9/2004 | Fan |
| 6,796,056 B2 | 9/2004 | Swigart |
| 6,811,523 B1 | 11/2004 | Timmer |
| 6,880,267 B2 | 4/2005 | Smaldone et al. |
| 6,979,287 B2 | 12/2005 | Elbaz et al. |
| 7,004,895 B2 | 2/2006 | Perry et al. |
| 7,081,070 B1 | 7/2006 | Washington et al. |
| 7,101,330 B2 | 9/2006 | Elbaz et al. |
| 7,165,343 B2 | 1/2007 | Fukui |
| 7,287,340 B2 | 10/2007 | Talbott |
| 7,373,740 B2 | 5/2008 | Lo |
| 7,500,324 B1 | 3/2009 | Power et al. |
| 7,707,751 B2 * | 5/2010 | Avent .................. A61F 5/14 36/150 |
| D648,517 S | 11/2011 | Vestuti et al. |
| 3,079,159 A1 | 12/2011 | Rosa |
| 8,205,356 B2 | 6/2012 | Ellis |
| 8,758,207 B2 | 6/2014 | Elbaz et al. |
| 8,959,798 B2 | 2/2015 | Pfister |
| 2002/0026730 A1 | 3/2002 | Whatley |
| 2002/0038522 A1 | 4/2002 | Houser et al. |
| 2002/0092201 A1 | 7/2002 | Kraeuter et al. |
| 2002/0100190 A1 | 8/2002 | Pellerin |
| 2002/0139011 A1 * | 10/2002 | Kerrigan ................ A43B 7/22 36/144 |
| 2002/0166258 A1 | 11/2002 | Posa |
| 2003/0148865 A1 | 8/2003 | Handshoe |
| 2003/0153849 A1 | 8/2003 | Huckle et al. |
| 2003/0188458 A1 | 10/2003 | Kelly |

(56) References Cited

U.S. PATENT DOCUMENTS

| | | | |
|---|---|---|---|
| 2004/0033864 A1* | 2/2004 | Elbaz | A63B 26/003 482/51 |
| 2004/0033874 A1* | 2/2004 | Elbaz | A43B 5/18 482/148 |
| 2004/0053751 A1 | 3/2004 | Pizolato | |
| 2004/0082886 A1 | 4/2004 | Timpson | |
| 2005/0235526 A1 | 10/2005 | Kim | |
| 2006/0130372 A1 | 6/2006 | Auger et al. | |
| 2006/0196087 A1 | 9/2006 | Sellers et al. | |
| 2007/0051020 A1 | 3/2007 | Tajima et al. | |
| 2007/0079532 A1 | 4/2007 | Ramirez | |
| 2007/0193071 A1* | 8/2007 | Gilmore | A61F 5/14 36/174 |
| 2008/0134541 A1 | 6/2008 | Bar-Haim et al. | |
| 2008/0229611 A1* | 9/2008 | Chiodo | A43B 17/035 36/29 |
| 2008/0263898 A1 | 10/2008 | Gueh | |
| 2009/0113760 A1 | 5/2009 | Dominguez | |
| 2009/0172975 A1 | 7/2009 | Keough | |
| 2009/0199429 A1 | 8/2009 | Ellis | |
| 2010/0251565 A1 | 10/2010 | Litchfield et al. | |
| 2010/0325919 A1* | 12/2010 | Elbaz | A63B 26/003 36/103 |
| 2011/0047831 A1* | 3/2011 | Elbaz | A43B 7/00 36/136 |
| 2011/0072684 A1 | 3/2011 | Stubblefield | |
| 2011/0126422 A1 | 6/2011 | Vattes et al. | |
| 2012/0073166 A1 | 3/2012 | Bryla | |
| 2013/0116726 A1* | 5/2013 | Mor | A61H 39/04 606/204 |
| 2014/0109444 A1 | 4/2014 | Dumont | |

FOREIGN PATENT DOCUMENTS

| | | |
|---|---|---|
| DE | 29902731 | 3/2000 |
| DE | 10133863 | 2/2003 |
| EP | 925809 | 6/1999 |
| EP | 1038459 | 9/2000 |
| EP | 2462827 | 6/2012 |
| FR | 1128009 | 1/1957 |
| FR | 2820329 | 8/2002 |
| JP | S6111928 | 1/1986 |
| JP | 2000084035 | 3/2000 |
| JP | 2005536247 | 12/2005 |
| JP | 2007029700 | 2/2007 |
| JP | 2008264023 | 11/2008 |
| KR | 20030058556 | 7/2003 |
| NL | 8502659 | 4/1987 |
| WO | 9620651 | 7/1996 |
| WO | 9713422 | 4/1997 |
| WO | 0067846 | 11/2000 |
| WO | 0137693 | 5/2001 |
| WO | 0237995 | 5/2002 |
| WO | 03090868 | 11/2003 |
| WO | 2004016321 | 2/2004 |
| WO | 2004043185 | 5/2004 |
| WO | 2006005139 | 1/2006 |
| WO | 2011024162 | 3/2011 |
| WO | 2012001685 | 1/2012 |

OTHER PUBLICATIONS

The Gait Cycle as found at http://www.upstate.edu/cdb/grossanat/limbs6.shtml (2013).

Nieuwenhuijzen et al., Mechanically induced ankle inversion during human walking and jumping, Journal of Neuroscience Methods 117 (2002) 133-140 (8 pages).

Japanese Patent Office's office action, transmitted Feb. 24, 2015; 2 pages—Japanese and 2 pages—English translation.

International Search Report from the U.S. patent office in a counterpart PCT application—1 page, dated Nov. 23, 2011.

* cited by examiner

DEVICE AND METHODS FOR TUNING A SKELETAL MUSCLE

This application is a Continuation of U.S. patent application Ser. No. 16/025,100 filed Jul. 2, 2018, which is a continuation of Ser. No. 13/807,948 filed on Mar. 8, 2013, which is a national phase application of PCT Patent Application No. PCT/IL11/00512 having International filing date of Jun. 27, 2011, which claims the benefit of priority of U.S. Patent Application No. 61/360,940 filed on Jul. 2, 2010. The contents of the above applications are all incorporated by reference as if fully set forth herein in their entirety

FIELD OF INVENTION

This invention is directed to, inter alia, methods of differentially tuning a muscle in a subject in need thereof.

BACKGROUND OF THE INVENTION

Training protocols and sporting equipment that cause specific alterations in muscle activity during exercise may have important implications for training, rehabilitation after injury, and competitive performance.

Three types of muscle exist: skeletal, cardiac and smooth which have significant differences. All three types use the movement of actin against myosin to create contraction. In skeletal muscle, contraction is simulated by electrical impulses transmitted by the nerves, the motor nerves and motoneurons in particular. Cardiac and smooth muscle contractions are stimulated by internal pacemaker cells which regularly contract, and propagate contractions to other muscle cells they are in contact with. All skeletal muscle contractions are facilitated by the neurotransmitter acetylcholine.

Muscular activity accounts for much of the body's energy consumption. All muscle cells produce adenosine triphosphate (ATP) molecules which are used to power the movement of the myosin heads. Muscles conserve energy in the form of creatine phosphate which is generated from ATP and can regenerate ATP when needed with creatine kinase. Muscles also keep a storage form of glucose in the form of glycogen. Glycogen can be rapidly converted to glucose when energy is required for sustained, powerful contractions. Within the voluntary skeletal muscles, the glucose molecule can be metabolized anaerobically in a process called glycolysis which produces two ATP and two lactic acid molecules in the process (note that in aerobic conditions, lactate is not formed; instead pyruvate is formed and transmitted through the citric acid cycle).

SUMMARY OF THE INVENTION

In one embodiment, the present invention provides a method of tuning a lower limb skeletal muscle in a subject in need thereof comprising the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, wherein the balanced position is a position whereby the device provides a reduced inversion or a reduced eversion to the subject's foot during the stance phases; and (2) a muscle tuning position; and (c) fixing the posterior protuberance and the anterior protuberance to the support member.

In another embodiment, the present invention further provides a method of tuning a lower limb skeletal muscle in a subject suffering from lower limb muscle pathology and lower limb musculoskeletal pain, comprising the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, wherein the balanced position is a position whereby the device provides a reduced inversion or a reduced eversion to the subject's foot during the stance phases; (2) a minimal or reduced pain position; and (3) a muscle tuning position; and (c) fixing the posterior protuberance and the anterior protuberance to the support member.

In another embodiment, the present invention further provides a method of treating a subject suffering from a lower limb pathology comprising the step of tuning a lower limb skeletal muscle in the subject, wherein tuning a lower limb skeletal muscle comprises the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, wherein balanced position comprises a position whereby the device provides a reduced inversion or a reduced eversion to the subject's foot during the stance phases; and (2) a muscle tuning position; and (c) fixing the posterior protuberance and the anterior protuberance to the support member.

In another embodiment, the present invention further provides a method of treating a subject suffering from a lower limb pathology and lower musculoskeletal pain, comprising the step of tuning a lower limb skeletal muscle in the subject, wherein tuning a lower limb skeletal muscle comprises the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, the balanced position comprises a position whereby the device provides a reduced inversion or a reduced eversion to the subject's foot during the stance phases; (2) a minimal or reduced pain position; and (3) a muscle tuning position; and (c) fixing the posterior protuberance and the anterior protuberance to the support member.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Muscle Calibration

Figure 1:
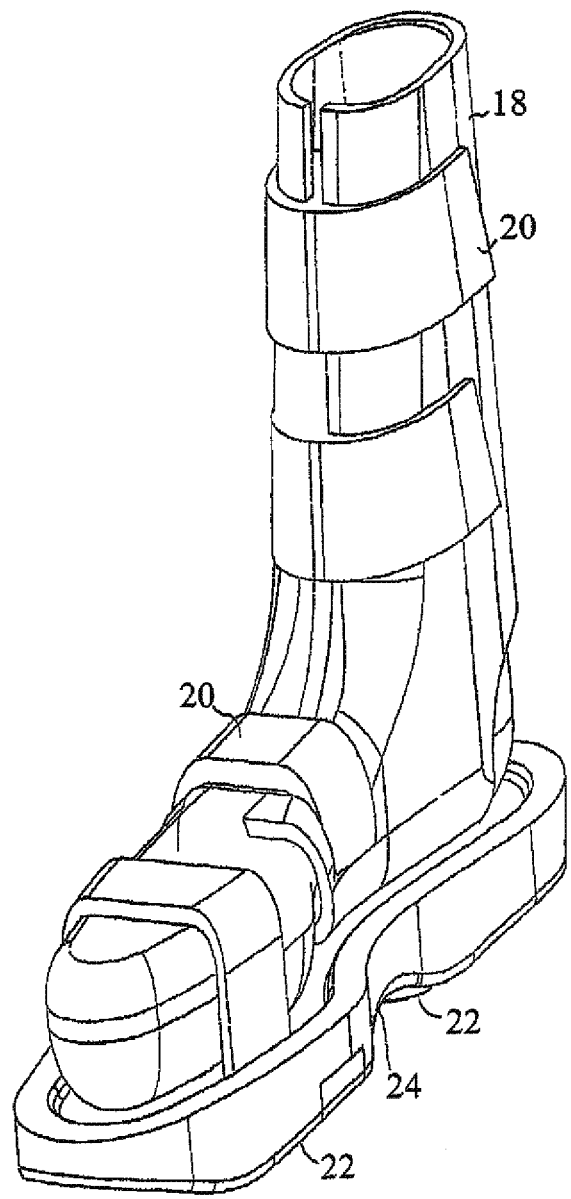
FIG. 1 is a simplified pictorial illustration of footwear constructed and operative in accordance with an embodiment of the present invention

This invention provides, in one embodiment, a method of tuning a lower limb skeletal muscle in a subject in need thereof comprising the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, the balanced position comprises a position whereby the device provides a reduced inversion or a reduced eversion to the subject's foot during the stance phases; and (2) a muscle tuning position; and (c) fixing the posterior protuberance and the anterior protuberance to the support member. In another embodiment, provided herein the use of a device comprising a foot securing mean, a support member operably attached to the securing mean, and a moveable anterior protuberance and a moveable posterior protuberance, wherein device calibration includes positioning or calibrating the protuberances to a position wherein the device provides (1) a reduced inversion or a reduced eversion to the subject's foot during the stance phases and (2) a muscle tuning position, for tuning a lower limb skeletal muscle. In another embodiment, provided herein the use of a device comprising a foot securing mean, a support member operably attached to the securing mean, and a moveable anterior protuberance and a moveable posterior protuberance, wherein device calibration includes positioning or calibrating the protuberances to a position wherein the device provides (1) a reduced inversion or a reduced eversion to the subject's foot during the stance phases; (2) reduced pain in a lower limb position; and (2) a muscle tuning position, for tuning a lower limb skeletal muscle. Each possibility represents a separate embodiment of the present invention.

In another embodiment, the methods disclosed herein are directed to muscle tuning which include tuning its activity (increased, reduced, or timed differently) by changing the center of pressure (COP) with which the foot contacts the ground. In another embodiment, changing the center of pressure (COP) with which the foot contacts the ground is executed through calibrating the device (footwear) of the invention. In another embodiment, COP is changed or altered via a perturbation induced by a protuberance as disclosed herein. In another embodiment, a device of the invention alters COP thus changing the movement pattern of a lower limb. In another embodiment, a change in movement pattern is dependent on a change in muscular activity in the lower limb. In another embodiment, a muscle can be differentially tuned with a device such as disclosed herein as a consequence of controlled change in movement pattern. In another embodiment, a change in movement must be controlled in order to prevent damage, injury, trauma, or a combination thereof to the subject using the device. In another embodiment, the methods of the invention provide a controlled change in movement pattern and concomitantly avoiding damage, injury, trauma, or a combination thereof (such as but not limited to: falls, damaging gait, damaging lower limb neuromuscular control or activity) to the subject using the device, thus efficiently enabling the differential tuning of lower limb muscles of interest. In another embodiment, COP is constantly changing due to a perturbation caused by a protuberance. Each possibility represents a separate embodiment of the present invention.

In another embodiment, the methods of the invention provide that the desired differential lower limb muscle tuning occurs in various activities the subject is performing, for example: walking, standing, cooking or getting up from a chair. Each possibility represents a separate embodiment of the present invention.

In another embodiment, the methods described herein comprise that changing the COP in a direction or to a position away from the anatomical location of the muscle, results in inducing an increase in the muscle's activity. In another embodiment, the methods described herein comprise that changing the COP in a direction or to a position which is closer to the anatomical position of the muscle, results in reducing the muscle's activity. Each possibility represents a separate embodiment of the present invention.

In another embodiment, the methods of the invention provide that a protuberance introducing a perturbation on which the subject needs to bear weight induces muscle tuning (i.e. its activity can be increased, reduced, or timed differently). In another embodiment, muscle tuning is not selective to a specific muscle or muscle group. In another embodiment, muscle tuning is specific to the muscles' former activity pattern. In another embodiment, the methods of the invention provide that a muscle which was relatively inactive (where it should have been active) or inhibited would increase its activity level in order to control the instability or perturbation caused by a protuberance. Each possibility represents a separate embodiment of the present invention.

In another embodiment, the methods of the invention provide that a muscle which was hyperactive (i.e. bracing or active for longer periods of time then it should be in a specific activity) would decrease its bracing. In another embodiment, the methods of the invention provide that a lower limb muscle reacts to a perturbation. In another embodiment, the methods of the invention provide that a lower limb muscle reacts to a perturbation thus decreasing its hyperactivity due to the perturbation. In another embodiment, the methods of the invention provide that a lower limb muscle reacts to a perturbation induced into daily activities such as walking, getting up from a chair, cooking etc. Each possibility represents a separate embodiment of the present invention.

In another embodiment, the methods of the invention provide that a muscle is tuned (i.e. its activity can be increased, reduced, or timed differently) by changing the height of the fore-foot in relation to the hind-foot. In another embodiment, the methods of the invention provide that increasing the height of the fore-foot in relation to the height of the hind-foot, thus creating a dorsi-flexed alignment, activates the muscles which are posterior to the midline (in the frontal plane) of the lower limb. In another embodiment, the methods of the invention provide that increasing the height of the hind-foot in relation to the height of the fore-foot, thus creating a plantar-flexed alignment, activates the muscles which are anterior to the midline (in the frontal plane) of the lower limb. Each possibility represents a separate embodiment of the present invention.

In another embodiment, the methods of the invention provide that a muscle is tuned (i.e. its activity can be increased, reduced, or timed differently) by attaching differential weight to a specified location under the foot. In another embodiment, various activities require lifting the leg off the ground while supporting and balancing the entire body weight on the other leg (the stance leg). In another embodiment, increasing the weight of the leg being lifted off the ground demands greater muscular activity from the muscles responsible for lifting the leg off the ground. In another embodiment, location specific, differential, increased weight of the lifted leg increases muscular activity differentially—the muscles responsible for supporting and stabilizing the weight of the body on the stance leg. Each possibility represents a separate embodiment of the present invention.

In another embodiment, tuning a lower limb skeletal muscle comprises improving motor skills, fitness, muscle and bone strength, joint function, or any combination thereof. In another embodiment, tuning a lower limb skeletal muscle comprises inducement of certain muscle fiber utilization over another. In another embodiment, tuning a lower limb skeletal muscle comprises aerobic exercise comprising long, low levels of exertion in which the muscles are used at well below their maximal contraction strength for long periods of time. In another embodiment, tuning a lower limb skeletal muscle comprises using the device for short bursts of intense activity. In another embodiment, tuning a lower limb skeletal muscle comprises induction of neovascularization within the muscle. Each possibility represents a separate embodiment of the present invention.

Target Populations Who are in Need of Muscle Tuning

In another embodiment, a subject in need thereof is a subject suffering from a neuromuscular pathology. In another embodiment, a subject in need thereof is a subject suffering from muscle weakness, muscle spasticity, myoclonus, myalgia, or any combination thereof. In another embodiment, a subject in need thereof is a subject suffering from myopathy or dystrophy. In another embodiment, a subject in need thereof is a subject suffering from spasticity or paralysis. In another embodiment, a subject in need thereof is a subject suffering from a neurological disorder and has problems with movement (such as but not limited to: stroke, Parkinson's disease). Each possibility represents a separate embodiment of the present invention.

In another embodiment, a subject in need thereof is a subject suffering from muscle atrophy. In another embodiment, a subject in need thereof is a subject suffering from cachexia. In another embodiment, a subject in need thereof is a subject suffering from AIDS. In another embodiment, a subject in need thereof is a subject suffering from a congestive heart disease. Each possibility represents a separate embodiment of the present invention.

In another embodiment, a subject in need thereof is a subject suffering from a lower limb joint disease or a lower limb musculoskeletal pathology. In another embodiment, a subject suffering from a lower limb joint disease or a lower limb musculoskeletal pathology experiences changes in muscular activity either due to pain inhibition, disrupted proprioception, changes in joint alignment, disuse, weakness, neural damage, compensations, etc. In another embodiment, changes in muscular activity increase the load or strain or effort of the damaged structures thus perpetuating the lower limb joint disease or a lower limb musculoskeletal pathology. In another embodiment, a subject in need thereof is a subject at risk of developing a lower limb joint disease or a lower limb musculoskeletal pathology. Each possibility represents a separate embodiment of the present invention.

In another embodiment, a subject at risk of developing a lower limb joint disease or a lower limb musculoskeletal pathology is a subject exposed to repetitive strain injuries due to imbalanced muscular activities (for example repeated squatting). In another embodiment, a subject at risk of developing a lower limb joint disease or a lower limb musculoskeletal pathology is a subject which is exposed to prolonged physical stresses due to loads he or she sustains. In another embodiment, such loads are for example prolonged standing with relatively little movement (for example cooks, surgeons). Each possibility represents a separate embodiment of the present invention.

In another embodiment, a subject at risk of developing a lower limb joint disease or a lower limb musculoskeletal pathology is a subject is an elderly subject. In another embodiment, an elderly subject is susceptible of developing lower limb musculoskeletal pathologies due to age related muscle weakening (such as but not limited to: sarcopenia). In another embodiment, an elderly subject is susceptible of developing lower limb musculoskeletal pathologies due to decrease in muscle recruitment speed (time to contraction). In another embodiment, muscular age related effects increase the loads on the joint, thus instigating a lower limb joint pathology accompanied by pain, in turn; pain actively changes the muscular activity and increases the load on the joint. Each possibility represents a separate embodiment of the present invention.

In another embodiment, a subject in need thereof is a subject in need of enhancing his or hers performance such as elite or recreational athletes. In another embodiment, a subject in need of enhancing his or hers performance benefits by tuning/improving the muscles ability to contract quickly in response to an external stimulus (the starting gun, a ball). In another embodiment, a subject in need thereof is an athlete benefiting from improved muscular activity during the warm up before game or a race. In another embodiment, an athlete benefits from decreasing the recovery time of the muscles following a hard training session, a game or a race. Each possibility represents a separate embodiment of the present invention.

Muscle Tuning

In another embodiment, muscle tuning according to the methods described herein is performed by calibration of an anterior protuberance a posterior protuberance or both.

In another embodiment, a dorsi-flexor muscle is tuned according to the methods of the invention. In another embodiment, the dorsi-flexors comprise: tibialis anterior, extensor digitorum longus, and extensor hallucis longus. In another embodiment, a plantar flexor muscle is tuned according to the methods of the invention. In another embodiment, the plantar-flexors comprise: gastrocnemius, soleus, plantaris, flexor hallucis longus, flexor digitorum longus, and tibialis posterior. In another embodiment, an evertor muscle is tuned according to the methods of the invention. In another embodiment, the evertors comprise: peroneus longus, peroneus brevis and peroneus tertius. In another embodiment, an invertor muscle is tuned according to the methods of the invention. In another embodiment, the invertors comprise: tibialis anterior, tibialis posterior, extensor digitorum longus, extensor hallucis longus and flexor hallucis longus. Each possibility represents a separate embodiment of the present invention.

In another embodiment, an activity of a dorsi-flexor is increased by calibrating the posterior protuberance to a posterior position from the neutral position which is the balanced position (the position wherein the device provides a reduced inversion or a reduced eversion to the subject's foot). In another embodiment, an activity of a dorsi-flexor is increased by calibrating the posterior protuberance to 2 mm-25 mm posteriorly from the balanced position. In another embodiment, an activity of a dorsi-flexor is increased by calibrating the posterior protuberance to 5 mm-15 mm posteriorly from the balanced position. In another embodiment, an activity of a dorsi-flexor is increased according to the methods described herein by 3-50%. In another embodiment, an activity of a dorsi-flexor is increased according to the methods described herein by 10-30%. In another embodiment, an activity of a dorsi-flexor is increased as much as 30%. Each possibility represents a separate embodiment of the present invention.

In another embodiment, an activity of a dorsi-flexor is increased during initial contact of the posterior protuberance with a ground surface. In another embodiment, an activity of a dorsi-flexor is increased during initial contact. In another embodiment, an activity of a dorsi-flexor is increased during loading response. In another embodiment, an activity of a dorsi-flexor is increased during swing. In another embodiment, the anterior protuberance is calibrated to a higher position (1-12 mm) than the posterior protuberance so that the ankle is in a dorsi-flexed position and muscle activity is increasing during swing by as much as 25%. In another embodiment, an activity of a dorsi-flexor is increased during swing by inserting weighted spacer between the outsole and the base of the anterior protuberance (resulting in increase of weight at the base of the anterior protuberance) thus in response the dorsi-flexors increase their power generation in order to accomplish foot clearance Each possibility represents a separate embodiment of the present invention.

In another embodiment, an activity of a dorsi-flexor is increased by heightening the posterior protuberance. In another embodiment, an activity of a dorsi-flexor is increased by heightening the posterior protuberance by 0.5 mm-15 mm. In another embodiment, an activity of a dorsi-flexor is increased by heightening the posterior protuberance by 1 mm-10 mm. In another embodiment, an activity of a dorsi-flexor is increased by heightening the posterior protuberance by 2 mm-8 mm. In another embodiment, heightening the posterior protuberance results in a posterior protuberance which is 0.5 mm-15 mm higher than the anterior protuberance. In another embodiment, heightening the posterior protuberance results in that the ankle is in a plantar-flexed position. In another embodiment, heightening the posterior protuberance results in dorsi-flexor muscle activity increase. In another embodiment, heightening the posterior protuberance results in 5-50% dorsi-flexor muscle activity increase. In another embodiment, heightening the posterior protuberance results in 10-30% dorsi-flexor muscle activity increase. In another embodiment, heightening the posterior protuberance results in as much as 35% dorsi-flexor muscle activity increase. Each possibility represents a separate embodiment of the present invention.

In another embodiment, an activity of a plantar flexor is increased by calibrating the posterior protuberance to an anterior position from the neutral position which is the balanced position (the position wherein the device provides a reduced inversion or a reduced eversion to the subject's foot). In another embodiment, an activity of a plantar flexor is increased by calibrating the posterior protuberance to 2 mm-25 mm anteriorly from the balanced position. In another embodiment, an activity of a plantar flexor is increased by calibrating the posterior protuberance to 5 mm-15 mm anteriorly from the balanced position. In another embodiment, an activity of a plantar flexor is increased according to the methods described herein by 3-40%. In another embodiment, an activity of a plantar flexor is increased according to the methods described herein by 5-25%. In another embodiment, an activity of a dorsi-flexor is increased as much as 25%. Each possibility represents a separate embodiment of the present invention.

In another embodiment, an activity of a plantar flexor is increased by calibrating the anterior protuberance to an anterior position from the neutral position which is the balanced position (the position wherein the device provides a reduced inversion or a reduced eversion to the subject's foot). In another embodiment, an activity of a plantar flexor is increased by calibrating the anterior protuberance to 0.5 mm-15 mm anteriorly from the balanced position. In another embodiment, an activity of a plantar flexor is increased by calibrating the anterior protuberance to 1 mm-10 mm anteriorly from the balanced position. In another embodiment, an activity of a plantar flexor is increased by calibrating the anterior protuberance to 2 mm-8 mm anteriorly from the balanced position. In another embodiment, an activity of a plantar flexor is increased according to the methods described herein by 3-40%. In another embodiment, an activity of a plantar flexor is increased according to the methods described herein by 5-25%. In another embodiment, an activity of a plantar-flexor is increased as much as 25%. Each possibility represents a separate embodiment of the present invention.

In another embodiment, an activity of a plantar-flexor is increased by heightening (raising) the anterior protuberance. In another embodiment, an activity of a plantar-flexor is increased by heightening the anterior protuberance by 0.5 mm-12 mm. In another embodiment, an activity of a plantar-flexor is increased by heightening the anterior protuberance by 1 mm-8 mm. In another embodiment, an activity of a plantar-flexor is increased by heightening the anterior protuberance by 1 mm-5 mm. In another embodiment, heightening the anterior protuberance results in an anterior protuberance which is 0.5 mm-12 mm higher than the posterior protuberance. In another embodiment, heightening the anterior protuberance results in that the ankle is in a dorsi-flexed position. In another embodiment, heightening the anterior protuberance results in muscle activity increase. In another embodiment, heightening the anterior protuberance results in 5-50% plantar-flexor muscle activity increase. In another embodiment, heightening the anterior protuberance results in 10-30% plantar-flexor muscle activity increase. In another embodiment, heightening the anterior protuberance results in as much as 35% plantar-flexor muscle activity increase. Each possibility represents a separate embodiment of the present invention.

In another embodiment, an activity of an ankle evertor is increased by calibrating the posterior protuberance medially from the neutral position which is the balanced position (the position wherein the device provides a reduced inversion or a reduced eversion to the subject's foot). In another embodiment, an activity of an ankle evertor is increased by calibrating the posterior protuberance to 0.5 mm-15 mm medially from the balanced position. In another embodiment, an activity of an ankle evertor is increased by calibrating the posterior protuberance to 1 mm-10 mm medially from the balanced position. In another embodiment, an activity of an ankle evertor is increased by calibrating the posterior protuberance to 3 mm-8 mm medially from the balanced position. In another embodiment, an activity of an ankle evertor is increased according to the methods described herein by 3-40%. In another embodiment, an activity of an ankle evertor is increased according to the methods described herein by 5-25%. In another embodiment, an activity of an ankle evertor is increased as much as 25%. Each possibility represents a separate embodiment of the present invention.

In another embodiment, an activity of an ankle evertor is increased by calibrating the anterior protuberance medially from the neutral position which is the balanced position (the position wherein the device provides a reduced inversion or a reduced eversion to the subject's foot). In another embodiment, an activity of an ankle evertor is increased by calibrating the anterior protuberance to 0.5 mm-25 mm medially from the balanced position. In another embodiment, an activity of an ankle evertor is increased by calibrating the anterior protuberance to 1 mm-10 mm medially from the balanced position. In another embodiment, an activity of an ankle evertor is increased by calibrating the anterior protuberance to 3 mm-8 mm medially from the balanced position. In another embodiment, an activity of an ankle evertor is increased according to the methods described herein by 3-40%. In another embodiment, an activity of an ankle evertor is increased according to the methods described herein by 5-25%. In another embodiment, an activity of an ankle evertor is increased as much as 25%. Each possibility represents a separate embodiment of the present invention.

In another embodiment, an activity of an ankle evertor is decreased by calibrating the posterior protuberance laterally from the neutral position which is the balanced position (the position wherein the device provides a reduced inversion or a reduced eversion to the subject's foot). In another embodiment, an activity of an ankle evertor is decreased by calibrating the posterior protuberance to 0.5 mm-25 mm laterally from the balanced position. In another embodiment, an activity of an ankle evertor is decreased by calibrating the posterior protuberance to 1 mm-10 mm laterally from the balanced position. In another embodiment, an activity of an ankle evertor is decreased by calibrating the posterior protuberance to 3 mm-8 mm laterally from the balanced position. In another embodiment, an activity of an ankle evertor is decreased according to the methods described herein by 3-40%. In another embodiment, an activity of an ankle evertor is decreased according to the methods described herein by 5-25%. In another embodiment, an activity of an ankle evertor is decreased as much as 25%. Each possibility represents a separate embodiment of the present invention.

In another embodiment, an activity of an ankle evertor is decreased by calibrating the anterior protuberance laterally from the neutral position which is the balanced position (the position wherein the device provides a reduced inversion or a reduced eversion to the subject's foot). In another embodiment, an activity of an ankle evertor is decreased by calibrating the anterior protuberance to 0.5 mm-25 mm laterally from the balanced position. In another embodiment, an activity of an ankle evertor is decreased by calibrating the anterior protuberance to 1 mm-10 mm laterally from the balanced position. In another embodiment, an activity of an ankle evertor is decreased by calibrating the anterior protuberance to 3 mm-8 mm laterally from the balanced position. In another embodiment, an activity of an ankle evertor is decreased according to the methods described herein by 3-40%. In another embodiment, an activity of an ankle evertor is decreased according to the methods described herein by 5-25%. In another embodiment, an activity of an ankle evertor is decreased as much as 25%. Each possibility represents a separate embodiment of the present invention.

In another embodiment, an activity of an ankle dorsi-flexor is decreased by calibrating the posterior protuberance anteriorly from the neutral position which is the balanced position (the position wherein the device provides a reduced inversion or a reduced eversion to the subject's foot). In another embodiment, an activity of an ankle dorsi-flexor is decreased by calibrating the posterior protuberance to 0.5 mm-20 mm anteriorly from the balanced position. In another embodiment, an activity of an ankle dorsi-flexor is decreased by calibrating the posterior protuberance to 1 mm-15 mm anteriorly from the balanced position. In another embodiment, an activity of an ankle dorsi-flexor is decreased by calibrating the posterior protuberance to 3 mm-8 mm anteriorly from the balanced position. In another embodiment, an activity of an ankle dorsi-flexor is decreased according to the methods described herein by 3-40%. In another embodiment, an activity of an ankle dorsi-flexor is decreased according to the methods described herein by 5-25%. In another embodiment, an activity of an ankle dorsi-flexor is decreased as much as 25%. Each possibility represents a separate embodiment of the present invention.

In another embodiment, an activity of an ankle dorsi-flexor is decreased by heightening the anterior protuberance from the neutral position which is the balanced position (the position wherein the device provides a reduced inversion or a reduced eversion to the subject's foot). In another embodiment, an activity of an ankle dorsi-flexor is decreased during stance by heightening the anterior protuberance from the neutral position which is the balanced position. In another embodiment, an activity of an ankle dorsi-flexor is decreased by increasing the height of the anterior protuberance by 0.5-10 mm. In another embodiment, an activity of an ankle dorsi-flexor is decreased by increasing the height of the anterior protuberance by 1-6 mm. In another embodiment, an activity of an ankle dorsi-flexor is decreased by increasing the height of the anterior protuberance by 1-4. In another embodiment, an activity of an ankle dorsi-flexor is decreased according to the methods described herein by 3-40%. In another embodiment, an activity of an ankle dorsi-flexor is decreased according to the methods described herein by 5-25%. In another embodiment, an activity of an ankle dorsi-flexor is decreased as much as 25%. Each possibility represents a separate embodiment of the present invention.

In another embodiment, an activity of an ankle plantar-flexor is decreased by calibrating the posterior protuberance posteriorly from the neutral position which is the balanced position (the position wherein the device provides a reduced inversion or a reduced eversion to the subject's foot). In another embodiment, an activity of an ankle plantar-flexor is decreased by calibrating the posterior protuberance to 0.5 mm-25 mm posteriorly from the balanced position. In another embodiment, an activity of an ankle plantar-flexor is decreased by calibrating the posterior protuberance to 2 mm-15 mm posteriorly from the balanced position. In another embodiment, an activity of an ankle plantar-flexor is decreased by calibrating the posterior protuberance to 1 mm-10 mm posteriorly from the balanced position. In another embodiment, an activity of an ankle plantar-flexor is decreased by calibrating the posterior protuberance to 3 mm-8 mm posteriorly from the balanced position. In another embodiment, an activity of an ankle plantar-flexor is decreased according to the methods described herein by 3-40%. In another embodiment, an activity of an ankle plantar-flexor is decreased according to the methods described herein by 5-25%. In another embodiment, an activity of an ankle plantar-flexor is decreased as much as 25%. Each possibility represents a separate embodiment of the present invention.

In another embodiment, an activity of the plantar-flexor is decreased by heightening the posterior protuberance from the neutral position which is the balanced position (the position wherein the device provides a reduced inversion or a reduced eversion to the subject's foot). In another embodiment, an activity of the plantar-flexor is decreased by increasing the height of the posterior protuberance by 0.5-10 mm. In another embodiment, an activity of the plantar-flexor is decreased by increasing the height of the posterior protuberance by 2-8 mm. In another embodiment, an activity of the plantar-flexor is decreased by increasing the height of the posterior protuberance by 1-4 mm. In another embodiment, an activity of the plantar-flexor is decreased according to the methods described herein by 3-40%. In another embodiment, an activity of the plantar-flexor is decreased according to the methods described herein by 10-30%. In another embodiment, an activity of the plantar-flexor is decreased as much as 35%. Each possibility represents a separate embodiment of the present invention.

In another embodiment, an activity of an ankle plantar-flexor is decreased by calibrating the anterior protuberance posteriorly from the neutral position which is the balanced position (the position wherein the device provides a reduced inversion or a reduced eversion to the subject's foot). In another embodiment, an activity of an ankle plantar-flexor is decreased by calibrating the anterior protuberance to 0.5 mm-25 mm posteriorly from the balanced position. In another embodiment, an activity of an ankle plantar-flexor is decreased by calibrating the anterior protuberance to 2-15 mm posteriorly from the balanced position. In another embodiment, an activity of an ankle plantar-flexor is decreased by calibrating the anterior protuberance to 1-10 mm posteriorly from the balanced position. In another embodiment, an activity of an ankle plantar-flexor is decreased by calibrating the anterior protuberance to 2-8 mm posteriorly from the balanced position. In another embodiment, an activity of an ankle plantar-flexor is decreased according to the methods described herein by 3-40%. In another embodiment, an activity of an ankle plantar-flexor is decreased according to the methods described herein by 5-25%. In another embodiment, an activity of an ankle plantar-flexor is decreased as much as 25%. Each possibility represents a separate embodiment of the present invention.

Knee Muscles

In another embodiment, an activity of the pes anserinus muscles (sartorius semitendinosus and gracilis) is decreased by calibrating the posterior protuberance laterally from the neutral position which is the balanced position (the position wherein the device provides a reduced inversion or a reduced eversion to the subject's foot). In another embodiment, an activity of the pes anserinus muscles (sartorius, semitendinosus and gracilis) is decreased by calibrating the anterior protuberance medially from the neutral position which is the balanced position (the position wherein the device provides a reduced inversion or a reduced eversion to the subject's foot). In another embodiment, an activity of the pes anserinus muscles (sartorius, semitendinosus and gracilis) is decreased by calibrating the posterior protuberance laterally from the neutral position which is the balanced position (the position wherein the device provides a reduced inversion or a reduced eversion to the subject's foot) and the anterior protuberance medially from the balanced position. In another embodiment, an activity of the pes anserinus muscles (sartorius, semitendinosus and gracilis) is decreased by calibrating the posterior protuberance to 0.5-25 mm laterally from the balanced position and the anterior protuberance to 0.5-25 mm medially from the balanced position. In another embodiment, an activity of the pes anserinus muscles (sartorius, semitendinosus and gracilis) is decreased by calibrating the posterior protuberance to 5-20 mm laterally from the balanced position and the anterior protuberance to 2-15 mm medially from the balanced position. In another embodiment, an activity of the pes anserinus muscles (sartorius, semitendinosus and gracilis) is decreased by calibrating the posterior protuberance to 5-15 mm laterally from the balanced position and the anterior protuberance to 2-12 mm medially from the balanced position. In another embodiment, an activity of the pes anserinus muscles (sartorius, semitendinosus and gracilis) is decreased according to the methods described herein by 3-40%. In another embodiment, an activity of the pes anserinus muscles (sartorius, semitendinosus and gracilis) is decreased according to the methods described herein by 5-25%. In another embodiment, an activity of the pes anserinus muscles (Sartorius, semitendinosus and gracilis) is decreased as much as 20%. Each possibility represents a separate embodiment of the present invention.

In another embodiment, an activity of the quadriceps muscle is increased by calibrating the posterior protuberance posteriorly from the neutral position which is the balanced position (the position wherein the device provides a reduced inversion or a reduced eversion to the subject's foot). In another embodiment, an activity of the quadriceps muscle is increased by calibrating the posterior protuberance to 0.5 mm-25 mm posteriorly from the balanced position. In another embodiment, an activity of the quadriceps muscle is increased by calibrating the posterior protuberance to 5-15 mm posteriorly from the balanced position. In another embodiment, an activity of the quadriceps muscle is increased by calibrating the posterior protuberance to 2-8 mm posteriorly from the balanced position. In another embodiment, an activity of the quadriceps muscle is increased according to the methods described herein by 3-30%. In another embodiment, an activity of the quadriceps muscle is increased according to the methods described herein by 5-25%. In another embodiment, an activity of the quadriceps muscle is increased as much as 15%. Each possibility represents a separate embodiment of the present invention.

In another embodiment, an activity of the quadriceps muscle is increased by heightening the posterior protuberance. In another embodiment, an activity of the quadriceps muscle is increased by heightening the posterior protuberance by 0.5 mm-12 mm. In another embodiment, an activity of the quadriceps muscle is increased by heightening the posterior protuberance by 1 mm-8 mm. In another embodiment, an activity of the quadriceps muscle is increased by heightening the posterior protuberance by 1 mm-5 mm. In another embodiment, heightening the posterior protuberance results in a posterior protuberance which is 0.5 mm-12 mm higher than the anterior protuberance. In another embodiment, heightening the posterior protuberance results in that the ankle is in a plantar-flexed position. In another embodiment, heightening the posterior protuberance results in muscle activity increase. In another embodiment, heightening the posterior protuberance results in 5-50% quadriceps muscle activity increase. In another embodiment, heightening the posterior protuberance results in 10-30% quadriceps muscle activity increase. In another embodiment, heightening the posterior protuberance results in as much as 35% quadriceps muscle activity increase. Each possibility represents a separate embodiment of the present invention.

In another embodiment, an activity of the hamstring muscle is increased by calibrating the posterior protuberance anteriorly from the neutral position which is the balanced position (the position wherein the device provides a reduced inversion or a reduced eversion to the subject's foot). In another embodiment, an activity of the hamstring muscle is increased by calibrating the posterior protuberance to 0.5 mm-25 mm anteriorly from the balanced position. In another embodiment, an activity of the hamstring muscle is increased by calibrating the posterior protuberance to 2-20 mm anteriorly from the balanced position. In another embodiment, an activity of the hamstring muscle is increased by calibrating the posterior protuberance to 5-10 mm anteriorly from the balanced position. In another embodiment, an activity of the hamstring muscle is increased according to the methods described herein by 3-30%. In another embodiment, an activity of the hamstring muscle is increased according to the methods described herein by 5-25%. In another embodiment, an activity of the hamstring muscle is increased as much as 15%. Each possibility represents a separate embodiment of the present invention.

In another embodiment, an activity of the hamstring, quad and hip flexors (iliopsoas, rectus femoris) is increased by inserting a weighted spacer between the outsole and the base of the posterior protuberance thus enhancing the activity of the above muscles at the declaration stage of swing (terminal swing) and prepositioning for initial contact stage.

In another embodiment, an activity of the medial knee muscles (vastus medialis and vastus medialis oblique) is increased by calibrating the posterior protuberance posteriorly and laterally from the neutral position which is the balanced position (the position wherein the device provides a reduced inversion or a reduced eversion to the subject's foot). In another embodiment, an activity of the medial knee muscles (vastus medialis and vastus medialis oblique) is increased by calibrating the posterior protuberance to 5 mm-20 mm posteriorly and 3-13 mm laterally from the balanced position. In another embodiment, an activity of the medial knee muscles (vastus medialis and vastus medialis oblique) is increased by calibrating the posterior protuberance to 5 mm-15 mm posteriorly and 5-10 mm laterally from the balanced position. In another embodiment, an activity of the medial knee muscles (vastus medialis and vastus medialis oblique) is increased according to the methods described herein by 3-30%. In another embodiment, an activity of the medial knee muscles (vastus medialis and vastus medialis oblique) is increased according to the methods described herein by 5-25%. In another embodiment, an activity of the medial knee muscles (vastus medialis and vastus medialis oblique) is increased as much as 15%. Each possibility represents a separate embodiment of the present invention.

In another embodiment, an activity of the lateral knee muscles (vastus lateralis) is increased by calibrating the posterior protuberance posteriorly and medially from the neutral position which is the balanced position (the position wherein the device provides a reduced inversion or a reduced eversion to the subject's foot). In another embodiment, an activity of the lateral knee muscles (vastus lateralis) is increased by calibrating the posterior protuberance to 5 mm-20 mm posteriorly and 3-13 mm medially from the balanced position. In another embodiment, an activity of the lateral knee muscles (vastus lateralis) is increased by calibrating the posterior protuberance to 5 mm-15 mm posteriorly and 5-10 mm medially from the balanced position. In another embodiment, an activity of the lateral knee muscles (vastus lateralis) is increased according to the methods described herein by 3-30%. In another embodiment, an activity of the lateral knee muscles (vastus lateralis) is increased according to the methods described herein by 5-25%. In another embodiment, an activity of the lateral knee muscles (vastus lateralis) is increased as much as 15%. Each possibility represents a separate embodiment of the present invention.

In another embodiment, an activity of the knee flexor muscles (gastrocnemius and hamstrings) is increased by heightening the anterior protuberance. In another embodiment, an activity of the knee flexor muscles (gastrocnemius and hamstrings) is increased by heightening the anterior protuberance by 0.5 mm-12 mm. In another embodiment, an activity of the knee flexor muscles (gastrocnemius and hamstrings) is increased by heightening the anterior protuberance by 1 mm-8 mm. In another embodiment, an activity of the knee flexor muscles (gastrocnemius and hamstrings) is increased by heightening the anterior protuberance by 1 mm-5 mm. In another embodiment, heightening the anterior protuberance results in an anterior protuberance which is 0.5 mm-12 mm higher than the posterior protuberance. In another embodiment, heightening the anterior protuberance results in that the ankle is in a dorsi-flexed position. In another embodiment, heightening the anterior protuberance results in muscle activity increase. In another embodiment, heightening the anterior protuberance results in 5-50% knee flexor muscles (gastrocnemius and hamstrings) activity increase. In another embodiment, heightening the anterior protuberance results in 10-30% knee flexor muscles (gastrocnemius and hamstrings) activity increase. In another embodiment, heightening the anterior protuberance results in as much as 35% knee flexor muscles (gastrocnemius and hamstrings) activity increase. Each possibility represents a separate embodiment of the present invention.

In another embodiment, an activity of the quadriceps muscle is decreased by calibrating the posterior protuberance anteriorly from the neutral position which is the balanced position (the position wherein the device provides a reduced inversion or a reduced eversion to the subject's foot). In another embodiment, an activity of the quadriceps muscle is decreased by calibrating the posterior protuberance to 0.5 mm-25 mm anteriorly from the balanced position. In another embodiment, an activity of the quadriceps muscle is decreased by calibrating the posterior protuberance to 5-15 mm anteriorly from the balanced position. In another embodiment, an activity of the quadriceps muscle is decreased by calibrating the posterior protuberance to 2-8 mm anteriorly from the balanced position. In another embodiment, an activity of the quadriceps muscle is decreased according to the methods described herein by 3-30%. In another embodiment, an activity of the quadriceps muscle is decreased according to the methods described herein by 5-25%. In another embodiment, an activity of the quadriceps muscle is decreased as much as 15%. Each possibility represents a separate embodiment of the present invention.

In another embodiment, an activity of the hamstring muscle is decreased by calibrating the posterior protuberance posteriorly from the neutral position which is the balanced position (the position wherein the device provides a reduced inversion or a reduced eversion to the subject's foot). In another embodiment, an activity of the hamstring muscle is decreased by calibrating the posterior protuberance to 0.5 mm-25 mm posteriorly from the balanced position. In another embodiment, an activity of the hamstring muscle is decreased by calibrating the posterior protuberance to 5-20 mm posteriorly from the balanced position. In another embodiment, an activity of the hamstring muscle is decreased by calibrating the posterior protuberance to 7-15 mm posteriorly from the balanced position. In another embodiment, an activity of the hamstring muscle is decreased according to the methods described herein by 3-30%. In another embodiment, an activity of the hamstring muscle is decreased according to the methods described herein by 5-25%. In another embodiment, an activity of the hamstring muscle is decreased as much as 15%. Each possibility represents a separate embodiment of the present invention.

In another embodiment, an activity of the medial knee muscles (vastus medialis and vastus medialis oblique) is decreased by calibrating the posterior protuberance anteriorly and medially from the neutral position which is the balanced position (the position wherein the device provides a reduced inversion or a reduced eversion to the subject's foot). In another embodiment, an activity of the medial knee muscles (vastus medialis and vastus medialis oblique) is decreased by calibrating the posterior protuberance to 5 mm-20 mm anteriorly and 3-13 mm medially from the balanced position. In another embodiment, an activity of the medial knee muscles (vastus medialis and vastus medialis oblique) is decreased by calibrating the posterior protuberance to 5 mm-15 mm anteriorly and 5-10 mm medially from the balanced position. In another embodiment, an activity of the medial knee muscles (vastus medialis and vastus medialis oblique) is decreased according to the methods described herein by 3-30%. In another embodiment, an activity of the medial knee muscles (vastus medialis and vastus medialis oblique) is decreased according to the methods described herein by 5-25%. In another embodiment, an activity of the medial knee muscles (vastus medialis and vastus medialis oblique) is decreased as much as 15%. Each possibility represents a separate embodiment of the present invention.

In another embodiment, an activity of the lateral knee muscles (vastus lateralis) is decreased by calibrating the posterior protuberance anteriorly and laterally from the neutral position which is the balanced position (the position wherein the device provides a reduced inversion or a reduced eversion to the subject's foot). In another embodiment, an activity of the lateral knee muscles (vastus lateralis) is decreased by calibrating the posterior protuberance to 5 mm-20 mm anteriorly and 3-13 mm laterally from the balanced position. In another embodiment, an activity of the lateral knee muscles (vastus lateralis) is decreased by calibrating the posterior protuberance to 5 mm-15 mm anteriorly and 5-10 mm laterally from the balanced position. In another embodiment, an activity of the lateral knee muscles (vastus lateralis) is decreased according to the methods described herein by 3-30%. In another embodiment, an activity of the lateral knee muscles (vastus lateralis) is decreased according to the methods described herein by 5-25%. In another embodiment, an activity of the lateral knee muscles (vastus lateralis) is decreased as much as 15%. Each possibility represents a separate embodiment of the present invention.

In another embodiment, an activity of the hamstring muscle is decreased by heightening the posterior protuberance. In another embodiment, an activity of the hamstring muscle is decreased by heightening the posterior protuberance by 0.5 mm-12 mm. In another embodiment, an activity of the hamstring muscle is decreased by heightening the posterior protuberance by 1 mm-8 mm. In another embodiment, an activity of the hamstring muscle is decreased by heightening the posterior protuberance by 1 mm-5 mm. In another embodiment, heightening the posterior protuberance results in a posterior protuberance which is 0.5 mm-12 mm higher than the anterior protuberance. In another embodiment, heightening the posterior protuberance results in that the ankle is in a plantar-flexed position. In another embodiment, heightening the posterior protuberance results in muscle activity decreased. In another embodiment, heightening the posterior protuberance results in 5-50% hamstring muscle activity decreased. In another embodiment, heightening the posterior protuberance results in 10-30% hamstring muscle activity decreased. In another embodiment, heightening the posterior protuberance results in as much as 35% hamstring muscle activity decreased. Each possibility represents a separate embodiment of the present invention.

In another embodiment, heightening the anterior protuberance results in decreased activity of the quadriceps. In another embodiment, an activity of the quadriceps muscle is decreased by heightening the anterior protuberance. In another embodiment, an activity of the quadriceps muscle is decreased by heightening the anterior protuberance by 0.5 mm-12 mm. In another embodiment, an activity of the quadriceps muscle is decreased by heightening the anterior protuberance by 1 mm-8 mm. In another embodiment, an activity of the quadriceps muscle is decreased by heightening the anterior protuberance by 1 mm-5 mm. In another embodiment, heightening the anterior protuberance results in 5-50% quadriceps muscle activity decreased. In another embodiment, heightening the anterior protuberance results in 10-30% quadriceps muscle activity decreased. In another embodiment, heightening the anterior protuberance results in as much as 35% quadriceps muscle activity decreased. Each possibility represents a separate embodiment of the present invention.

Hip Muscles

In another embodiment, hip extensors comprise: gluteus maximus, posterior gluteus medius, biceps femoris, semitendinosus and semimembranosus. In another embodiment, hip abductors comprise: gluteus medius, gluteus minimus and tensor fascia lata. In another embodiment, hip external rotators comprise: piriformis, quadrates femoris, obturator internus obturator externus, gemellus superior and gemellus inferior. Each possibility represents a separate embodiment of the present invention.

In another embodiment, hip flexors comprise: illiacus, rectus femoris, tensor fascia lata, psoas major and psoas minor. In another embodiment, an activity of a hip abductors and external rotator muscle is increased by calibrating the posterior protuberance medially from the neutral position which is the balanced position (the position wherein the device provides a reduced inversion or a reduced eversion to the subject's foot). In another embodiment, an activity of a hip external rotator muscle is increased by calibrating the posterior protuberance to 0.5 mm-25 mm medially from the balanced position. In another embodiment, an activity of a hip external rotator muscle is increased by calibrating the posterior protuberance to 2-20 mm medially from the balanced position. In another embodiment, an activity of a hip external rotator muscle is increased by calibrating the posterior protuberance to 5-10 mm medially from the balanced position. In another embodiment, an activity of a hip external rotator muscle is increased according to the methods described herein by 3-30%. In another embodiment, an activity of a hip external rotator muscle is increased according to the methods described herein by 5-25%. In another embodiment, an activity of a hip external rotator muscle is increased according to the methods described herein by 5-10%. In another embodiment, an activity of a hip external rotator muscle is increased as much as 15%. Each possibility represents a separate embodiment of the present invention.

In another embodiment, an activity of a hip extensor muscle is increased by expanding the height of the anterior protuberance from the neutral position which is the balanced position (the position wherein the device provides a reduced inversion or a reduced eversion to the subject's foot). In another embodiment, expanding the height of the anterior protuberance over the height of the posterior protuberance induces the ankle to be in a dorsi-flexed position. In another embodiment, an activity of a hip extensor muscle is increased by expanding the height of the anterior protuberance by 0.5-15 mm from the balanced position. In another embodiment, an activity of a hip extensor muscle is increased by expanding the height of the anterior protuberance by 2-12 mm from the balanced position. In another embodiment, an activity of a hip extensor muscle is increased by expanding the height of the anterior protuberance by 4-10 mm from the balanced position. In another embodiment, an activity of a hip extensor muscle is increased according to the methods described herein by 3-30%. In another embodiment, an activity of a hip extensor muscle is increased according to the methods described herein by 5-25%. In another embodiment, an activity of a hip extensor muscle is increased according to the methods described herein by 5-10%. In another embodiment, an activity of a hip extensor muscle is increased as much as 15%. Each possibility represents a separate embodiment of the present invention.

In another embodiment, an activity of a hip abductor muscle is increased by increasing the weight in the posterior protuberance (via a disc shaped spacer) thus shifting the balance from the neutral position which is the balanced position (the position wherein the device provides a reduced inversion or a reduced eversion to the subject's foot). In another embodiment, an activity of a hip abductor muscle is increased by adding a weight (spacer) of 2-500 g to the posterior protuberance. In another embodiment, an activity of a hip abductor muscle is increased by adding a weight (spacer) of 5-250 g to the posterior protuberance. In another embodiment, an activity of a hip abductor muscle is increased by adding a weight (spacer) of 2-12 g to the posterior protuberance. In another embodiment, an activity of a hip abductor muscle is increased by adding a weight (spacer) of 50-100 g to the posterior protuberance. Each possibility represents a separate embodiment of the present invention.

In another embodiment, tuning is measured by an electromyogram (EMG). In another embodiment, increasing muscle activity is strengthening a muscle. In another embodiment, muscle strengthening is measured by conventional tests. Each possibility represents a separate embodiment of the present invention.

Figure 16A:
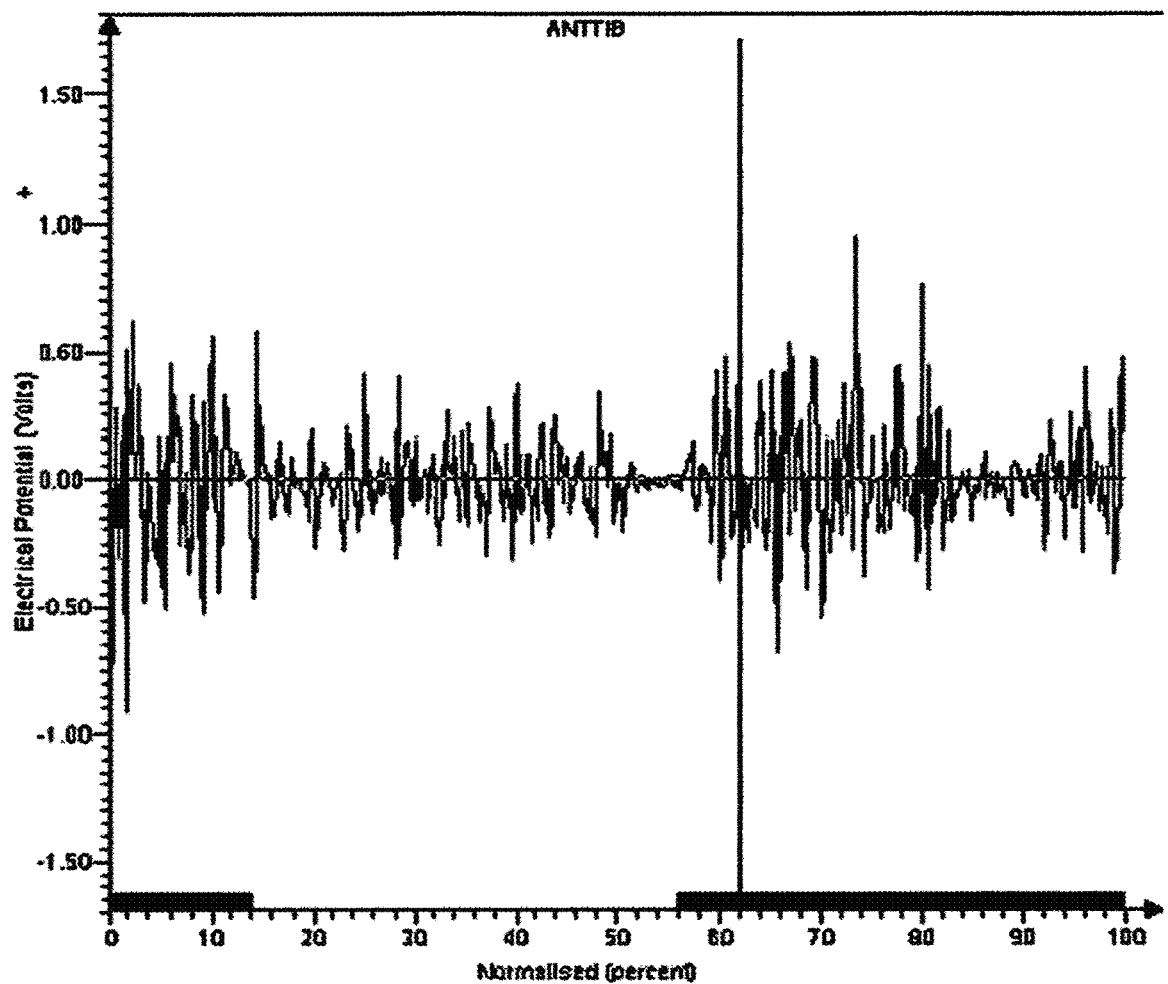
FIG. 16A depicts an EMG plot of the tibialis anterior during gait when the subject was walking with the footwear calibrated in 8 mm of plantar flexion.
Figure 16B:
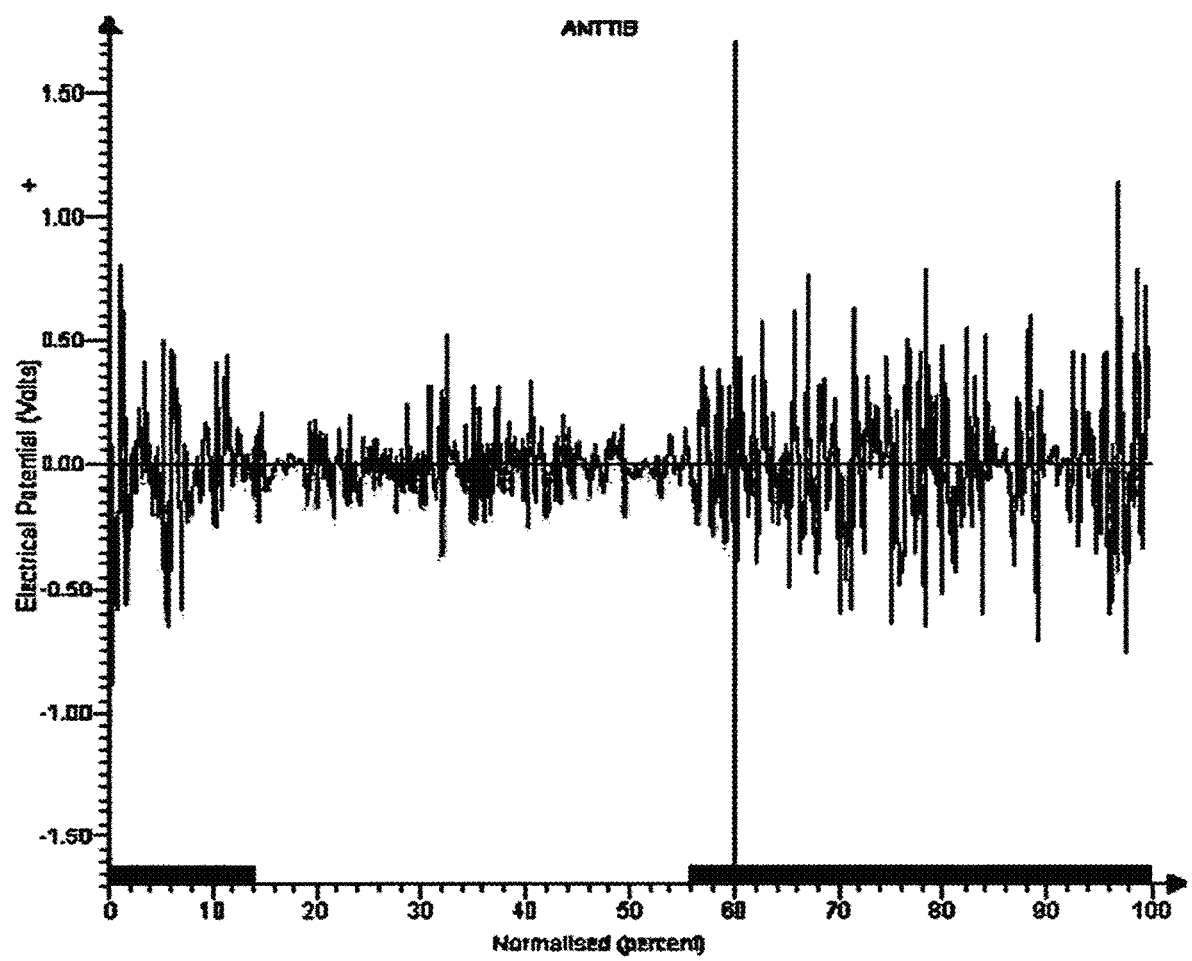
FIG. 16B depicts an EMG plot of the tibialis anterior during gait when the subject was walking with the footwear calibrated in 6 mm of dorsi flexion.
Figure 16C:
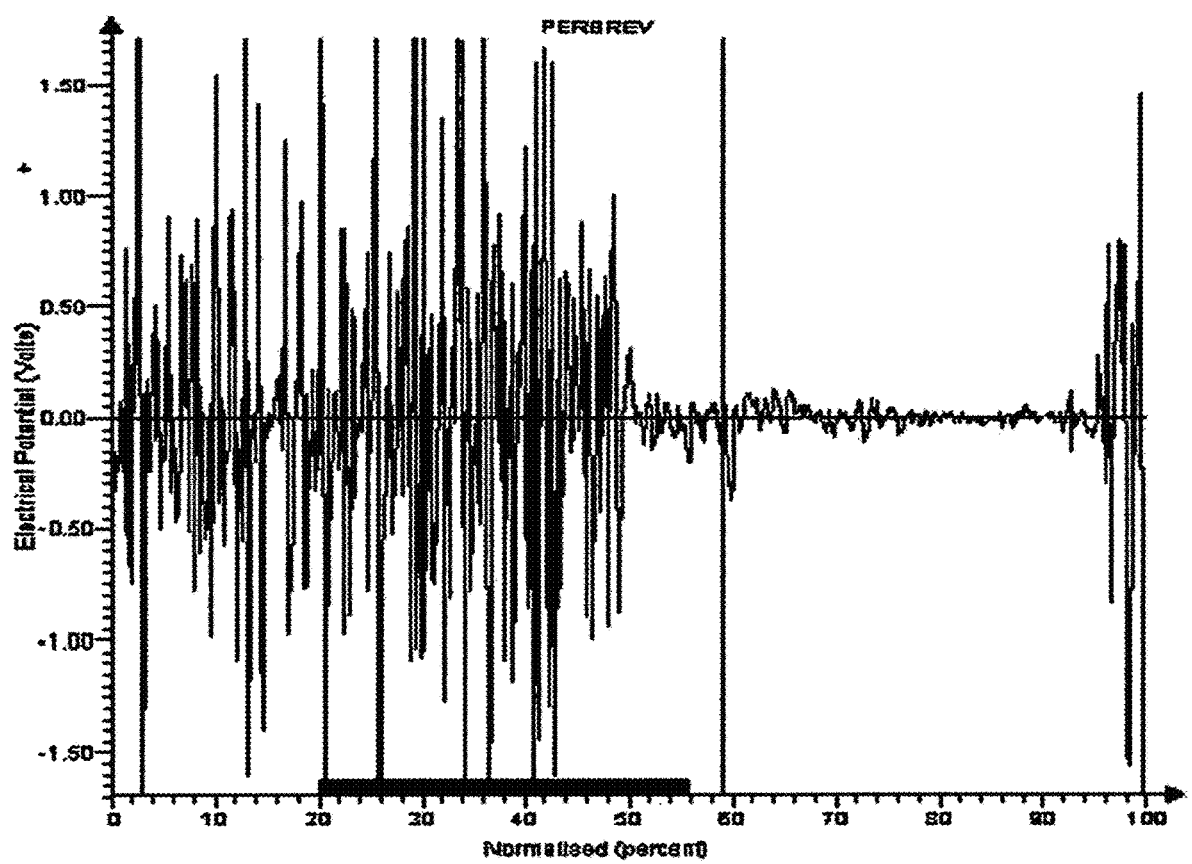
FIG. 16C depicts an EMG plot of the peroneus brevis during gait when the subject was walking with the footwear so that both the anterior and the posterior protuberances were calibrated and fixed 15 mm medial to the neutral position.
Figure 16D:
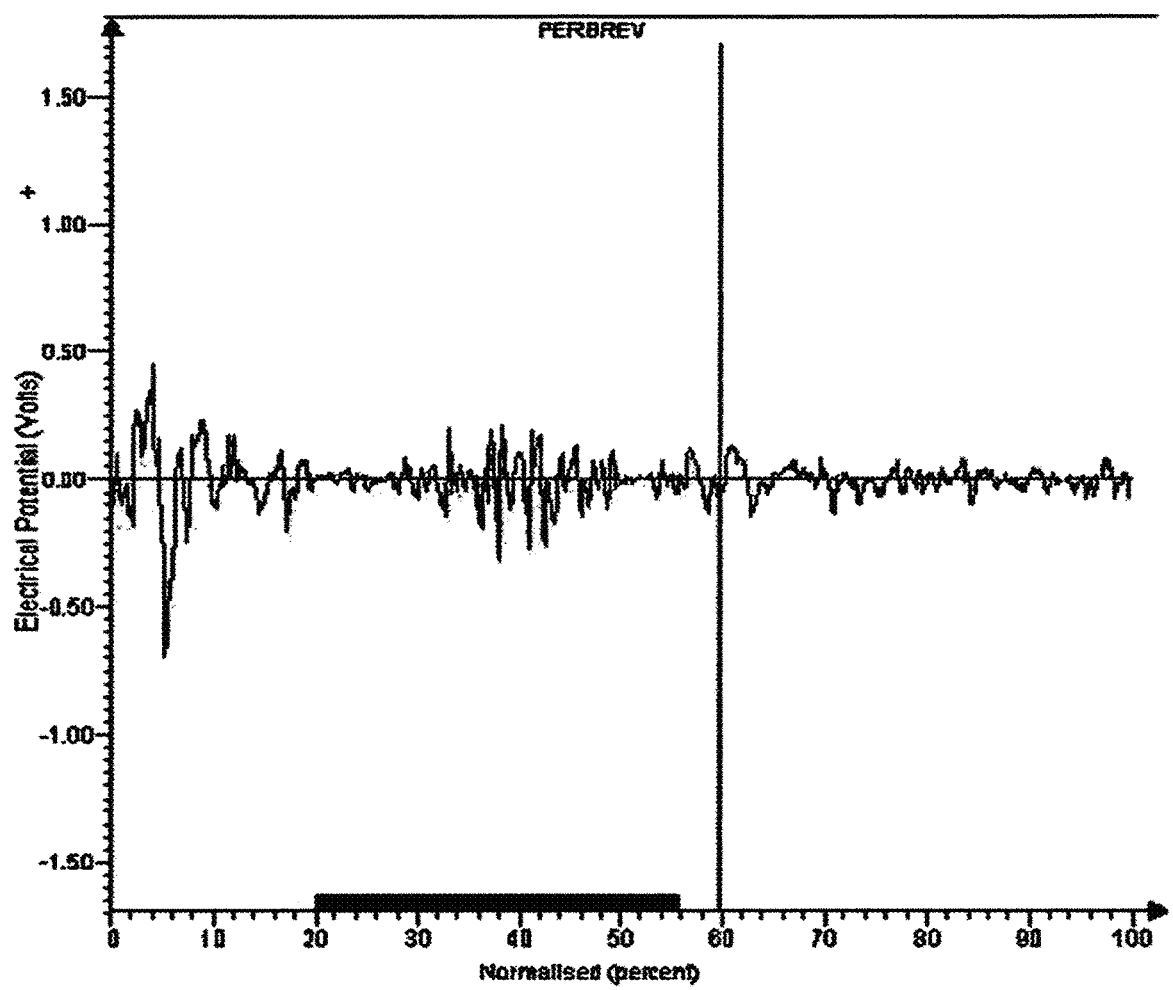
FIG. 16D depicts an EMG plot of the peroneus brevis during gait when the subject was walking with the system so that both the anterior and the posterior protuberances were calibrated and fixed 10 mm. lateral to the neutral position.

In another embodiment, FIGS. 16A-16-D present the EMG findings of the peroneus brevis and the tibialis anterior measured in a healthy subject walking at a comfortable speed with the system in various calibrations (detailed herein). In another embodiment, each of the EMG graphs should be viewed from left to right. The Y axis represents the muscles electrical activity as measured by the EMG device. The X axis represents percent of the gait cycle, starting at the initial contact phase. The vertical dark line at 60% of the gait cycle represents the end of stance phase and the beginning of swing phase.

In another embodiment, comparison of 16A and 16B revealed that the EMG activity of the tibialis anterior muscle in a dorsi-flexed position is greater during swing. In another embodiment, a visual comparison of figures C and D revealed that the peroneus brevis is far more active in a medial calibration than in the lateral calibration.

In another embodiment, provided herein a method based on the notion that calibration of a protuberance supporting an area under a subject foot comprises a muscle tuning effect and/or therapeutic effect as described herein. In another embodiment, calibrating a protuberance which comprises calibrating convexity, calibrating height, calibrating weight, calibrating position, or any combination thereof comprises a muscle tuning effect and/or therapeutic effect according to the methods described herein. Calibrating both an anterior protuberance and a posterior protuberance, in a subject in need thereof, according to the embodiments of the invention comprises a muscle tuning effect and/or therapeutic effect according to the methods described herein. In another embodiment, placement and calibration of a protuberance comprises the induction of a differential interference during gait or walking which provides a favorable a muscle tuning effect and/or therapeutic effect according to the methods described herein. In another embodiment, the term "interference" comprises disturbance, interruption, interposition, perturbation, obstruction, or any combination thereof. In another embodiment, the ability to fine-tune an induced interference under a foot of a subject enables muscle tuning In another embodiment, provided herein a method of treating a patient suffering from musculoskeletal pain in the lower limb by specific placement of at least two calibrated, differential disturbances or protuberances under the patient's feet. In another embodiment, the terms "patient" and "subject" are used interchangeably. Each possibility represents a separate embodiment of the present invention.

In another embodiment, provided herein that the posterior protuberance is a bulbous protuberance. In another embodiment, provided herein that the anterior protuberance is a bulbous protuberance. In another embodiment, provided herein that both the posterior protuberance and the anterior protuberance are bulbous protuberances. Each possibility represents a separate embodiment of the present invention.

In another embodiment, provided herein a method of tuning a muscle and/or treating a subject afflicted with a lower limb joint pathology such as but not limited to a lower limb osteoarthritis comprises the steps of: securing a device to a subject's foot, whereby the device comprises a foot securing mean, a support member operably attached to the securing mean, and a moveable anterior protuberance and a moveable posterior protuberance; calibrating the posterior protuberance and the anterior protuberance to a balanced position, the balanced position comprises a position whereby the device provides a reduced inversion or a reduced eversion to the subject's foot during the stance phases; and fixing the posterior protuberance and the anterior protuberance to the support member in the balanced position. In another embodiment, lower limb osteoarthritis is hip osteoarthritis. In another embodiment, lower limb osteoarthritis is ankle osteoarthritis. In another embodiment, lower limb osteoarthritis is foot osteoarthritis. In another embodiment, lower limb osteoarthritis is knee osteoarthritis. In another embodiment, the device provides controllable inversion or a controllable eversion. Each possibility represents a separate embodiment of the present invention.

In another embodiment, a lower limb joint pathology comprises: a lower limb joint disease, a lower limb joint degenerative disease, a lower limb degenerative disease, a lower limb musculoskeletal pathology, a lower limb musculoskeletal trauma, a lower limb musculoskeletal disease, lower limb osteoarthritis, or any combination thereof. In another embodiment, a lower limb joint pathology is associated with lower limb musculoskeletal pain.

In another embodiment, a subject is a human subject. In another embodiment, a subject is a human subject afflicted with a lower limb joint pathology. In another embodiment, a lower limb joint pathology is a hip, an ankle, a foot, or a knee degenerative joint disease. In another embodiment, a lower limb joint pathology comprises a degenerative joint disease such as osteoarthritis. In another embodiment, a degenerative joint disease is lower limb osteoarthritis. In another embodiment, a degenerative joint disease is knee osteoarthritis. In another embodiment, a hip, an ankle, a foot, or a knee osteoarthritis is primary osteoarthritis. Each possibility represents a separate embodiment of the present invention.

In another embodiment, a degenerative joint disease is foot osteoarthritis. In another embodiment, a degenerative joint disease is hip osteoarthritis. In another embodiment, osteoarthritis is secondary osteoarthritis. In another embodiment, knee osteoarthritis is secondary knee osteoarthritis. In another embodiment, classification into either primary or secondary depends on if there is or is not an identifiable underlying cause. Each possibility represents a separate embodiment of the present invention.

In another embodiment, a lower limb joint pathology is patellar compression. In another embodiment, a lower limb joint pathology is joint line tenderness. In another embodiment, a lower limb joint pathology is joint line effusion. In another embodiment, a lower limb joint pathology is prepatellar bursitis. In another embodiment, a lower limb joint pathology is infrapatellar tendonitis. In another embodiment, tendonitis includes tendinosis, degenerative changes in the tendon or any pain arising from the tendon. In another embodiment, a lower limb joint pathology is pain and/or tenderness in any patellar or prepatellar anatomical structure. Each possibility represents a separate embodiment of the present invention.

In another embodiment, a lower limb joint pathology is a lower limb degenerative joint disease. In another embodiment, a lower limb joint pathology is medial tibiofemoral/lateral tibiofemoral/patella-femoral osteoarthritis (OA) or any combination thereof (primary or secondary). In another embodiment, a lower limb joint pathology is Pes-anserinus bursitis. In another embodiment, a lower limb joint pathology is Pes-anserinus tendinosis. In another embodiment, a lower limb joint pathology is characterized by anterior knee pain and/or patello-femoral pain. In another embodiment, a lower limb joint pathology is a meniscal tear (both degenerative and traumatic). In another embodiment, a lower limb joint pathology is ligament tear/partial tear/strain/post reconstruction (ACL, PCL, MCL, LCL), or any combination thereof. In another embodiment, a lower limb joint pathology includes pre/post arthroplasty including total, hemi, or resurfacing and use of the methods as described herein. In another embodiment, a lower limb joint pathology is tibial plateau fracture. In another embodiment, a lower limb joint pathology is a patellar fracture. In another embodiment, a lower limb joint pathology is osteonecrosis (both in the tibia and femur). In another embodiment, a lower limb joint pathology is Patelar tendonitis. In another embodiment, a lower limb joint pathology is Osgood schlatter. In another embodiment, a lower limb joint pathology comprises post lower limb surgery. Each possibility represents a separate embodiment of the present invention.

In another embodiment, a lower limb joint pathology is knee replacement. In another embodiment, a lower limb joint pathology is hip replacement. In another embodiment, a lower limb joint pathology is hip resurfacing. In another embodiment, a lower limb joint pathology is Trochanteric bursitis. In another embodiment, a lower limb joint pathology comprises necrosis within the lower limb joint. In another embodiment, a lower limb joint pathology comprises hip fracture, both with and without surgical fixation. In another embodiment, a lower limb joint pathology comprises developmental dysplasia of the hip. In another embodiment, a lower limb joint pathology comprises Tendonitis/tendinosis of the hip. In another embodiment, a lower limb joint pathology comprises impingement of the hip. Each possibility represents a separate embodiment of the present invention.

In another embodiment, a lower limb joint pathology comprises Osteochondritis dissecans of the foot or ankle. In another embodiment, a lower limb joint pathology comprises acute or chronic instability of the foot or ankle. In another embodiment, a lower limb joint pathology comprises Ligament Sprain, tear, and/or repair within a joint of the foot or ankle. In another embodiment, a lower limb joint pathology comprises a foot or ankle fracture. In another embodiment, a lower limb joint pathology comprises Plantar Fascitis. In another embodiment, a lower limb joint pathology comprises Tibialis posterior insufficiency and/or dysfunction. In another embodiment, a lower limb joint pathology comprises a pronating foot. In another embodiment, a lower limb joint pathology comprises a supinating foot. In another embodiment, a lower limb joint pathology comprises of pes planus or pes cavus. Each possibility represents a separate embodiment of the present invention.

In another embodiment, a lower limb joint pathology comprises ilio-tibial band (ITB) syndrome. In another embodiment, a lower limb joint pathology comprises hyperlaxity or hypermobility. In another embodiment, a lower limb joint pathology comprises muscular atrophy. In another embodiment, a lower limb joint pathology comprises tumors within a lower limb. In another embodiment, a lower limb joint pathology comprises tumors which affect a joint of the lower limb. Each possibility represents a separate embodiment of the present invention.

This invention provides, in another embodiment, a method of treating a lower limb pathology comprising the step of tuning a lower limb skeletal muscle in a subject suffering from a lower limb pathology, wherein tuning a lower limb skeletal muscle comprises the steps of: (a) Securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to: (1) a balanced position, the balanced position comprises a position whereby the device provides a reduced inversion or a reduced eversion to the subject's foot during the stance phases; and (2) a muscle tuning position; and (c) fixing the posterior protuberance and the anterior protuberance to the support member.

In another embodiment, the methods are directed to treating a lower limb pathology that is treatable according to the invention by differential muscle tuning. In another embodiment, the methods are directed to treating a lower limb pathology that is at least partially treatable (may involve additional treatments that are known to one of skill in the art (surgery, medication, etc.)) according to the invention by differential muscle tuning. In another embodiment, the resultant tuning of a muscle or muscles described here forth represent the desired tuning achieved by the method of the invention.

In another embodiment, foot osteoarthritis requires tuning the tibialis anterior (increased or decreased activity) depending on the subject and in which activity of the gastrocnemius and soleus are tuned depending on the subject or any or all of the above. In another embodiment, a degenerative joint disease is hip osteoarthritis in which the activity of the hamstrings and quadriceps are increased during late swing and prepositioning for initial contact. In another embodiment, osteoarthritis is secondary osteoarthritis in which muscular activity is tuned according to the afflicted joint. In another embodiment, knee osteoarthritis is secondary knee osteoarthritis in which the activity of the quadriceps is to be increased and the activity of the hamstrings and pes anserinus muscles is to be decreased.

In another embodiment, a lower limb joint pathology is patellar compression in which the activity of the quadriceps is decreased or in which the activity of the vastus lateralis is decreased or in which the activity of the vastus medialis (vastus medialis oblique) is increased or any combination thereof. In another embodiment, a lower limb joint pathology is joint line effusion in which the activity of various muscles is increased differentially according to the medical examination (due to muscle inhibition). In another embodiment, a lower limb joint pathology is prepatellar tendinosis in which the activity of the quadriceps is decreased or in which the timing of quadriceps is altered or any or both of the above. In another embodiment, a lower limb joint pathology is pain and/or tenderness in any patellar or prepatellar anatomical structure in which the activity of the quadriceps is decreased or in which the activity of the vastus lateralis is decreased or in which the activity of the vastus medialis (vastus medialis oblique) is increased or any combination thereof. Each possibility represents a separate embodiment of the present invention.

In another embodiment, a lower limb joint pathology is a lower limb degenerative joint disease in which the activity of various muscles is tuned depending on the afflicted joint. In another embodiment, a lower limb joint pathology is medial tibio-femoral osteoarthritis (OA) in which the activity of the quadriceps is increased and the activity of the hamstrings and pes anserinus muscles is decreased. In another embodiment, a lower limb joint pathology is lateral tibio-femoral osteoarthritis in which the activity of the medial knee muscles, hip abductors and/or hip external rotators is increased. In another embodiment, a lower limb joint pathology is patello-femoral OA in which the activity of the quadriceps is decreased or in which the activity of the vastus lateralis is decreased or in which the activity of the vastus medialis (vastus medialis oblique) is increased or any combination thereof.

In another embodiment, a lower limb joint pathology is Pes-anserinus bursitis in which the activity of the pes anserinus muscles is reduced. In another embodiment, a lower limb joint pathology is characterized by anterior knee pain and/or patello-femoral pain in which the activity of the quadriceps is decreased or hi which the activity of the vastus lateralis is decreased or in which the activity of the vastus medialis (vastus medialis oblique) is increased and in which the activity of the hip abductors and external rotators is increased or any combination thereof.

In another embodiment, a lower limb joint pathology is a meniscal tear (both degenerative and traumatic) in which the activity of the hamstrings is reduced. In another embodiment, a lower limb joint pathology is ligament tear/partial tear/strain/post reconstruction (ACL, PCL, MCL, LCL) in which the timing of various muscles is tuned or the activity of the hamstrings is increased and in which the activity of the quadriceps is reduced, or any combination thereof. In another embodiment, a lower limb joint pathology includes pre/post arthroplasty including total, hemi, or resurfacing and use of the methods as described herein in which the differential timing of activity of various muscles throughout the operated lower limb is tuned or in which the differential activity of various muscles throughout the operated lower limb is increased or any combination thereof. In another embodiment, a lower limb joint pathology is tibial plateau fracture in which the activity of the quadriceps is increased or the activity of the hamstrings is decreased or the activity of the hip abductors is increased, or any combination thereof. In another embodiment, a lower limb joint pathology is osteonecrosis (both in the proximal tibia and distal femur or proximal femur) in which the activity of the hamstrings is reduced or the activity of the quadriceps is increased or the activity or the timing of various muscles in the lower limb is tuned or any combination thereof. In another embodiment, a lower limb joint pathology is patellar tendinosis in which the activity of the quadriceps is decreased or in which the activity of the vastus lateralis is decreased or in which the activity of the vastus medialis (vastus medialis oblique) is increased or any combination thereof.

In another embodiment, a lower limb joint pathology is Osgood Schlatter in which the activity of the quadriceps is reduced. In another embodiment, a lower limb joint pathology comprises post lower limb surgery in which the timing of various muscles in the lower limb is tuned or the activity of various muscles in the lower limb is increased or in which the activity of various muscles in the lower limb is decreased or any combination thereof depending on the type of surgery as will be readily understood, in view of this disclosure, by one of skill in the art. Each possibility represents a separate embodiment of the present invention.

In another embodiment, a lower limb joint pathology is hip replacement in which the activity of the hip abductors is increased or in which the timing of various muscles in the lower limb is tuned or any combination thereof. In another embodiment, a lower limb joint pathology is hip resurfacing in which the activity of the hip abductors is increased or in which the timing of various muscles in the lower limb is tuned or any combination thereof. In another embodiment, a lower limb joint pathology is Trochanteric bursitis in which the activity of the hip abductors and tensor fascia lata is reduced or in which the timing of the hip abductors and tensor fascia lata is tuned or any combination thereof. In another embodiment, a lower limb joint pathology comprises necrosis within the lower limb joint in which the timing of various muscles in the lower limb is tuned or the activity of various muscles in the lower limb is increased or in which the activity of various muscles in the lower limb is decreased or any combination thereof depending on the afflicted bone. In another embodiment, a lower limb joint pathology comprises hip fracture in which the activity of the hip abductors and external rotators are increased. In another embodiment, a lower limb joint pathology comprises developmental dysplasia of the hip in which the activity of the hip abductors and external rotators are increased. In another embodiment, a lower limb joint pathology comprises Tendonitis/tendinosis of the hip in which the activity of various hip muscles is increased, decreased or the timing of these muscles is tuned or any combination thereof. Each possibility represents a separate embodiment of the present invention.

In another embodiment, a lower limb joint pathology comprises Osteochondritis dissecans of the foot or ankle in which the activity of the plantar-flexors is decreased or the timing of the plantar-flexors is tuned or the activity of the dorsi-flexors is increased or the timing of the activity of the dorsi-flexors is tuned, or any combination thereof. In another embodiment, a lower limb joint pathology comprises acute or chronic instability of the foot or ankle in which the activity of the evertors is decreased or in which the timing of the evertors is tuned or in which the activity of the invertors is increased, or any combination thereof. In another embodiment, a lower limb joint pathology comprises ligament Sprain, tear, and/or repair within a joint of the foot or ankle in which the activity of various foot and ankle muscles are increased or decreased or the timing of the activity of various foot and ankle muscles is tuned or any combination thereof depending on the type of ligament Sprain, tear, and/or repair.

In another embodiment, a lower limb joint pathology comprises Plantar Fascitis in which the activity of the plantar-flexors is decreased. In another embodiment, a lower limb joint pathology comprises Tibialis posterior insufficiency and/or dysfunction in which the timing of the activity of the invertors is tuned or the activity of the invertors is increased or any combination thereof. In another embodiment, a lower limb joint pathology comprises a pronating foot in which the timing of the invertors is tuned or the activity of the invertors is increased or any combination thereof. In another embodiment, a lower limb joint pathology comprises of pes planus in which the timing of the activity of the invertors is tuned or the activity of the invertors is increased or any combination thereof. In another embodiment, a lower limb joint pathology comprises of pes cavus in which the timing of the activity of the invertors is tuned or the activity of the evertors is increased or any combination thereof. Each possibility represents a separate embodiment of the present invention.

In another embodiment, a lower limb joint pathology comprises hyper-laxity or hypermobility in which the activity of various muscles in the lower limb is increased or the timing of various muscles in the lower limb is tuned or any combination thereof. In another embodiment, a lower limb joint pathology comprises muscular atrophy in which the activity of various muscles in the lower limb is increased depending on the atrophied muscle. In another embodiment, a lower limb joint pathology comprises tumors within a lower limb in which the timing of various muscles in the lower limb is tuned or the activity of various muscles in the lower limb is increased or in which the activity of various muscles in the lower limb is decreased or any combination thereof depending on the afflicted tissue. In another embodiment, a lower limb joint pathology comprises tumors which affect a joint of the lower limb in which the timing of various muscles in the lower limb is tuned or the activity of various muscles in the lower limb is increased or in which the activity of various muscles in the lower limb is decreased or any combination thereof depending on the afflicted joint. Each possibility represents a separate embodiment of the present invention In another embodiment, the current invention can be used for performance enhancement in athletes. In another embodiment, athletes training cause constant muscle straining. In another embodiment, strained muscles are tuned according to the invention by tuning the timing of such muscles-task specific tuning (i.e. for running, for jumping, etc.). In another embodiment, athletes exercise with a device of the invention. In another embodiment, a device of the invention significantly recovery time following intense training, competitive event, or injury by calibrating the device to a configuration which decreases the activity of the injured or overworked muscle (and therefore promotes rest and recovery of strained muscles).

In another embodiment, the current methods are utilized as preventive measures. In another embodiment, the current methods are utilized for the prevention of injuries in subjects susceptible for lower limb joint pathology or lower limb musculoskeletal pathology. In another embodiment, such subjects are elderly subjects in which the timing of various lower limb muscles needs to be tuned or that the activity of various lower limb muscles needs to be increased or any combination thereof. In another embodiment, the muscles which need to be tuned may vary according to the subject's musculoskeletal condition. In another embodiment, such subjects are subjects whose daily activities require prolonged standing (surgeons, airline cabin crew members, cooks etc.) which harm the lower limbs. In another embodiment, the use of a device of the invention by subjects whose daily activities require prolonged standing can compensate or prevent lower limb musculoskeletal pathologies and induce proper gait cycle.

In another embodiment, muscle tuning and/or treating or treatment according to the invention comprises diminishing, alleviating, reducing, inhibiting, improving, reversing, and/or ameliorating: pain, stiffness, swelling, inflammation, cartilage degeneration, osteophytes, narrowing of joint space, effusion, muscular atrophy, deterioration of neuromuscular control, deterioration of proprioception, bracing, pathological moments, restricted range of motion, excessive range of motion, gait disorders, limping, compensatory gait, antalgic gait, asymmetry in gait, guarding of muscles, loosening of ligaments, loosening of joint capsule, stretching of ligaments, stretching of joint capsule, reduced step length, reduced single limb support, increased single limb support, reduced gait velocity, or any combination thereof. In another embodiment, treating or treatment according to the invention comprises diminishing, alleviating, reducing, inhibiting, improving, reversing, and/or ameliorating bone marrow edema, lesions, subchondral bone changes, softening of cartilage, fibriling and thinning of cartilage, ebonization of the bone, or any combination thereof. Each possibility represents a separate embodiment of the present invention.

In another embodiment, muscle tuning and/or treating comprise performing a variety of maneuvers in a proprioceptive and/or kinesthetic exercise plan for the foot, lower and upper leg, low back and even upper torso and other body parts and organs. In another embodiment muscle tuning and/or treating comprise performing a variety of walking and or gait exercise plan for the lower foot, upper leg and even upper torso and other body parts and organs. Each possibility represents a separate embodiment of the present invention.

In another embodiment, the subject is suffering from pain stemming from a lower limb joint pathology. In another embodiment, the subject is suffering from pain, a joint pain, tenderness, stiffness, locking, an effusion, or any combination thereof. In another embodiment, the subject is suffering from a decreased movement secondary to pain. In another embodiment, the subject is suffering from regional muscles atrophy. In another embodiment, the subject is suffering from lax ligaments. In another embodiment, the subject is suffering from crackling noise ("crepitus") when the affected joint is moved or touched. In another embodiment, the subject is suffering from muscle spasm. In another embodiment, the subject is suffering from tendons contractions. In another embodiment, the methods as described alleviate a painful joint. In another embodiment, the methods as described treat the underlying causes of joint pain. Each possibility represents a separate embodiment of the present invention.

Osteoarthritis

In another embodiment, the subject is suffering from osteoarthritis. In another embodiment, the subject is suffering from lower limbs osteoarthritis. In another embodiment, the subject is suffering from hips osteoarthritis. In another embodiment, the subject is suffering from feet osteoarthritis. In another embodiment, the subject is suffering from a joint effusion (water on the knee in lay terms). Each possibility represents a separate embodiment of the present invention.

In another embodiment, the subject is at risk of being afflicted with osteoarthritis. In another embodiment, the subject is exposed to elevated mechanical stress on the joints. In another embodiment, the subject is afflicted with misalignments of bones caused by congenital or pathogenic causes. In another embodiment, the subject is overweight or obese. In another embodiment, the subject suffers from loss of strength in muscles supporting joints, impairment of peripheral nerves, uncoordinated movements that overstress joints, ligaments, muscles, tendons, or any combination thereof. Each possibility represents a separate embodiment of the present invention.

In another embodiment, the subject is afflicted with osteophytes. In another embodiment, the methods as described herein inhibit narrowing of the joint space. In another embodiment, the methods as described herein expand the joint space. In another embodiment, the methods as described herein inhibit increased subchondral bone density. In another embodiment, the methods as described herein increase the water content of the cartilage. In another embodiment, the methods as described herein increase proteoglycan content of the cartilage. In another embodiment, the methods as described herein inhibit inflammation of the surrounding joint capsule. In another embodiment, the methods as described herein inhibit "spurs" or osteophytes that form on the margins of the joints. In another embodiment, the methods as described herein are used as a prevention measure for subjects at risk of being afflicted with osteoarthritis. In another embodiment, subjects at risk of being afflicted with osteoarthritis are subjects of whose siblings are afflicted with osteoarthritis. Each possibility represents a separate embodiment of the present invention.

In another embodiment, osteoarthritis is primary generalized nodal osteoarthritis. In another embodiment, osteoarthritis is erosive osteoarthritis. In another embodiment, osteoarthritis is inflammatory osteoarthritis. In another embodiment, osteoarthritis is secondary osteoarthritis that is caused by other factors but the resulting pathology is the same as for primary osteoarthritis. Each possibility represents a separate embodiment of the present invention.

In another embodiment, lower limb osteoarthritis (OA) is characterized by pain, stiffness, swelling, inflammation, cartilage degeneration, osteophytes, narrowing of joint space, restricted range of motion, effusion, muscular atrophy, deterioration of neuromuscular control, deterioration of proprioception, bracing, pathological moments, gait disorders, limping, compensatory gait, antalgic gait, asymmetry in gait, guarding of muscles, loosening of ligaments, loosening of joint capsule, stretching of ligaments, stretching of joint capsule, reduced step length, or any combination thereof. Each possibility represents a separate embodiment of the present invention.

Lower Limb Musculoskeletal Pain

In another embodiment, muscle tuning according to the methods described herein alleviates and/or reduces pain in a lower limb. In another embodiment, muscle tuning according to the methods described herein inhibits or reduces inflammation in a lower limb.

In another embodiment, "pain" as used herein comprises a sharp ache. In another embodiment, "pain" as used herein comprises a burning sensation in the associate muscles and tendons. In another embodiment, "pain" as used herein comprises continuous pain. In another embodiment, "pain"

as used herein comprises is a momentary pain. In another embodiment, "pain" as used herein comprises seasonal pain (winter, summer or change of weather). In another embodiment, "pain" as used herein comprises activity specific pain such as sports or any other physical activity related pain. Each possibility represents a separate embodiment of the present invention.

In another embodiment, provided herein a method of treating a subject afflicted with a lower limb musculoskeletal pain comprising the steps of: steps of: securing a device to the subject's foot, whereby the device comprises a foot securing mean, a support member operably attached to the securing mean, and a moveable anterior protuberance and a moveable posterior protuberance; calibrating the posterior protuberance and the anterior protuberance to: (1) a balanced position, the balanced position comprises: a position whereby the device provides a minimal inversion or a minimal eversion to the subject's foot during the stance phases; (2) a minimal lower limb musculoskeletal related pain position; and (3) muscle tuning position; and fixing the posterior protuberance and the anterior protuberance to the support member. Each possibility represents a separate embodiment of the present invention. In another embodiment, the term "minimal" comprises reduced or least.

In another embodiment, provided herein a method of treating a subject afflicted with a lower limb musculoskeletal pain comprising the steps of: steps of: securing a device to the subject's foot, whereby the device comprises a foot securing mean, a support member operably attached to the securing mean, and a moveable anterior protuberance and a moveable posterior protuberance; calibrating the posterior protuberance and the anterior protuberance to: (1) a balanced position, the balanced position comprises: a position whereby the device provides a controlled inversion or a controlled eversion to the subject's foot during the stance phases; (2) a minimal lower limb musculoskeletal related pain position; and (3) a muscle tuning position; and fixing the posterior protuberance and the anterior protuberance to the support member. Each possibility represents a separate embodiment of the present invention.

In another embodiment, lower limb musculoskeletal pain comprises anterior knee pain. In another embodiment, lower limb musculoskeletal pain comprises patella-femoral knee pain. Each possibility represents a separate embodiment of the present invention.

In another embodiment, a lower limb musculoskeletal pain arises from two types of trauma, acute trauma and cumulative (overuse) trauma. In another embodiment, acute traumas occur when the load imposed on the body during a task exceeds the tolerance of the body structures supporting it. In another embodiment, a lower limb musculoskeletal pain is associated with large single loading conditions. In another embodiment, a lower limb musculoskeletal pain is a violent lateral impact on a joint such as but not limited to the knee. In another embodiment, a lower limb musculoskeletal pain is an infrequent extreme force exertion on a joint. In another embodiment, overuse trauma, occurs when the load imposed on the body during a task is not large enough to cause sudden failure of one or other of the underlying body structures (bone, the muscles, tendons and ligaments) but instead these structures are worn down and their tolerance lowered with repeated application of the load. In another embodiment, a lower limb musculoskeletal pain is caused by "wear and tear" on the bodily structures. Each possibility represents a separate embodiment of the present invention.

In another embodiment, a lower limb musculoskeletal pain arises from stress fractures and shin splints. In another embodiment, a lower limb musculoskeletal pain arises from ankle and metacarpal fractures (acute injuries). In another embodiment, a lower limb musculoskeletal pain arises from bursitis. In another embodiment, a lower limb musculoskeletal pain arises from rheumatism. In another embodiment, a lower limb musculoskeletal pain arises from cartilage tear. Each possibility represents a separate embodiment of the present invention.

In another embodiment, a lower limb musculoskeletal pain is a consequence of lower limb osteoarthritis. In another embodiment, a lower limb musculoskeletal pain is a consequence of Piriformis syndrome. In another embodiment, a lower limb musculoskeletal pain is a consequence of Trochanteritis. In another embodiment, a lower limb musculoskeletal pain is sacroiliac pain. In another embodiment, a lower limb musculoskeletal pain causes palpable tenderness of the trochanter major. In another embodiment, a lower limb musculoskeletal pain is caused by hamstring muscle strain. In another embodiment, a lower limb musculoskeletal pain is caused by hamstring injuries. Each possibility represents a separate embodiment of the present invention.

In another embodiment, a lower limb musculoskeletal pain is a direct consequence of bursitis. In another embodiment, a lower limb musculoskeletal pain is a direct consequence of a beat knee (Hyperkeratosis). In another embodiment, a lower limb musculoskeletal pain is a direct consequence of a meniscal lesion. In another embodiment, a lower limb musculoskeletal pain is a direct consequence of meniscal damage. In another embodiment, a lower limb musculoskeletal pain is a direct consequence of a degenerative joint disease. In another embodiment, a lower limb musculoskeletal pain is a direct consequence of a lower limb degenerative joint disease. Each possibility represents a separate embodiment of the present invention.

In another embodiment, a lower limb musculoskeletal pain is a direct consequence of bursitis (Adventitious, prepatellar, etc). In another embodiment, bursitis develops in response to frictional stress that is applied directly over the bursa of the knees. In another embodiment, bursitis is pyogenic bursitis. In another embodiment, a lower limb musculoskeletal pain is associated with tenderness and swelling over the patella. Each possibility represents a separate embodiment of the present invention.

In another embodiment, a lower limb musculoskeletal pain is a direct consequence of meniscal lesions and/or damage. In another embodiment, meniscal lesions/damage usually occurs due to high rates of force being applied to the knee, or heavy rotational force, e.g. when the knee is bent or twisted while bearing load. Each possibility represents a separate embodiment of the present invention.

In another embodiment, a lower limb musculoskeletal pain is a direct consequence of stress fracture/stress reaction injuries. In another embodiment, the term 'stress reaction' refers to bone with evidence of remodeling but with an absence of radiological evidence of fracture. In another embodiment, stress reaction/fracture is the result of repeated micro-injuries to bone, which occur when its maximum strength is exceeded by an applied force and the natural process by which bone adapts to stress is prevented. In another embodiment, stress fracture is associated with the tibia. In another embodiment, stress fracture is associated with the fibula. In another embodiment, stress fracture is associated with the metatarsals. Each possibility represents a separate embodiment of the present invention.

In another embodiment, a lower limb musculoskeletal pain is a direct consequence of a sprained ankle. In another embodiment, a lower limb musculoskeletal pain is a direct consequence of an anterior compartment syndrome. In another embodiment, a lower limb musculoskeletal pain is a direct consequence of a lateral compartment syndrome. In another embodiment, a lower limb musculoskeletal pain is a direct consequence of a plantar fasciitis. In another embodiment, a lower limb musculoskeletal pain is a direct consequence of an Achilles tendonitis. In another embodiment, a lower limb musculoskeletal pain is a direct consequence of a foot corns. In another embodiment, a lower limb musculoskeletal pain is a direct consequence of hallux valgus. In another embodiment, a lower limb musculoskeletal pain is a direct consequence of interdigital neuroma (Morton's neuroma). In another embodiment, a lower limb musculoskeletal pain is a direct consequence of tarsal tunnel syndrome. In another embodiment, a lower limb musculoskeletal pain is a direct consequence of lesser toe deformity. In another embodiment, a lower limb musculoskeletal pain is a direct consequence of psoriatic arthritis. Each possibility represents a separate embodiment of the present invention.

In another embodiment, a lower limb musculoskeletal pain is heel pain. In another embodiment, a lower limb musculoskeletal pain is a direct consequence of an acquired flatfoot. In another embodiment, a lower limb musculoskeletal pain is associated with a putative genesis in abnormal foot pronation. In another embodiment, a lower limb musculoskeletal pain is associated with defective gait patterns. In another embodiment, a lower limb musculoskeletal pain is associated with defective stance. Each possibility represents a separate embodiment of the present invention.

The Subject

In another embodiment, the subject is afflicted with a congenital disorder of joints. In another embodiment, the subject is afflicted with diabetes. In another embodiment, the subject is afflicted with inflammatory diseases (such as Perthes' disease, Lyme disease, a chronic form of arthritis). Each possibility represents a separate embodiment of the present invention.

In another embodiment, the subject is afflicted with rheumatoid arthritis. In another embodiment, the subject is afflicted with Achilles tendon injuries and tendonitis In another embodiment, the subject is afflicted with adductor strain. In another embodiment, the subject is afflicted with an ankle sprain. In another embodiment, the subject is afflicted with anterior cruciate ligament injury. In another embodiment, the subject is afflicted with calcaneal bursitis. In another embodiment, a lower limb musculoskeletal pain is coccyx pain. In another embodiment, the subject is afflicted with compartment syndrome. In another embodiment, the subject is afflicted with iliotibial band syndrome. In another embodiment, the subject is afflicted with medial collateral and lateral collateral ligament injury. In another embodiment, the subject is afflicted with meralgia paraesthetica. In another embodiment, the subject is afflicted with Morton Neuroma. In another embodiment, the subject is afflicted with osteitis pubis. In another embodiment, the subject is afflicted with patellofemoral syndrome. In another embodiment, the subject is afflicted with Pes Anserinus bursitis. In another embodiment, the subject is afflicted with Piriformis syndrome. In another embodiment, the subject is afflicted with plantar fasciitis. In another embodiment, the subject is afflicted with posterior cruciate ligament injury. In another embodiment, the subject is afflicted with prepatellar bursitis. In another embodiment, the subject is afflicted with trochanteric bursitis. Each possibility represents a separate embodiment of the present invention.

In another embodiment, a subject according to the invention further suffers from a gait disorder. In another embodiment, a subject according to the invention is a human subject that can walk or run with a device as described herein. In another embodiment, a subject according to the invention is a human subject that can walk or run with footwear 10. Each possibility represents a separate embodiment of the present invention.

In another embodiment, a gait disorder is asymmetry of gait, shuffling gait, gait with lurching actions, or any combination thereof. In another embodiment, a gait disorder is caused by a degenerative joint disease. Each possibility represents a separate embodiment of the present invention.

Muscle Tuning

In another embodiment, the method as described herein involves exercise with the device as described herein. In another embodiment, exercise is walking or any other form of gait movement. In another embodiment, improvement in measured in a gait lab, EMG, muscle size measurements and other muscle related tests. In another embodiment, improvement in subject's physical state is observed by using the methods described herein. In another embodiment, tuning a muscle is improvement in subject's physiological state. In another embodiment, tuning a muscle is improvement in subject's mental state. In another embodiment, tuning a muscle is improvement in subject's wellbeing. In another embodiment, tuning a muscle is relieving pain such as joint pain. In another embodiment, tuning a muscle is relieving pain such as joint pain. In another embodiment, tuning a muscle is balancing gait. In another embodiment, tuning a muscle is relieving tenderness. In another embodiment, tuning a muscle is relieving stiffness. In another embodiment, tuning a muscle is relieving locking. In another embodiment, tuning a muscle is relieving an effusion. In another embodiment, tuning a muscle is increasing movement. In another embodiment, tuning a muscle is increasing movement secondary to pain. In another embodiment, tuning a muscle is inhibiting regional muscles atrophy. In another embodiment, tuning a muscle is reversing regional muscles atrophy. In another embodiment, tuning a muscle is inducing muscle build-up. In another embodiment, tuning a muscle is inducing differential muscle build-up. Each possibility represents a separate embodiment of the present invention.

In another embodiment, tuning a muscle is improving gait. In another embodiment, tuning a muscle is improving balance. In another embodiment, tuning a muscle is improving impairments of proprioception, balance, strength, or any combination thereof. In another embodiment, tuning a muscle is reversing impairments of proprioception, balance, strength, or any combination thereof. In another embodiment, tuning a muscle is specifically improving impairments of proprioception, balance, strength, or any combination thereof associated with a specific degenerative joint disease. In another embodiment, tuning a muscle is specifically improving impairments of proprioception, balance, strength, or any combination thereof associated with lower extremity arthritis. In another embodiment, tuning a muscle is specifically improving impairments of proprioception, balance, strength, or any combination thereof associated with a hip, an ankle, a foot, or knee osteoarthritis. In another embodiment, tuning a muscle is reducing falls. Each possibility represents a separate embodiment of the present invention.

In another embodiment, tuning a muscle is manipulating a step length. In another embodiment, tuning a muscle is decreasing "step length difference". In another embodiment, tuning a muscle is manipulating single limb support. In another embodiment, tuning a muscle is manipulating out/in toeing angle. In another embodiment, tuning a muscle is calibrating gait cycle (40:40:20). In another embodiment, tuning a muscle is manipulating cadence. In another embodiment, tuning a muscle is manipulating the center of pressure (COP). In another embodiment, tuning a muscle is correcting mean hip motion, knee motion, ankle motion, or any combination thereof in the sagittal plane. In another embodiment, tuning a muscle is improving walking pace or speed. In another embodiment, tuning a muscle is enhancing walking pace or speed. In another embodiment, improving walking pace or speed is reaching a goal of walking speed of 1.6-4 km/hour. In another embodiment, improving walking pace or speed is reaching a goal of walking speed of 1.6-4 km/hour for at least 2 minutes. In another embodiment, improving walking pace or speed is reaching a goal of walking speed of 1.6-4 km/hour for at least 5 minutes. In another embodiment, improving walking pace or speed is reaching a goal of walking speed of 1.6-4 km/hour for at least 10 minutes. In another embodiment, improving walking pace or speed is reaching a goal of walking speed of 1.6-4 km/hour for at least 15 minutes. In another embodiment, improving walking pace or speed is reaching a goal of walking speed of 2-3.5 km/hour for at least 2 minutes. In another embodiment, improving walking pace or speed is reaching a goal of walking speed of 2-3.5 km/hour for at least 5 minutes. In another embodiment, improving walking pace or speed is reaching a goal of walking speed of 2-3.5 km/hour for at least 10 minutes. In another embodiment, improving walking pace or speed is reaching a goal of walking speed of 2-3.5 km/hour for at least 15 minutes. In another embodiment, improving walking pace or speed is reaching a goal of walking speed of 2.5-3.2 km/hour for at least 2 minutes. In another embodiment, improving walking pace or speed is reaching a goal of walking speed of 2.5-3.2 km/hour for at least 5 minutes. In another embodiment, improving walking pace or speed is reaching a goal of walking speed of 2.5-3.2 km/hour for at least 10 minutes. In another embodiment, improving walking pace or speed is reaching a goal of walking speed of 2.5-3.2 km/hour for at least 15 minutes. Each possibility represents a separate embodiment of the present invention.

In another embodiment, tuning a muscle is relaxing a stiff knee, hip, ankle, or foot. In another embodiment, tuning a muscle is correcting an abnormal flexion in stance phase. In another embodiment, tuning a muscle is correcting a restriction of hip extension in toe-off. In another embodiment, tuning a muscle is correcting an abnormal muscle activity of the lower limb. In another embodiment, tuning a muscle is correcting overactivity of rectus femoris in stance. In another embodiment, tuning a muscle is correcting (shortening or lengthening) semitendinosus activity. In another embodiment, tuning a muscle is correcting exaggerated triceps surae activity in pre-swing. In another embodiment, tuning a muscle is correcting a silent tibialis anterior in terminal swing. Each possibility represents a separate embodiment of the present invention.

In another embodiment, the methods as described herein further comprises a combination treatment comprising the use of the device as described herein and a proper medication. In another embodiment, one of skill in the art will readily diagnose and prescribe the proper medication to a subject suffering from a disease or a condition such as described herein. In another embodiment, the medication is an analgesic such as acetaminophen. In another embodiment, the medication is a non-steroidal anti-inflammatory drug (NSAID) such as ibuprofen. In another embodiment, the medication is a COX-2 selective inhibitor such as celecoxib. In another embodiment, the medication is a topical NSAID such as diclofenac. In another embodiment, the medication is an opioid analgesic such as morphine or codeine. In another embodiment, the medication is a glucocorticoid such as hydrocortisone. In another embodiment, the medication is topical capsaicin. In another embodiment, the medication is a joint injection of hyaluronic acid. Each possibility represents a separate embodiment of the present invention.

In another embodiment, the outcome of treatment as provided herein is apparent immediately after the initial use of the device as described herein. In another embodiment, the outcome of treatment as provided herein is apparent after 10-1000000 meters of walking with the device as described herein. In another embodiment, the outcome of treatment as provided herein is apparent after 50-100000 meters of walking with the device as described herein. In another embodiment, the outcome of treatment as provided herein is apparent after 500-10000 meters of walking with the device as described herein. In another embodiment, the outcome of treatment as provided herein is apparent after 500-5000 meters of walking with the device as described herein. In another embodiment, the outcome of treatment as provided herein is apparent after 500-3000 meters of walking with the device as described herein. Each possibility represents a separate embodiment of the present invention.

In another embodiment, the outcome of treatment as provided herein is correction of a pathology related to lower limb osteoarthritis. In another embodiment, the outcome of treatment as provided herein is correction of a hip, an ankle, a foot, or a knee osteoarthritis. In another embodiment, the outcome of treatment as provided herein is alleviating lower limb osteoarthritis. In another embodiment, the outcome of treatment as provided herein is inhibiting symptoms associated with lower limb osteoarthritis. Each possibility represents a separate embodiment of the present invention.

In another embodiment, the outcome of treatment as provided herein is apparent while the subject is wearing the device as described herein. In another embodiment, the outcome of treatment as provided herein is apparent also when the subject is walking barefoot. In another embodiment, the outcome of treatment as provided herein is apparent also when the subject is wearing walking shoes. In another embodiment, the outcome of treatment as provided herein is apparent also when the subject is wearing work shoes (including but not limited to elegant shoes). Each possibility represents a separate embodiment of the present invention.

In another embodiment, differential muscle build-up comprises inducing muscle build-up in regions of muscles atrophy. In another embodiment, differential muscle build-up comprises inducing muscle build-up in regions of muscles weakness. In another embodiment, differential muscle build-up comprises inducing muscle build-up in regions of muscles injury. Each possibility represents a separate embodiment of the present invention.

In another embodiment, a device as disclosed herein has an immediate effect with regard to treating or treatment of a disease, a pathology, and/or pain as provided herein. In another embodiment, short term immediate effect is apparent in a barefoot subject after walking with the device for 1-5 minutes. In another embodiment, a device as disclosed herein has an immediate effect with regard to treating or treatment of a disease, a pathology, and/or pain as provided herein. In another embodiment, short term immediate effect is apparent in a barefoot subject after walking with the device for 10-60 minutes. In another embodiment, short term immediate effect is apparent in a barefoot subject after walking with the device for 30-600 minutes. In another embodiment, short term immediate effect is apparent in a barefoot subject after walking with the device for 1-10 hours (hrs). In another embodiment, short term immediate effect is apparent in a barefoot subject after walking with the device for 5-1000 hours (hrs). In another embodiment, short term immediate effect is apparent in a barefoot subject after walking with the device for 12-96 hours (hrs). In another embodiment, short term immediate effect is apparent in a barefoot subject after walking with the device for 1-10 days. In another embodiment, short term immediate effect is apparent in a barefoot subject after walking with the device for 7-21 days. In another embodiment, short term immediate effect is apparent in a barefoot subject after walking with the device for 5-30 days. Each possibility represents a separate embodiment of the present invention.

In another embodiment, the effect is apparent in a barefoot subject after walking with the device for 1-2 months. In another embodiment, the effect is apparent in a barefoot subject after walking with the device for 1-24 months. In another embodiment, the effect is apparent in a barefoot subject after walking with the device for 2-6 months. In another embodiment, the effect is apparent in a barefoot subject after walking with the device for 4-10 months. In another embodiment, the effect is apparent in a barefoot subject after walking with the device for 6-48 months. In another embodiment, the effect is apparent in a barefoot subject after walking with the device for 12-24 months. In another embodiment, the effect is apparent in a barefoot subject after walking with the device for 10-30 months. Each possibility represents a separate embodiment of the present invention.

In another embodiment, tuning a muscle comprises treating which is a process wherein the subject's disease or condition is ameliorated. In another embodiment, tuning a muscle is improvement over time. In another embodiment, tuning a muscle is continuous improvement over time. In another embodiment, progress or improvement is reduction in any measure provided herein. In another embodiment, progress or improvement is measured in a gait lab. In another embodiment, progress or improvement is measured by radiological methods. In another embodiment, radiological methods for measuring progress, treatment and/or improvement are known to one of skill in the art (such as but not limited to: X-ray, MRI, etc.). In another embodiment, progress or improvement is measured by a pain questionnaire. In another embodiment, progress or improvement is measured by physical examination that includes examining a range of motions such as but not limited to: flexion, extension, dorsi/plantar flexion (ankle), muscular circumference, internal/external rotation (hip) abduction/adduction (hip and knee), effusion, hot/warm knee, or any combination thereof. Each possibility represents a separate embodiment of the present invention.

In another embodiment, progress or improvement is measured in a gait lab and includes measuring velocity, step length increase, step length difference (symmetry), single limb support (aim at reaching 40%), single limb support difference (symmetry), double limb support, in-toeing/out-toeing, flexion/extension, range of motion (ROM), flexion/extension, or any combination thereof. Each possibility represents a separate embodiment of the present invention.

In another embodiment, a device as described herein is prescribed to a subject according to the subject's physical condition. In another embodiment, a device as described herein is prescribed to a subject according to the subject's medical condition. In another embodiment, a device as described herein is prescribed to a subject according to the subject's medical history. In another embodiment, prescription includes directions of how to use the device. In another embodiment, prescription includes intensity of use, daily use, or daily distance directions.

In another embodiment, any prescription as described herein comprises increase in daily usage time as the subject's gait improves. In another embodiment, any prescription as described herein comprises increase in daily usage time as subject's pain decreases. In another embodiment, any prescription as described herein comprises increase in daily usage time as subject's disease or condition as described herein, improves. In another embodiment, a prescription as described herein further comprises medicating the subject according to his or hers medical condition. Each possibility represents a separate embodiment of the present invention.

In another embodiment, a prescription as described herein further comprises adjustments of the device as subject's lower limb muscles are tuned or are off balance. In another embodiment, adjustments of the device comprise calibrating or positioning a protuberance as described herein. Each possibility represents a separate embodiment of the present invention.

The Device

In another embodiment, the device is secured to a subject's foot directly. In another embodiment, the term "secured to a subject's foot" comprises securing the device to any footwear such as but not limited to shoes, boots, etc that are secured to a subject's foot. In another embodiment, a foot securing means secures the device such as footwear 10 to a subject's foot. In another embodiment, various different feet securing means can be used. In another embodiment, a foot securing mean comprises a plurality of securing means. In another embodiment, a foot securing mean is a lace. In another embodiment, a foot securing mean comprises a Velcro fastener. In another embodiment, a foot securing mean comprises securing straps. In another embodiment, reference is made to FIGS. 1-4, which illustrate footwear 10 constructed and operative in accordance with an embodiment of the present invention. Each possibility represents a separate embodiment of the present invention.

In another embodiment, a support member is operably attached to the securing mean. In another embodiment, operably attached comprises sufficient attachment between the securing mean and the support member. In another embodiment, a support member comprises the sole. In another embodiment, a support member comprises the inner sole. In another embodiment, a support member comprises the outer sole. In another embodiment, a support member comprises the middle sole. In another embodiment, a support member comprises the upper (the part of the shoe that is on top of the foot). In another embodiment, the upper is operably attached to the securing mean (such as but not limited to laces). In another embodiment, the upper comprises straps or totally enclosing the foot). In another embodiment, the upper comprises straps that function as securing means (such as sandals). Each possibility represents a separate embodiment of the present invention.

In another embodiment, a device such as footwear 10 is supplied as one or more pairs of shoe-like devices, or alternatively, as just one of the shoe-like devices. In another embodiment, footwear 10 comprises a support member 12 having a periphery in a shape of a shoe sole comprising an upper surface 14. In the illustrated embodiment, the upper surface 14 is indented with a peripheral ridge 16, but it is appreciated that other configurations of upper surface 14 are within the scope of the invention. In another embodiment, footwear 10 is attached to a foot of a user by means of a boot 18 and/or fasteners 20, such as but not limited to, VELCRO straps, buckles, shoe laces, and the like. In another embodiment, footwear 10 is attached to a foot of a user by means of a shoe. In another embodiment, a shoe comprises a platform of a sneaker. In another embodiment, the term sneaker comprises a boot. In another embodiment, the term sneaker comprises a walking boot. In another embodiment, a shoe comprises a platform of a running shoe. In another embodiment, a shoe comprises a platform of an elegant shoe. In another embodiment, a shoe comprises a platform of a walking shoe or boot. Each possibility represents a separate embodiment of the present invention.

In another embodiment, a device such as but not limited to boot 18 is fashioned for attachment to the user's foot with or without fasteners 20. In another embodiment, fasteners 20 are used as foot securing means to attach footwear 10 to the user's foot without boot 18. Each possibility represents a separate embodiment of the present invention.
BP
In another embodiment, the invention provides that the device such as footwear 10 comprises protuberances in a fixed position. In another embodiment, the invention provides that the device such as footwear 10 comprises protuberances having any shape known to one of skill in the art. In another embodiment, the invention provides that the device comprises at least two bulbous protuberances. In another embodiment, a protuberance is symmetrical. In another embodiment, a protuberance is asymmetrical. In another embodiment, a protuberance comprises a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In another embodiment, each protuberance 22 has a curved outer contour 26. In another embodiment, each protuberance has a different curved outer contour. In another embodiment, each protuberance 22 has a convexity.

In another embodiment, a protuberance comprises a dome shape. In another embodiment, a protuberance as described herein comprises a dome shape which further comprises multiple different convexities. In another embodiment, each protuberance 22 comprises a different convexity. In another embodiment, each protuberance 22 comprises a different set of convexities. The cross-section of the contour 26, that is, either the cross-section taken with respect to a longitudinal axis 28 (FIG. 4) of support member 12 (corresponding to the shape seen in FIG. 2) or the cross-section taken with respect to a latitudinal axis 30 (FIG. 4) of support member 12 (corresponding to the shape seen in FIG. 3), or any other cross-section, may have any curvilinear shape. Each possibility represents a separate embodiment of the present invention.

In another embodiment, the contours 26 may have the shape of a conic section, that is, the shape of a circle, ellipse, parabola or hyperbola. The various cross-sections of the contours 26 of protuberance 22 may be shaped identically or differently. In another embodiment, the shape of a protuberance is defined by equal arches. In another embodiment, the shape of a protuberance is defined by a variety of arches of different radiuses which are tangent to each other. In another embodiment, the shape of a protuberance is symmetrical. In another embodiment, the shape of a protuberance is asymmetrical. In another embodiment, a protuberance is a bulbous protuberance. Each possibility represents a separate embodiment of the present invention.

In another embodiment, the invention provides that the device such as footwear 10 supports the foot of a subject only by the two protuberances when the two protuberances are placed on a ground surface. In another embodiment, the invention provides that the device such as footwear 10 supports the foot of a subject during stance only by the two protuberances when the two protuberances are placed on a ground surface. In another embodiment, the invention provides that during stance only the 2 ground engaging surfaces of the protuberances (such as the peak or the surface facing the ground) are in contact with a ground surface. In another embodiment, the invention provides that during stance only the ground engaging surface in each protuberance is in contact with a ground surface. Each possibility represents a separate embodiment of the present invention.

In another embodiment, at least two bulbous protuberances 22 protrude from a lower surface 24 of support member 12. In another embodiment, only two bulbous protuberances 22 protrude from a lower surface 24 of support member 12. In another embodiment, a lower surface of support member is an outsole. In another embodiment, only two bulbous protuberances 22 protrude from a lower surface 24 of support member 12.

In another embodiment, the ground engaging parts of the device are only the protuberances. In another embodiment, during all phases of gait including the stance phase the protuberances are the only parts of the device which are ground engaging. In another embodiment, during all phases of gait including the stance phase the protuberances 22 are the only parts of the device which are in direct contact with the ground. Each possibility represents a separate embodiment of the present invention.

In another embodiment, a protuberance as described herein is movable. In another embodiment, a protuberance as described herein is fixed. In another embodiment, a protuberance as described herein is mountable. In another embodiment, a protuberance as described herein is replaceable. In another embodiment, a protuberance as described herein is movable along the outer surface of the support member. In another embodiment, a protuberance as described herein is movable along the outer surface of the outsole. In another embodiment, a protuberance as described herein can be positioned within the outer surface of the support member. Each possibility represents a separate embodiment of the present invention.

In another embodiment, a protuberance as described herein is movable or translatable such as in a track (e.g., forwards, backwards, sideways or diagonally) and/or rotatable about its own or other axis, or a combination of such motions. Each possibility represents a separate embodiment of the present invention.

In another embodiment, a protuberance is movable within a predefined area. In another embodiment, a protuberance is movable within an area of 1 $cm^2$ to 18 $cm^2$. In another embodiment, a protuberance is movable within an area of 1 $cm^2$ to 6 $cm^2$. In another embodiment, a protuberance is movable within an area of 1 $cm^2$ to 4 $cm^2$. In another embodiment, a protuberance is movable within an area of 2 $cm^2$ to 8 $cm^2$. In another embodiment, a protuberance is movable within an area of 3 $cm^2$ to 6 $cm^2$. In another embodiment, a protuberance is movable within an area of 4 $cm^2$ to 10 $cm^2$. In another embodiment, a protuberance is movable within an area of 5 $cm^2$ to 18 $cm^2$. In another embodiment, a protuberance is movable within an area of 4 cm² to 12 cm². Each possibility represents a separate embodiment of the present invention.

In another embodiment, a predefined area is a circle. In another embodiment, a predefined area is a square. In another embodiment, a predefined area is an ellipse. In another embodiment, a predefined area is a rectangle. In another embodiment, a predefined area is quadrangular. In another embodiment, a predefined area comprises any shape known to one of skill in the art. In another embodiment, a predefined area is shapeless. Each possibility represents a separate embodiment of the present invention.

In another embodiment, a protuberance can be positioned anywhere on the support member. In another embodiment, a protuberance can be fixed anywhere on the support member. In another embodiment, a protuberance can be positioned and/or fixed anywhere within a predefined area. In another embodiment, the protuberance is hooked to a rail. In another embodiment, the protuberance is connected to a rail. In another embodiment, the protuberance is connected to a rail and is movable along the rail. In another embodiment, the protuberance is connected to a rail, is movable along the rail, and can be positioned and/or fixed anywhere along the rail. Each possibility represents a separate embodiment of the present invention.

In another embodiment, a protuberance is slidingly mounted on support member. In another embodiment, a protuberance is mounted on a track 36 (FIG. 2) formed in the lower surface 24 of support member 12, and is selectively positioned anywhere along the track and fastened and or fixed thereto. In another embodiment, track 36 extends along a portion of the shoe sole or all along the length of the shoe sole. Alternatively or additionally, the amount of protrusion of a protuberance is adjusted, such as by mounting protuberance with a threaded fastener 38 (FIG. 3) to support member 12 and tightening or releasing threaded fastener. In another embodiment, the term "fastening", "fixing" and "securing" are used interchangeably. Each possibility represents a separate embodiment of the present invention.

Figure 3:
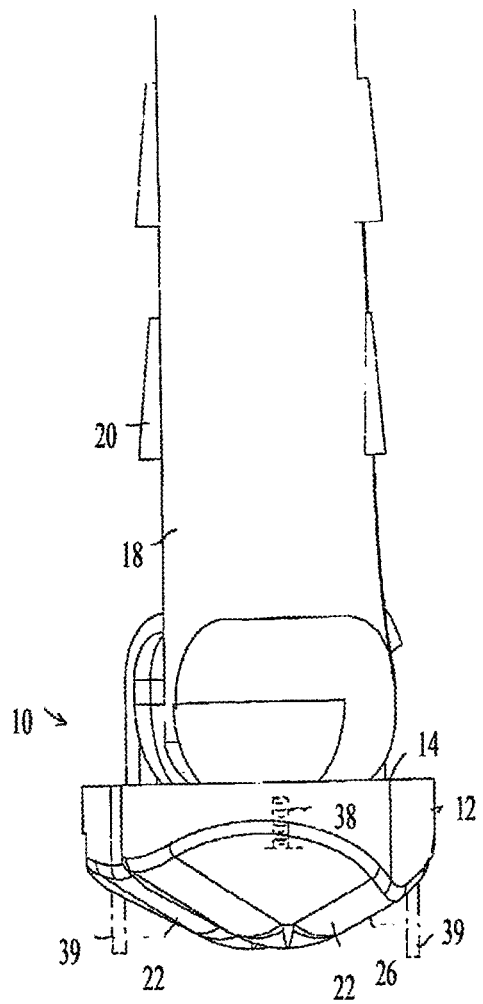

In another embodiment, a device as described herein further comprises an additional bulbous protuberance or bulbous protuberances, non-bulbous protuberance 39, or non-bulbous protuberances shown in FIG. 3. In another embodiment, protuberances 39 are formed in the shape of a peg, stud, bolt, pin, dowel and the like, although the invention is not limited to these shapes. In another embodiment, protuberances 39 may be rigid or flexible. In another embodiment, protuberances 39 are of different resilience or hardness, such as having different elasticity properties or Shore hardness. In another embodiment, protuberances 39 protrude by different amounts from the lower surface 24 of support member 12. In another embodiment, the amount of protrusion of protuberances 39 or height is adjusted. In another embodiment, protuberance 39 is fixed or movable at any place on the lower surface 24 of support member 12 Each possibility represents a separate embodiment of the present invention.

In another embodiment, a protuberance is slidingly mounted on support member 12. In another embodiment, a device such as footwear 10 comprises a sliding/shifting mechanism for a protuberance inside the sole of footwear 10. In another embodiment, the sliding/shifting mechanism comprises, without limitation, a mechanism that floats in a viscous matrix (e.g., fluid in a chamber formed in the sole), that is suspended by inner cables, or a niche trapping a protuberance with a fixing mean. Each possibility represents a separate embodiment of the present invention.

Fixing a BP

Figure 2:
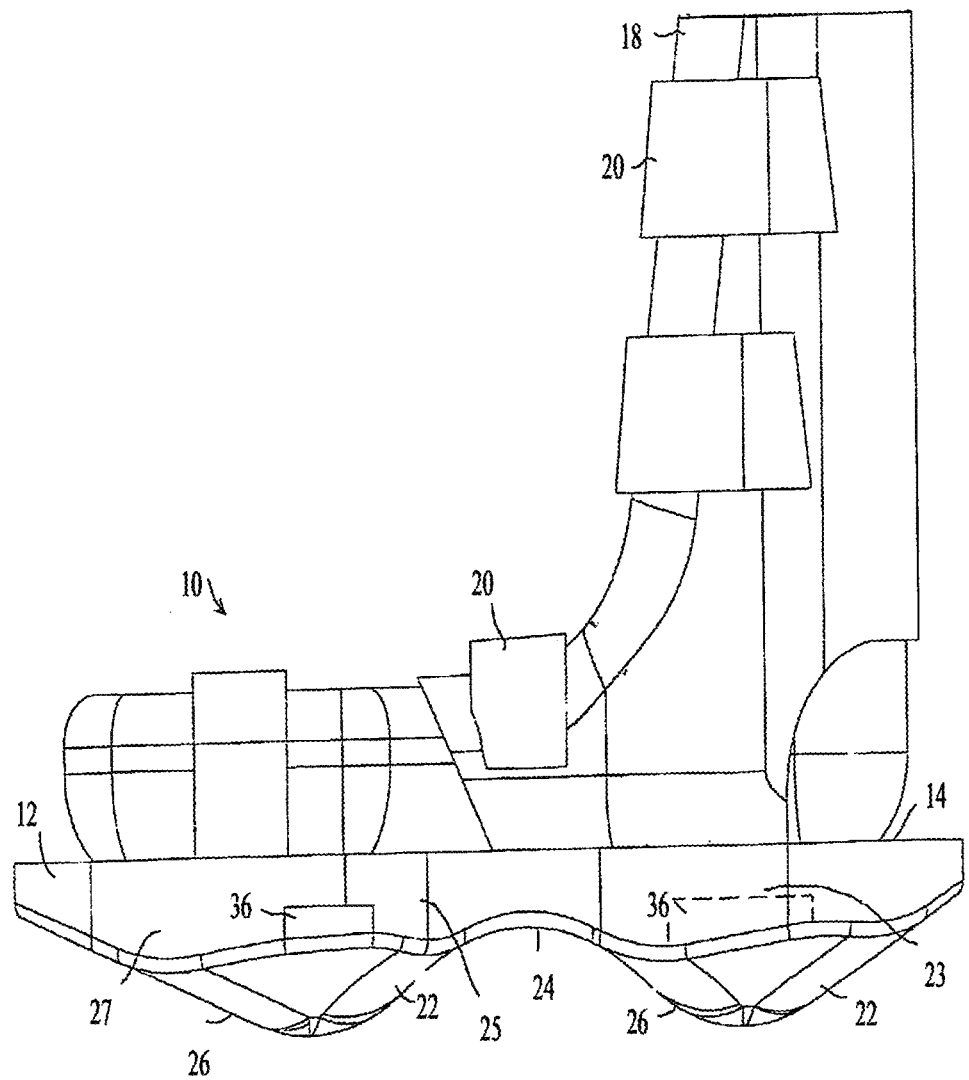
FIGS. 2 and 3 are simplified side-view and rear-view illustrations, respectively, of the footwear of FIG. 1.

As seen clearly in FIG. 2, one protuberance 22 may be positioned more posteriorly than the other protuberance 22. In another embodiment, a device as described herein comprises at least one anterior protuberance. In another embodiment, a device as described herein comprises at least one posterior protuberance. In another embodiment, the device consists one anterior protuberance and one posterior protuberance. In another embodiment, the device comprises at least one anterior protuberance and one moveable posterior protuberance. In another embodiment, the device comprises at least one moveable anterior protuberance and one posterior protuberance. In another embodiment, the device comprises at least one moveable anterior protuberance and one moveable posterior protuberance. In another embodiment, the device consists one moveable anterior protuberance and one moveable posterior protuberance. Each possibility represents a separate embodiment of the present invention.

In another embodiment, the protuberances rise vertically and therefore each protuberance comprises a base end and a peak end. In another embodiment, the surface area of the base is larger than the surface area of the peak. In another embodiment, the peak is the ground engaging portion of a protuberance in the stance phase. In another embodiment, the peak is the ground engaging portion of a protuberance in all gait phases. Each possibility represents a separate embodiment of the present, invention.

In another embodiment, a protuberance such as a bulbous protuberance 22 protrudes from the upper surface 14 of support member 12.

Positions of BPs

Reference is now made, in one embodiment, to FIGS. 1-4, which illustrate footwear 10 constructed and operative in accordance with an embodiment of the present invention. Footwear 10, in one embodiment, is supplied as one or more pairs of shoe-like devices, or alternatively, as just one of the shoe-like devices. In another embodiment, a shoe-like device comprises a shoe platform and protuberances. Footwear 10, in one embodiment, is designed to adapt on a shoe such as Footwear 10. Footwear 10, in one embodiment, is a sandal or sandal-like footwear. In another embodiment, the shoe platform is a boot. In another embodiment, the shoe platform resembles a hiking boot. Each possibility represents a separate embodiment of the present invention. Each possibility represents a separate embodiment of the present invention.

In another embodiment, the footwear 10 comprises a support member 12 having a periphery in a shape of a shoe sole with an upper surface 14. In another embodiment, the footwear 10 comprises an insole placed on top of the upper surface 14. In another embodiment, the insole is the interior bottom of footwear 10. In another embodiment, the insole sits directly beneath the foot. In another embodiment, the insole is removable, replaceable, or both. In another embodiment, the insole adds comfort, control the shape, moisture, smell, or any combination thereof. In another embodiment, the insole is placed to correct defects in the natural shape of the foot or positioning of the foot during standing or walking Each possibility represents a separate embodiment of the present invention.

In another embodiment, a support member 12 comprises an outsole. In another embodiment, a support member 12 comprises lower surface 24 or an outsole of support member 12. In another embodiment, lower surface 24 or an outsole is made of natural rubber or a synthetic imitation. In another embodiment, lower surface 24 or an outsole comprises a single piece, or may comprise separate pieces of different materials. In another embodiment, lower surface 24 or an outsole can be softer or harder. In another embodiment, a support member 12 further comprises a midsole which is a layer in between the outsole and the insole the most pressure down. In another embodiment, a support member 12 does not have a midsole. Each possibility represents a separate embodiment of the present invention.

In another embodiment, positioning at least a first bulbous protuberance and a second bulbous protuberance in a balanced position is the position in which the footwear exerts the least valgus, varus, dorsal or plantar torque about the ankle in a subject being examined. In another embodiment, positioning at least a first bulbous protuberance and a second bulbous protuberance in a balanced position is the position in which the footwear provides the least or minimal lower limbs muscle activity. In another embodiment, positioning at least a first bulbous protuberance and a second bulbous protuberance in a balanced position is the position in which the footwear provides balanced lower limbs muscle activity. In another embodiment, positioning at least a first bulbous protuberance and a second bulbous protuberance in a balanced position is toning lower limb muscles. In another embodiment, positioning at least a first bulbous protuberance and a second bulbous protuberance in a balanced position is toning the amount of tension or resistance to movement in a muscle involved in gait. In another embodiment, positioning at least a first bulbous protuberance and a second bulbous protuberance in a balanced position is lower limb unloading that allows maximal ankle, knee, and hip joint mobility. In another embodiment, positioning at least a first bulbous protuberance and a second bulbous protuberance in a balanced position is providing a reduction of muscle activity, larger passive ankle excursion, improved gait ability, or any combination thereof. In another embodiment, positioning at least a first bulbous protuberance and a second bulbous protuberance in a balanced position is increasing step length, stance symmetry, or a combination thereof. In another embodiment, positioning at least a first bulbous protuberance and a second bulbous protuberance in a balanced position is increasing the length of the force point of action in lower limb muscles such as but not limited to: soleus, tibialis posterior, and both gastrocnemius muscles. In another embodiment, positioning at least a first bulbous protuberance and a second bulbous protuberance in a balanced position is toning the plantar flexors, dorsi-flexors, invertors and/or evertors. In another embodiment, positioning at least a first bulbous protuberance and a second bulbous protuberance in a balanced position is preventing excessive forward rotation as the body moves forward over the stationary foot. In another embodiment, positioning at least a first bulbous protuberance and a second bulbous protuberance in a balanced position is toning the heel off of the heel. Each possibility represents a separate embodiment of the present invention. Each possibility represents a separate embodiment of the present invention.

Figure 4:
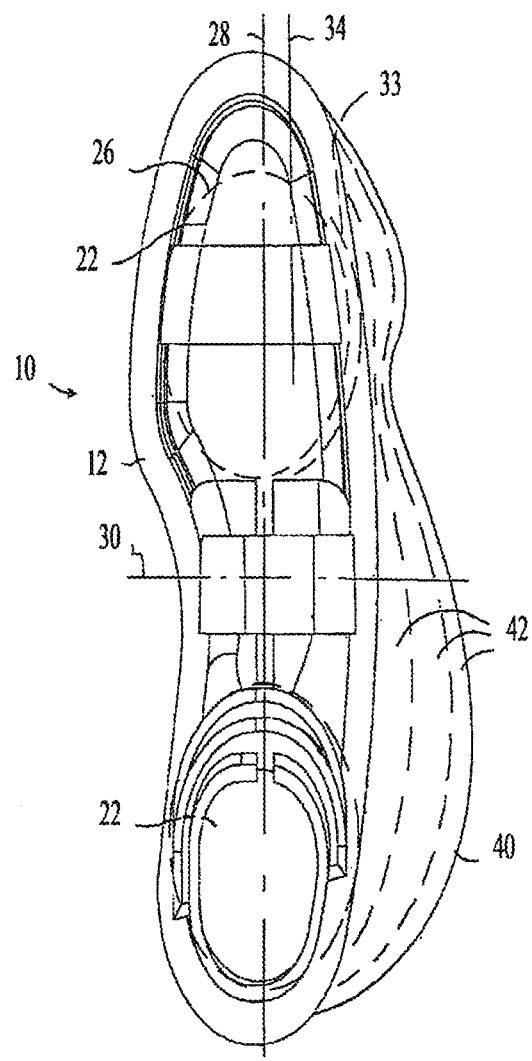
FIG. 4 is a simplified top-view illustration of the footwear of FIG. 1, showing further features of other embodiments of the present invention.

In another embodiment, as seen in FIG. 4, the protuberances are positioned on a common longitudinal axis of support member 12, such as the centerline 28 of support member 12. In another embodiment, the protuberances are positioned on opposite sides of the latitudinal midline 30. In another embodiment, the protuberances are positioned offset from the centerline 28 of support member 12, and on opposite sides of the latitudinal midline 30. In another embodiment, the bases of the protuberances are positioned on the centerline of the support member. In another embodiment, the peaks of the protuberances are positioned on opposite sides of the centerline of support member. Each possibility represents a separate embodiment of the present invention. In some embodiments, the meaning of "protuberance is positioned offset from the centerline" comprises that the peak or the ground engaging surface of a protuberances is positioned offset from the centerline. In some embodiments, the meaning of "protuberance is positioned offset from the centerline" comprises that only the peak or the ground engaging surface of a protuberance is positioned offset from the centerline but the centerline still crosses the protuberance.

In another embodiment, the peak or the ground engaging surface of the anterior protuberance is positioned laterally from the centerline of the support member. In another embodiment, the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is aligned with centerline. In another embodiment, the peak or the ground engaging surface of the anterior protuberance is positioned medially from the centerline of the support member and the peak or the ground engaging surface of the posterior protuberance is aligned with centerline. Each possibility represents a separate embodiment of the present invention.

In another embodiment, the peak or the ground engaging surface of the posterior protuberance is positioned laterally from the centerline of the support member. In another embodiment, the peak or the ground engaging surface of the posterior protuberance is positioned medially from the centerline of the support member. In another embodiment, the peak or the ground engaging surface of the posterior protuberance is positioned laterally from the centerline of the support member and the peak or the ground engaging surface of the anterior protuberance is aligned with centerline. In another embodiment, the peak or the ground engaging surface of the posterior protuberance is positioned medially from the centerline of the support member and the peak or the ground engaging surface of the anterior protuberance is aligned with centerline. Each possibility represents a separate embodiment of the present invention.

In another embodiment, the peak or the ground engaging surface of the posterior protuberance is positioned laterally from the centerline of the support member and the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is positioned medially from the centerline of the support member. Each possibility represents a separate embodiment of the present invention.

Figure 5:
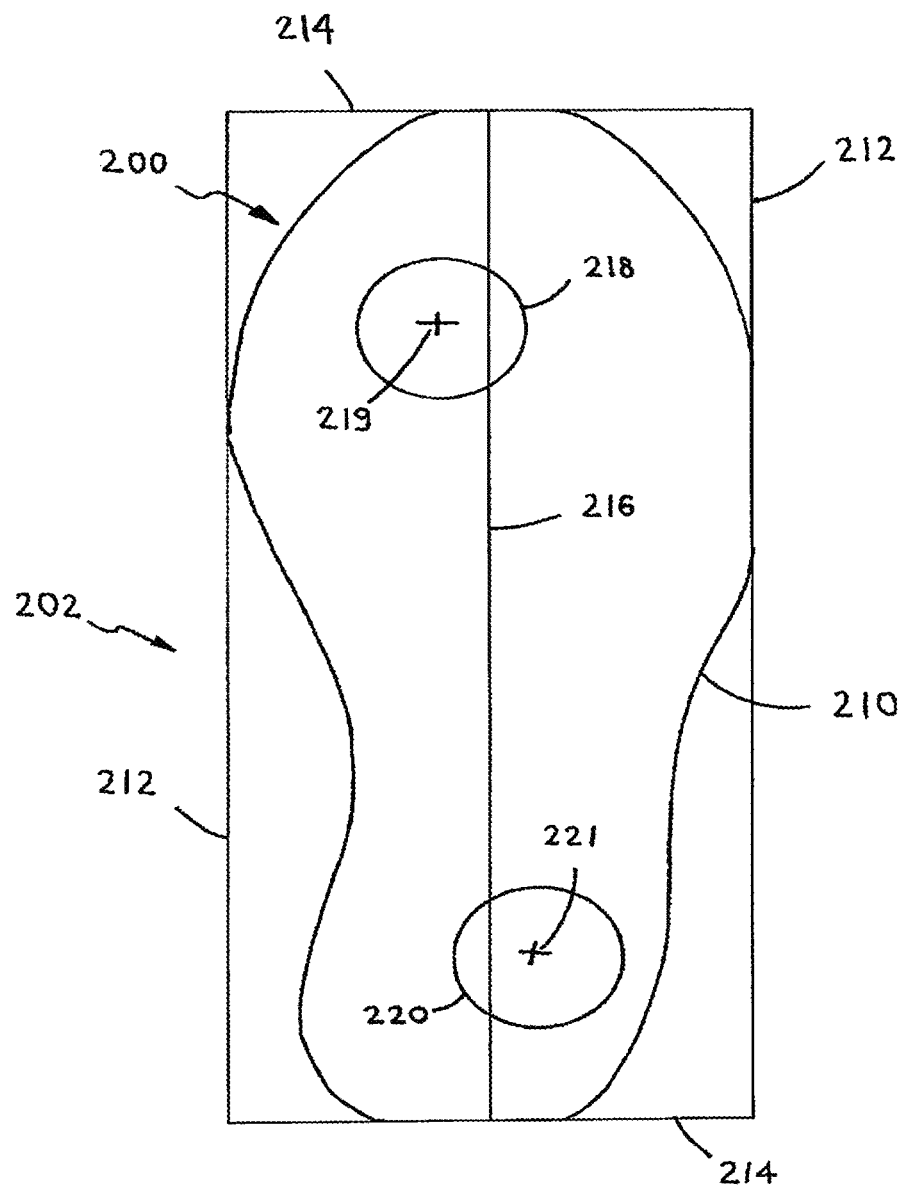
FIG. 5 is a simplified pictorial illustration of an alignment of the anterior (forward) and posterior (rearward) protuberances on a support member, according to embodiments of the present invention.
Figure 6:
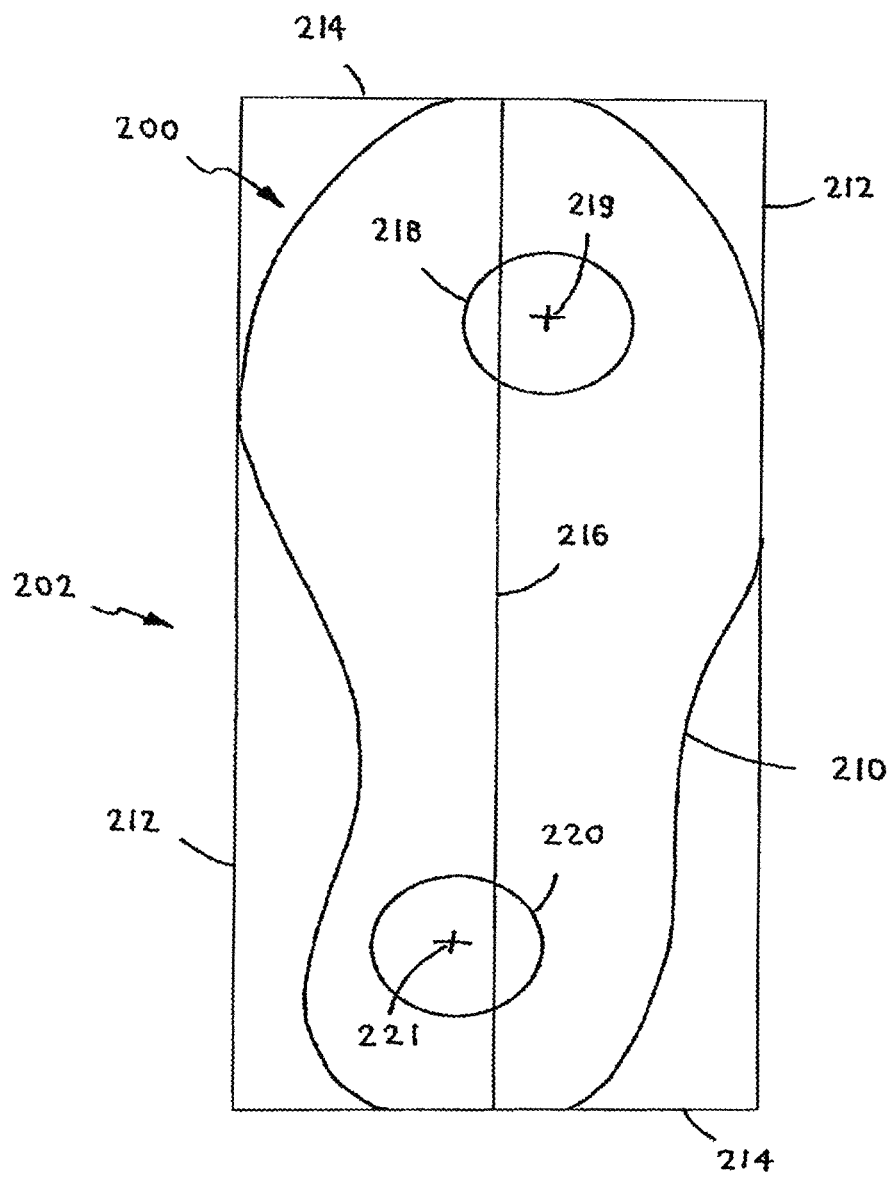
FIG. 6 is a simplified pictorial illustration of another alignment of the anterior and posterior protuberances on a support member, according to embodiments of the present invention.

In another embodiment, the centerline divides longitudinally the calcaneus support portion into two equal halves and further extends towards the phalanges and metatarsals support portion in a straight line. In another embodiment, the centerline divides longitudinally the arch of the calcaneus support portion into two equal halves and further extends towards the phalanges and metatarsals support portion in a straight line. In another embodiment, the centerline divides longitudinally the proximal arch of the calcaneus support portion into two equal halves and further extends towards the phalanges and metatarsals support portion in a straight line. In another embodiment, the centerline divides longitudinally the support portion as seen in FIGS. 5-6 of the calcaneus support portion into two equal halves and further extends towards the phalanges and metatarsals support portion in a straight line. In another embodiment of the present invention, the longitudinal centerline is defined as a longitudinal straight line connecting middles of the short sides of a rectangle which delimits a contour of the support member. Each possibility represents a separate embodiment of the present invention.

In another embodiment, the bases of the protuberances are positioned on the centerline of the support member and the peaks of the protuberances are positioned on opposite sides of the centerline of support member. In another embodiment, the bases of the protuberances are positioned on the centerline of the support member but the peaks of the protuberances are offset from the centerline of the support member. In another embodiment, the bases of the protuberances are positioned on the centerline of the support member but the peaks of the protuberances are positioned on opposite sides of the centerline of the support member. In another embodiment, positioning a protuberance is positioning the peak or the ground engaging surface of a protuberance. In another embodiment, the terms "peak" and "ground engaging surface" are used interchangeably. Each possibility represents a separate embodiment of the present invention.

In another embodiment, the anterior protuberance is positioned medially from the centerline of the support member. In another embodiment, the peak of the anterior protuberance is positioned medially from the centerline of the support member. In another embodiment, the base of the anterior protuberance is position on the centerline of the support member but the peak of the anterior protuberance is positioned medially from the centerline of the support member. In another embodiment, the anterior protuberance is positioned laterally from the centerline of the support member. In another embodiment, the peak of the anterior protuberance is positioned laterally from the centerline of the support member. In another embodiment, the base of the anterior protuberance is positioned on the centerline of the support member but the peak of the anterior protuberance is positioned laterally from the centerline of the support member. In another embodiment, the posterior protuberance is positioned medially from the centerline of the support member. In another embodiment, the peak of the posterior protuberance is positioned medially from the centerline of the support member. In another embodiment, the base of the posterior protuberance is positioned on the centerline of the support member but the peak of the posterior protuberance is positioned medially from the centerline of the support member. In another embodiment, the posterior protuberance is positioned laterally from the centerline of the support member. In another embodiment, the peak of the posterior protuberance is positioned laterally from the centerline of the support member. In another embodiment, the base of the posterior protuberance is position on the centerline of the support member but the peak of the posterior protuberance is positioned laterally from the centerline of the support member.

In another embodiment, as seen in FIG. 2, the posterior protuberance 22P is positioned generally underneath a calcaneus (heel, ankle) support portion 23 of support member 12. In another embodiment, the anterior protuberance 22A may be positioned generally underneath a metatarsals support portion 25 and/or phalanges support portion 27 of support member 12. Each possibility represents a separate embodiment of the present invention.

In another embodiment, as indicated by broken lines 33 in FIG. 4, the anterior protuberances 22A is aligned on a longitudinal axis with its peak offset from centerline 28, and the posterior protuberance 22P is also is aligned on a longitudinal axis with its peak offset from centerline 28 but to the opposite direction of 22A with respect to centerline 28. Each possibility represents a separate embodiment of the present invention.

Figure 12:
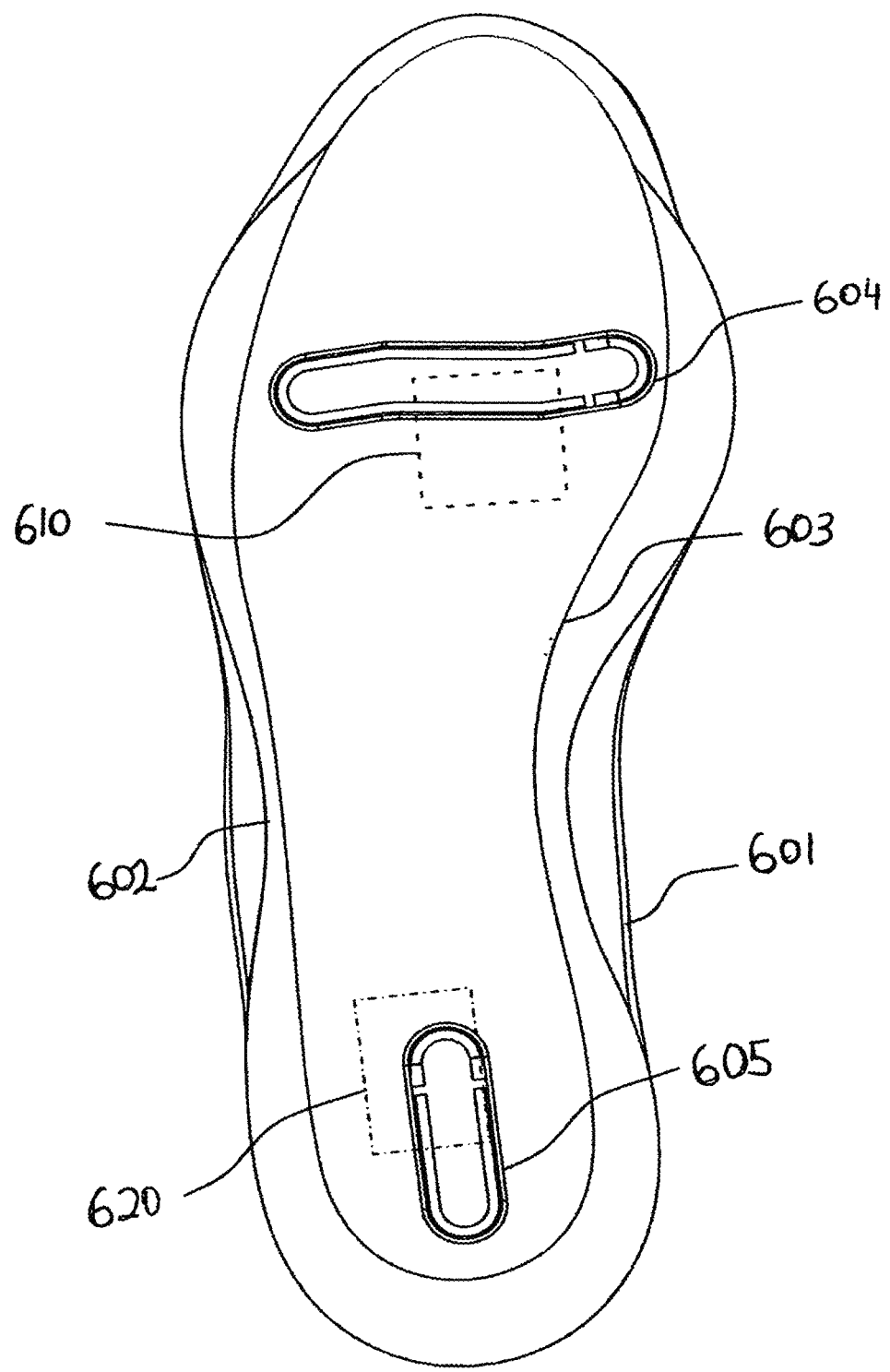
FIG. 12 illustrates effective area boundaries of positioning of the anterior and posterior protuberances with respect to a support surface, according to certain diseases of the present invention.

In another embodiment, FIG. 5 is a simplified pictorial illustration of an alignment of the anterior (forward) and posterior (rearward) protuberances on a support member 200, according to embodiments of the present invention. Centerline 216, in the embodiment shown in FIG. 12 is defined as a longitudinal straight line (median) that connects the middles of short sides 214 of a rectangle 212, the long sides 212 of which are parallel to centerline 216, and which delimits the contour 210 of the support member. In embodiments of the present invention contour 210 is the contour (254, see FIG. 7) of the foothold confined by the upper part (253, see FIG. 7) of the footwear (250, see FIG. 7), corresponding to the last which is used to form the footwear. In other embodiments of the present invention contour 210 is the outermost contour of the footwear. In other embodiments of the present invention contour 210 is the contour of the bottom surface of the sole of the footwear. In some embodiments, the terms "forward" and "anterior" are used interchangeably. In some embodiments, the terms "rearward" and "posterior" are used interchangeably. Each possibility represents a separate embodiment of the present invention.

According to embodiments of the present invention, as shown in FIG. 5, forward protuberance 218 at the anterior (phalanges) portion of the support member (i.e. its front portion) is positioned medially offset to centerline 216. By "medially offset" is meant that a peak surface (which can be the ground engaging surface) of protuberance 218 (marked by cross 219) is shifted from centerline 216 medially towards the inner side of support surface 200, facing the support member of the other foot (not shown in this figure). The peak surface is a surface on the protuberance which is furthest from the support surface with respect to other surfaces of the protuberance. Each possibility represents a separate embodiment of the present invention.

According to embodiments of the present invention, as shown in FIG. 5, rearward (posterior) protuberance 220 at the posterior (calcaneus) portion of the support member (i.e. its back portion) is positioned laterally offset to centerline 216. By "laterally offset" is meant that a peak surface (which can be the ground engaging surface) of protuberance 220 (marked by cross 221) is shifted from centerline 216 laterally towards the outer side of support surface 200, away from the support member of the other foot (not shown in this figure). Each possibility represents a separate embodiment of the present invention.

The alignment of the protuberances shown in FIG. 5 is useful, for example, for tuning muscles for users suffering from one or more of the following medical indications: medial compartment-knee osteoarthritis medial meniscus tear or damage, genu varus, patello-femoral pain syndrome, patello-femoral problem (malalignment), lateral collateral ligamental damage or tear, bone bruise MTP/MFC (or AVN in these), hip labrum damage (TCM), trochanteric bursitis, pes anseninus bursitis, ankle instability (supination and ext rut), Achilles tendonitis and metatrsalgia. Each possibility represents a separate embodiment of the present invention.

FIG. 6 is a simplified pictorial illustration of another alignment of the anterior and posterior protuberances on a support member, according to embodiments of the present invention. According to embodiments of the present invention, as shown in FIG. 6, forward (anterior) protuberance 218 is laterally offset to centerline 216, whereas rearward protuberance 220 is medially offset to centerline 216. The alignment of the protuberances shown in FIG. 5 is useful, for example, for tuning muscles for users with one or more of the following medical indications: lateral meniscus tear or damage, lateral compartment knee osteoarthritis, valgus knee (genu valgus), patello-femoral pain syndrome, patello-femoral problem (malalignment), MCL Ligament tear, bone bruise LTP/LFC (or AVN in these), hip labrum damage or tear, hip pain, hip OA, low back pain, ankle instability (pronation), achilles tendonitis, tibialis posterior insufficiency and metatarsalgia. Each possibility represents a separate embodiment of the present invention.

Figure 7:
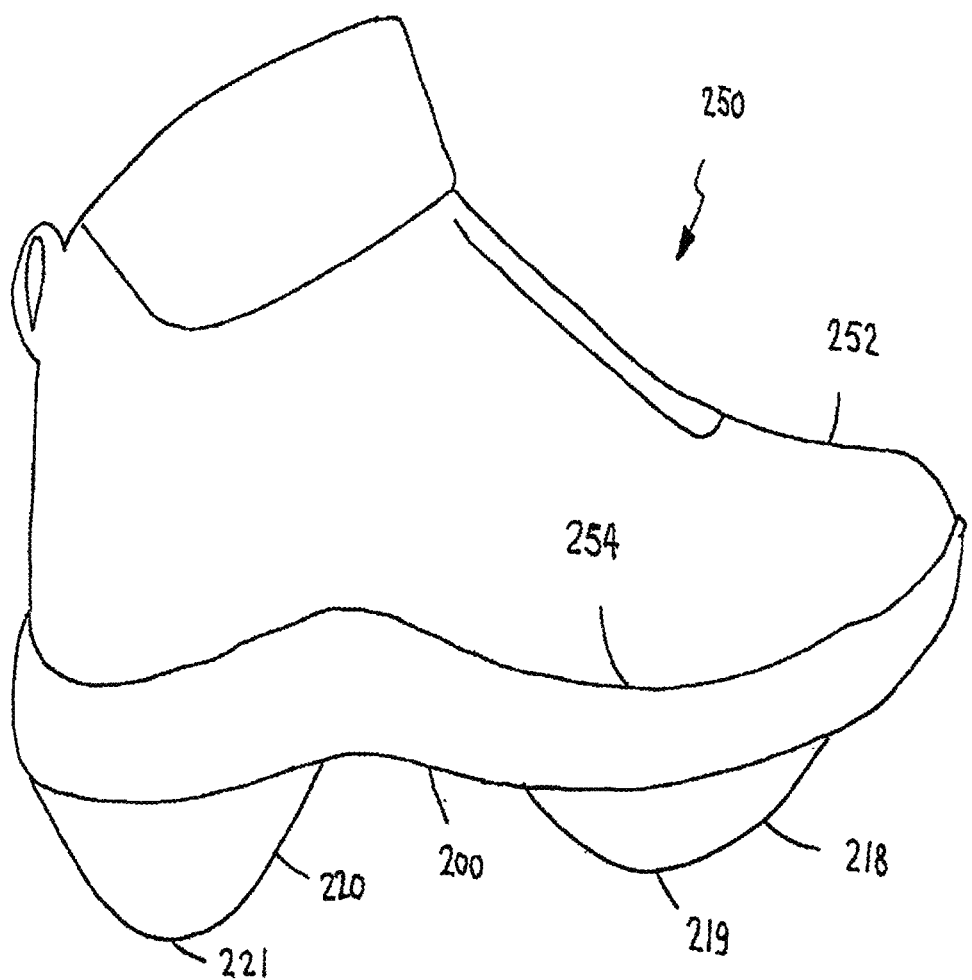
FIG. 7 is a simplified pictorial illustration of a sneaker constructed and operative in accordance with an embodiment of the present invention, whose rearward protuberance has a greater height than the height of the forward protuberance.

FIG. 7 is a simplified pictorial illustration of a sneaker 250 constructed and operative in accordance with an embodiment of the present invention, whose rearward protuberance 220 has a greater height than the height of the forward protuberance 218. It is noticeable that such arrangement facilitates initial contact between rearward protuberance 220 and the supporting ground (not shown in this figure) when a user wears the sneaker, before the forward protuberance is brought in contact with the ground. When both protuberances are placed in contact with the ground the foot of the user wearing sneaker 250 acquires a downward inclination with respect to direction of gait of the user. Each possibility represents a separate embodiment of the present invention.

Figure 8:
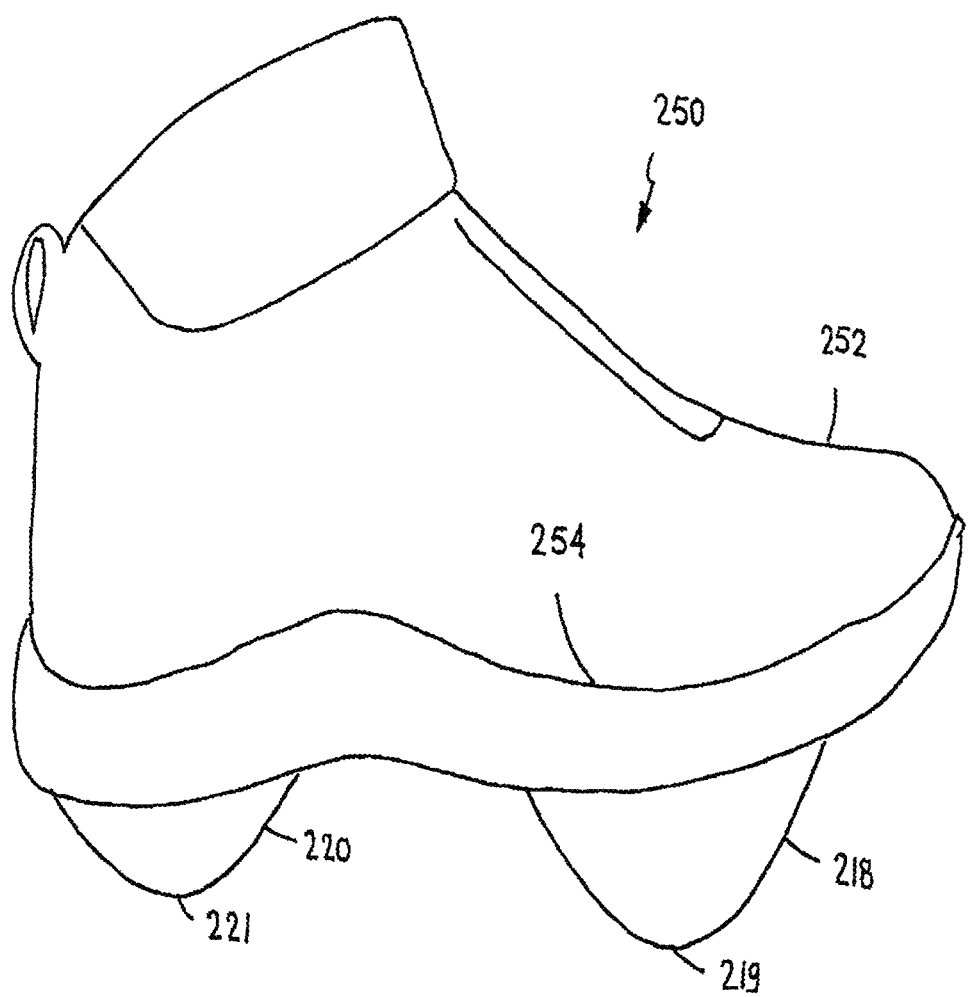
FIG. 8 is a simplified pictorial illustration of a sneaker constructed and operative in accordance with an embodiment of the present invention, whose forward protuberance has a greater height than the height of the rearward protuberance.

FIG. 8 is a simplified pictorial illustration of a sneaker 250 constructed and operative in accordance with an embodiment of the present invention, whose forward protuberance 218 has a greater height than the height of the rearward protuberance 220. In this embodiment when both protuberances are placed in contact with the ground the foot of the user wearing sneaker 250 acquires an upward inclination (with respect to the direction of gait of the user. Each possibility represents a separate embodiment of the present invention.

Figure 9:
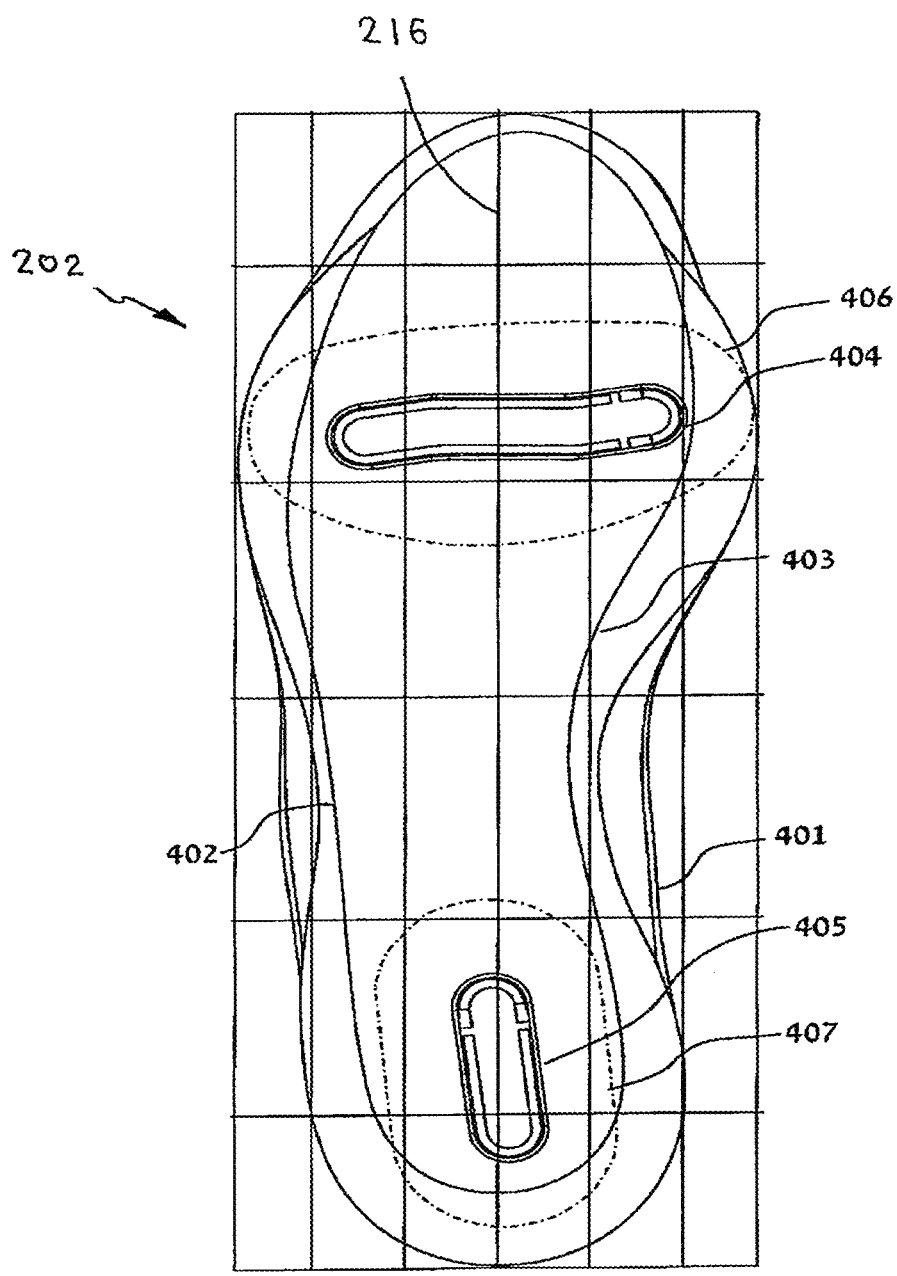
FIG. 9 illustrates maximal area boundaries of positioning of the anterior and posterior protuberances with respect to a support surface, according to embodiments of the present invention.

FIG. 9 illustrates maximal area boundaries of positioning of the anterior and posterior protuberances with respect to a support surface, according to embodiments of the present invention. Shown in this figure is a bottom view of a sneaker designed to be worn on a right foot of a user. The medial side is thus the right side of the drawing, facing the arc of greater curvature of the side arcs of the sneaker. The lateral side is opposite to the medial side that is the left side of the drawing, facing the arc of lesser curvature of the side arcs of the sneaker. Indicated are the midsole 401 and last/shoe 402, contour 403 of the foothold which is determined by the last used in the making of the sneaker. Front rail 404 and rear rail 405 are used for anchoring the protuberance. The area bordered by dotted line 406 marks the maximal area within which the peak surface of the anterior protuberance, i.e. the ground engaging surface of the anterior protuberance, may be located, according to some embodiments of the present invention. The area bordered by dotted line 407 marks the maximal area within which the peak surface of the posterior protuberance. Each possibility represents a separate embodiment of the present invention.

Figure 10:
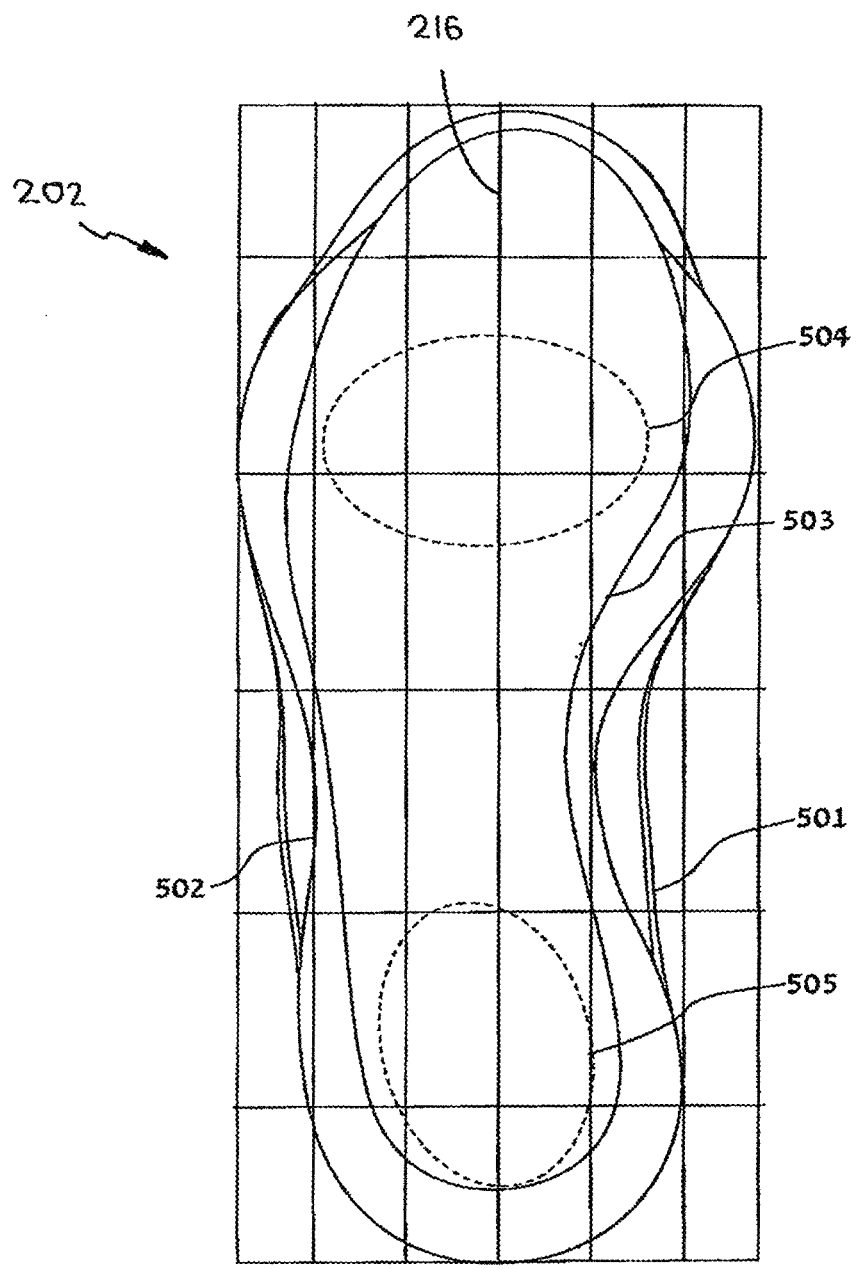
FIG. 10 illustrates effective area boundaries of positioning of the anterior and posterior protuberances with respect to a support surface, according to embodiments of the present invention.

FIG. 10 illustrates the effective area boundaries of positioning of the anterior and posterior protuberances with respect to a support surface, according to embodiments of the present invention. Indicated are the midsole 501 and outsole 502, contour 503 of the foothold which is determined by the last used in the making of the sneaker. The area bordered by dotted line 504 marks the effective area within which the peak surface of the anterior protuberance, i.e. the ground engaging surface of the anterior protuberance, may be located, according to some embodiments of the present invention. The area bordered by dotted line 505 marks the effective area within which the peak surface of the posterior protuberance. "Effective" refers to the effectiveness of use of the footwear according to embodiments of the present invention, which facilitates treatment. For clarity both FIGS. 9 and 10 are divided to 36 equal parts. The effective locations will be within the same parts regardless of sizing. Each possibility represents a separate embodiment of the present invention.

Figure 11:
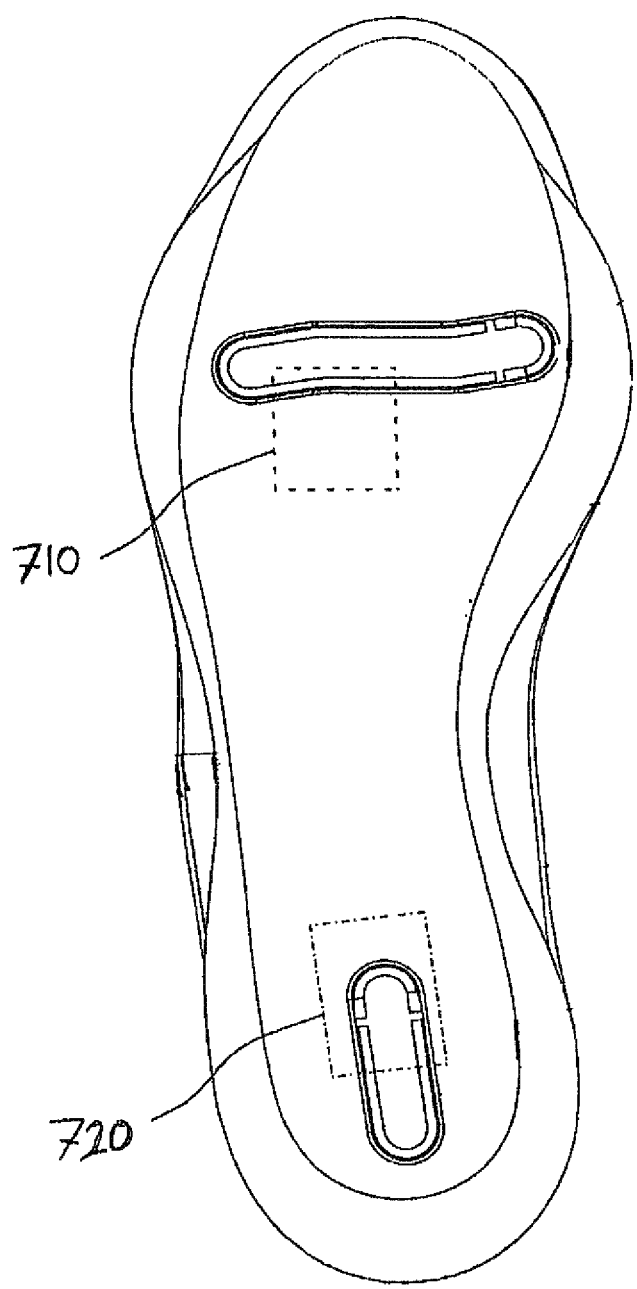
FIG. 11 illustrates effective area boundaries of positioning of the anterior and posterior protuberances with respect to a support surface, according to certain diseases of the present invention.

FIG. 11 illustrates the effective area boundaries of positioning of the anterior and posterior protuberances with respect to a support surface, according to embodiments of the present invention which include treatment and alleviating pain for the following diseases and/or conditions: Lateral meniscus tear/damage, Lateral compartment knee osteoarthritis, Valgus knee (genu valgus), Patello-femoral pain syndrome, Patello-femoral deficiency (mal-alignment), MCL Ligament tear, Bone bruise LTP/LFC (AVN), Hip labrum damage (tear), hip musculoskeletal pain, ankle instability (Pronation), Achilles tendonitis, Tibialis insufficiency, Metatarsalgia, or any combinations thereof. Indicated is the area bordered by dotted line 710 which marks the effective area within which the peak surface of the anterior protuberance, i.e. the ground engaging surface of the anterior protuberance, may be located, while treating or alleviating pain for the diseases and/or conditions described for FIG. 11 hereinabove. Indicated is the area bordered by dotted line 720 which marks the effective area within which the peak surface of the posterior protuberance, i.e. the ground engaging surface of the posterior protuberance, may be located, while treating or alleviating pain for the diseases and/or conditions described for FIG. 11 hereinabove. The areas bordered by dotted lines 710 and 720 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

FIG. 12 illustrates the effective area boundaries of positioning of the anterior and posterior protuberances with respect to a support surface, according to embodiments of the present invention which include tuning muscles and thus treating and alleviating pain in subjects suffering from: Medial Compartment knee OA, medial meniscus-tear/damage, Genu varus, Patello-femoral pain syndrome, Patello-femoral problem (malalignment), Lateral collateral ligamental (damage/tear), Bone bruise MTP/MFC (AVN), hip OA, Hip labrum damage (TCM), Trochanteric bursitis, Pes Anseninus bursitis, Ankle instability (supination ext rut), Achilles tendonitis, Metatrsalgia, or a combination thereof. Indicated are the midsole 601 and outsole 602, last 603 of the foothold which is determined by the last used in the making of the sneaker. Front rail 604 and rear rail 605 are used for anchoring the protuberance. Indicated is the area bordered by dotted line 610 which marks the effective area within which the peak surface of the anterior protuberance, i.e. the ground engaging surface of the anterior protuberance, may be located, while treating or alleviating pain for the diseases and/or conditions described for FIG. 12 hereinabove. Indicated is the area bordered by dotted line 620 which marks the effective area within which the peak surface of the posterior protuberance, i.e. the ground engaging surface of the posterior protuberance, may be located, while treating or alleviating pain for the diseases and/or conditions described for FIG. 12 hereinabove. The areas bordered by dotted lines 610 and 620 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

Figure 13A:
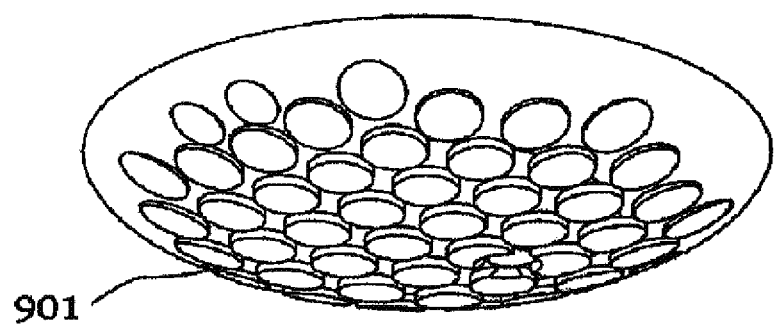
FIG. 13A is an isometric view of a protuberance suitable for use on a footwear, according to embodiments of the present invention.

FIG. 13A is an isometric view of a protuberance suitable for use on a footwear, according to embodiments of the present invention. Cleats 901, according to embodiments of the present invention, cover the ground engaging area of a protuberance, for facilitating enhanced grip of the surface on which the user stands or walks. FIG. 18B is a frontal view of a protuberance suitable for use on a footwear, according to embodiments of the present invention. The peak surface is marked by cross 902. Bore 904 is provided for a screw or other fastening arrangement to fix the protuberance in the desired position. FIG. 18C is a side view of a protuberance suitable for use on a footwear, according to embodiments of the present invention. Convexity 905 of the protuberance is clearly seen. Various convexities may be employed, all of which define a peak surface, typically (but not necessarily) at the center of the protuberance, which is the surface which comes in contact with the ground, when the user attaches the support member to the foot, and walks or stands on the ground.

Figure 13B:
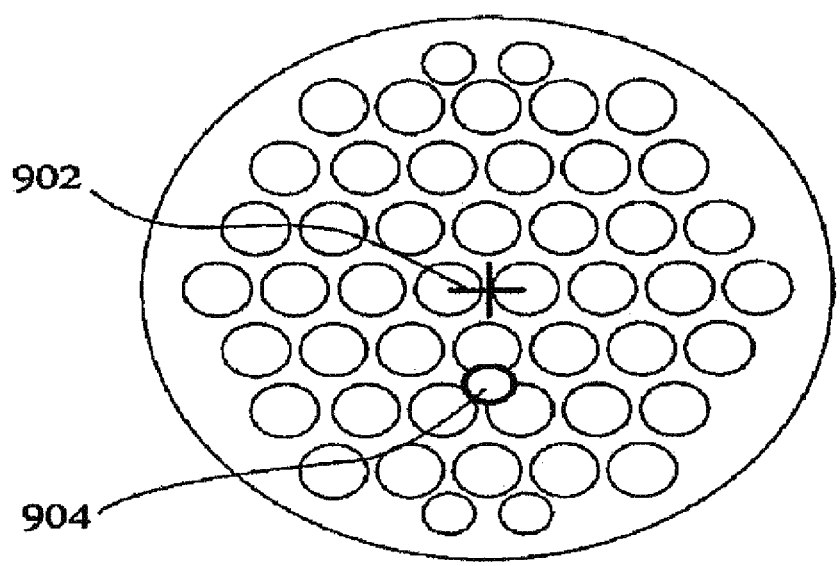
FIG. 13B is a frontal view of a protuberance suitable for use on a footwear, according to embodiments of the present invention.
Figure 13C:
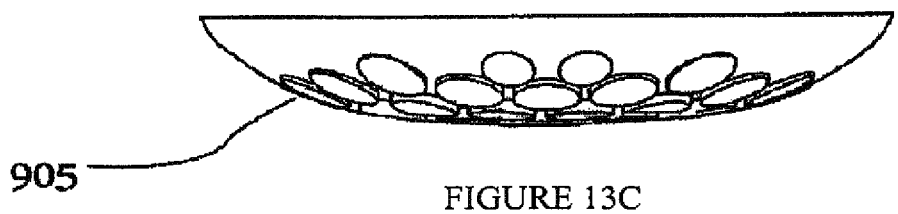
FIG. 13C is a side view of a protuberance suitable for use on a footwear, according to embodiments of the present invention.

FIG. 13 is a simplified pictorial illustration of a protuberance according to embodiments of the present invention. As shown a protuberance is convex 905 (13C). Each protuberance, according to embodiments of the present invention, comprises a fixing hole (for fixing a protuberance) 904 in which a latch, a bolt, or a screw is placed therein. The peak of a protuberance, which in some embodiments of the present invention, is placed within the center of the ground engaging area 902 is in contact with the ground during stance (13B). A grip structure 901.

Figure 14:
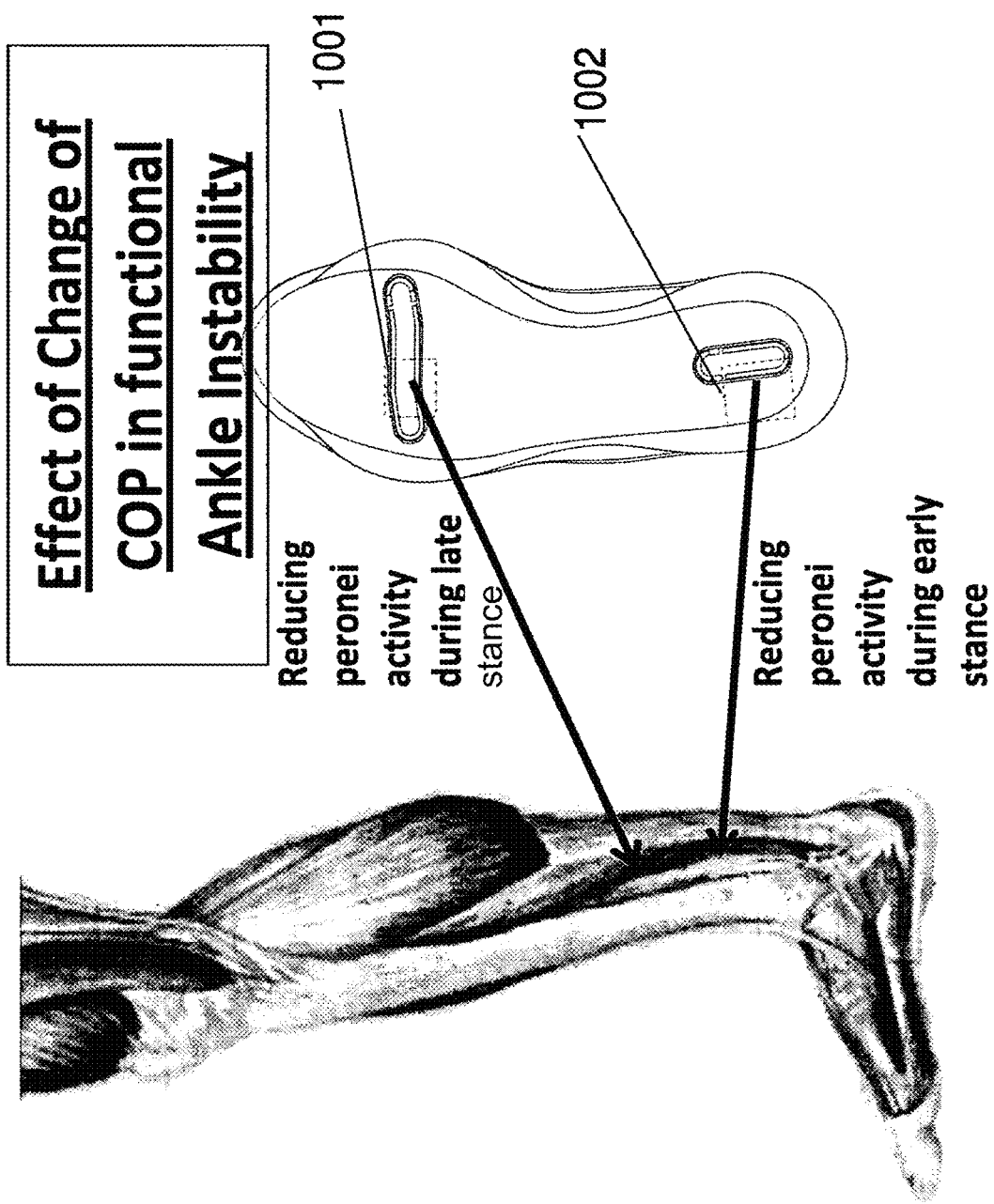
FIG. 14 illustrates effective area boundaries of positioning of the peaks of the ground engaging areas of the anterior (1001) and posterior (1002) protuberances with respect to a support surface, with respect to the differential tuning of muscles/induction of change in COP in functional ankle instability.

FIG. 14 illustrates the effective area boundaries of positioning of the anterior and posterior protuberances with respect to a support surface, according to embodiments of the present invention which include tuning muscles and thus treating and alleviating pain in subjects suffering from ankle instability. Indicated is the area bordered by dotted line 1001 which marks the effective area within which the peak surface of the anterior protuberance, i.e. the ground engaging surface of the anterior protuberance, may be located. Indicated is the area bordered by dotted line 1002 which marks the effective area within which the peak surface of the posterior protuberance, i.e. the ground engaging surface of the posterior protuberance, may be located. Each possibility represents a separate embodiment of the present invention.

Figure 15:
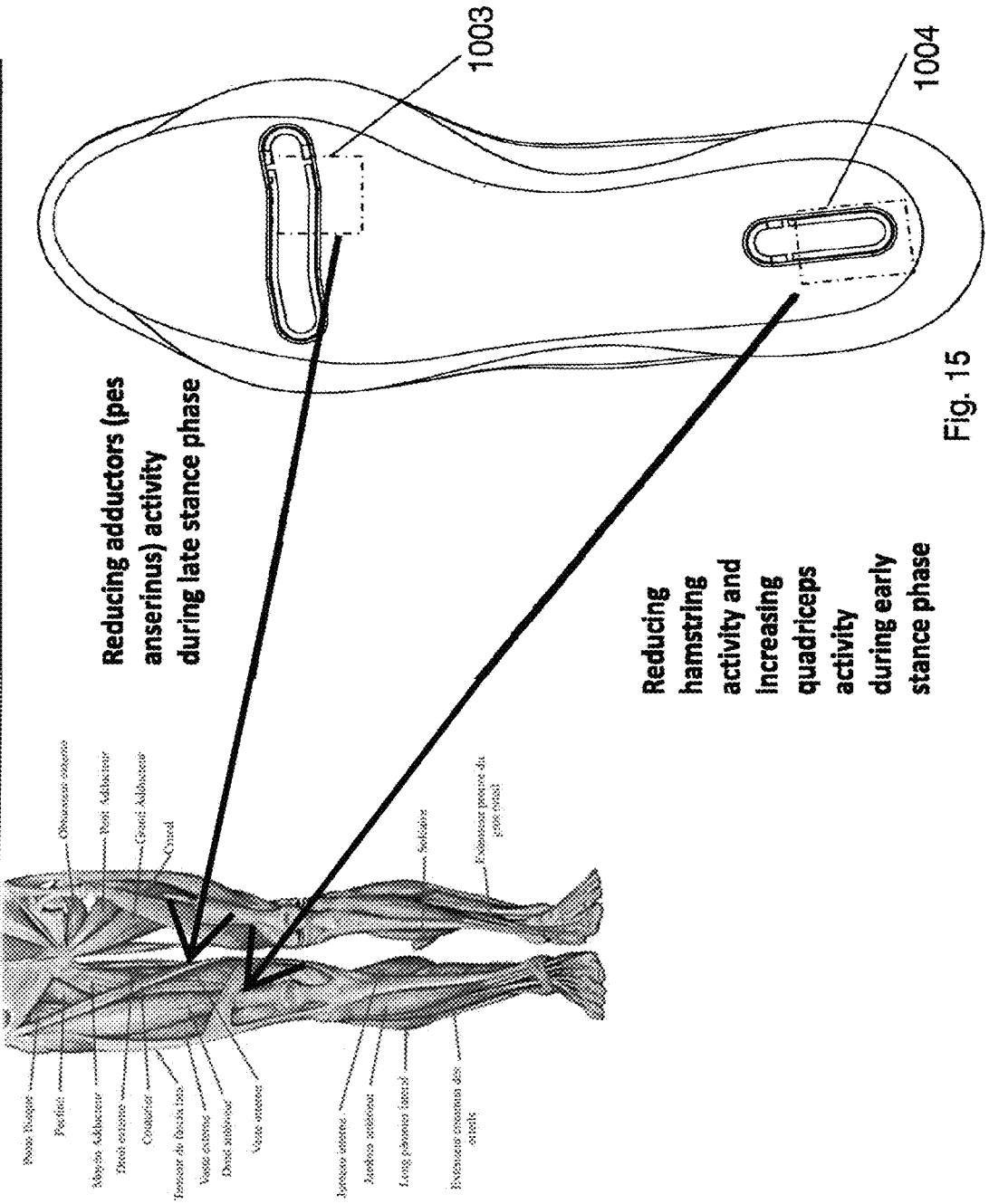
FIG. 15 illustrates effective area boundaries of positioning of the peaks of the ground engaging areas of the anterior (1003) and posterior (1004) protuberances with respect to a support surface, with respect to the differential tuning of muscles/induction of change in COP in medial knee osteoarthritis.

FIG. 15 illustrates the effective area boundaries of positioning of the anterior and posterior protuberances with respect to a support surface, according to embodiments of the present invention which include tuning muscles and thus treating and alleviating pain in subjects suffering from knee OA. Indicated is the area bordered by dotted line 1003 which marks the effective area within which the peak surface of the anterior protuberance, i.e. the ground engaging surface of the anterior protuberance, may be located. Indicated is the area bordered by dotted line 1004 which marks the effective area within which the peak surface of the posterior protuberance, i.e. the ground engaging surface of the posterior protuberance, may be located. Each possibility represents a separate embodiment of the present invention.

Resilience, Hardness, and Elasticity

In another embodiment, calibrating comprises positioning a protuberance on a support member. In another embodiment, calibrating comprises adjusting the height or protrusion of a protuberance. In another embodiment, calibrating comprises adjusting a resilience of a protuberance. In another embodiment, calibrating comprises adjusting a hardness of a protuberance. In another embodiment, calibrating comprises adjusting an elasticity of a protuberance. Each possibility represents a separate embodiment of the present invention.

In another embodiment, a protuberance is compressible. In another embodiment, a protuberance is deformable. In another embodiment, a protuberance is compressible or deformable upon pressure exerted by subject's weight. Each possibility represents a separate embodiment of the present invention.

In another embodiment, a protuberances is constructed of any suitable material, such as but not limited to, elastomers or metal or a combination of materials, and have different properties. In another embodiment, a protuberance comprises different resilience or hardness, such as having different elasticity properties or Shore hardness. Each possibility represents a separate embodiment of the present invention.

In another embodiment, a protuberance comprises spikes or grip means for providing better stability. In another embodiment, a protuberance comprises spikes or grip means as anti-slippery means. In another embodiment, FIG. 13 provides a protuberance comprising small rounded grip means. In another embodiment, spikes or grip means are constructed of any suitable material, such as but not limited to: elastomers such as rubbers or plastic materials. In another embodiment, spikes or grip means cover only a portion of a protuberance. In another embodiment, spikes or grip means cover at least a ground engaging surface of a protuberance (the surface in contact with the ground during stance). In another embodiment, a fixing means for securing a protuberance to the support portion is embedded within a spikes or a grip means. In another embodiment, a fixing means for securing a protuberance to the support portion is places in between spikes or a grip means. Each possibility represents a separate embodiment of the present invention.

In another embodiment, a protuberance has a shore hardness of between 30 to 90 Sh A. In another embodiment, a protuberance has a shore hardness of between 40 to 55 Sh A. In another embodiment, a protuberance has a shore hardness of between 50 to 70 Sh A. In another embodiment, a protuberance has a shore hardness of between 65 to 90 Sh A. In another embodiment, a protuberance has a shore hardness of between 55 to 60 Sh A. In another embodiment, a protuberance has a shore hardness of between 65 to 70 Sh A. In another embodiment, an anterior and a posterior protuberance comprise identical shore hardness. In another embodiment, an anterior and a posterior protuberance comprise different shore hardness. Each possibility represents a separate embodiment of the present invention.

In another embodiment, a protuberance is a soft protuberance comprising a shore hardness of between 40 to 55 Sh A. In another embodiment, a protuberance is a medium hardness protuberance comprising a shore hardness of between 50 to 70 Sh A. In another embodiment, a protuberance is a hard protuberance comprising a shore hardness of between 65 to 90 Sh A.

In another embodiment, a protuberance has an abrasion between 1-60 mm$^3$ (by DIN 53516). In another embodiment, a protuberance comprises a rubber cup. In another embodiment, a protuberance comprises natural rubber compounds. In another embodiment, a protuberance comprises synthetic rubber compounds such as TPU or TPR. In another embodiment, a protuberance comprises silicone. In another embodiment, a protuberance a plastic material such as PA 6 (nylon), PA6/6 (nylon)+glass fiber, ABS, Polypropylene, POM (Polyoxymethylene). In another embodiment, a protuberance comprises a metal such as aluminum, steel, stainless steel, brass, or metal alloys. In another embodiment, a protuberance comprises compound materials such as glass fibers, carbon fibers, kevlar, or any combination thereof. Each possibility represents a separate embodiment of the present invention.

Adjustments

In another embodiment, different heights of a protuberance can be used. In another embodiment, height is calibrated by adding a spacer between a protuberance and the outsole. In another embodiment, different weights of a protuberance can be used. In another embodiment, weight is calibrated by adding a spacer between a protuberance and the outsole.

In another embodiment, the height of the anterior protuberance differs from the height of the posterior protuberance. In another embodiment, the height of the anterior protuberance or of the posterior protuberance is adjusted with round spacers positioned between the support member or the outsole and the base portion of a protuberance. In another embodiment, a spacer is fixed between the outsole and base portion of a protuberance. Each possibility represents a separate embodiment of the present invention.

In another embodiment, a spacer or a protuberance comprises a diameter of 50-150 mm. In another embodiment, a spacer or a protuberance comprises a diameter of 55-110 mm. In another embodiment, a spacer or a protuberance comprises a diameter of 60-100 mm. In another embodiment, a spacer or a protuberance comprises a diameter of 80-90 mm. In another embodiment, a spacer or a protuberance comprises a diameter of 85 mm. In another embodiment, a spacer or a protuberance or a protuberance comprises a thickness of 1-12 mm. In another embodiment, a spacer or a protuberance comprises a thickness of 1-4 mm. In another embodiment, a spacer or a protuberance comprises a thickness of 3-10 mm. In another embodiment, a spacer or a protuberance comprises a thickness of 1-3 mm. In another embodiment, a spacer or a protuberance comprises hardness of 60-70 Shore A, which is a soft spacer. In another embodiment, a spacer or a protuberance comprises hardness of 90-100 Shore A, which is a hard spacer. In another embodiment, a spacer or a protuberance comprises hardness of 71-890 Shore A, which is medium hardness spacer.

In another embodiment, a spacer or a protuberance weighs 2-500 g. In another embodiment, a spacer or a protuberance weighs 2-250 g. In another embodiment, a spacer or a protuberance weighs 2-6 g. In another embodiment, a spacer or a protuberance weighs 2-20 g. In another embodiment, a spacer or a protuberance weighs 2-20 g is made of Nylon. In another embodiment, a spacer or a protuberance weighs 2-20 g is made of Nylon and fiber. In another embodiment, a spacer or a protuberance weighs 2-40 g is made of Nylon and glass fiber. In another embodiment, a spacer or a protuberance weighs 30-100 g. In another embodiment, a spacer or a protuberance weighs 50-80 g. In another embodiment, a spacer or a protuberance weighs 60-100 g. In another embodiment, a spacer or a protuberance comprises: Nylon glass fiber polyurethane an alloy (such as but not limited to Zink alloy), or any combination thereof. Each possibility represents a separate embodiment of the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Pain Scale

In all case studies pain is presented as graded by the patient on a 10 cm Visual analogue scale. A pain of 4/10 means 4 cm out of 10 cm (where "0" is no pain and "10" is the worst pain).

Positioning Method

After each change (calibration, positioning) in configuration in the protuberances attached to the footwear, the patient was asked to walk a distance of 10 meters away from the therapist and then back in order to verify that the patient remains balanced and that the change in configuration resulted in a desired positive effect (i.e. reduction in pain, improvement of timing of the heel-strike etc').

Prescribing the Device

The device comprises 2 units of footwear: one for the left foot and one to the right foot. The footwear used is a light walking boot.

Prescription included a set of instructions to the patients. These instructions included: the length of wear the device per day (usually 30-60 minutes daily). Daily use included Wearing the device during routine activities that may include watching TV, computer activities; eating activities, etc. Actual walking constituted 10-25% of 30-60 minutes. Thus, if patient worn the device for 60 minutes per day, total of 5-10 minutes were dedicated, accumulatively, to walking.

Example 1: Muscle Tuning in Functional Ankle Instability (FAI) (Chronic Ankle Instability)

A 23 years old male patient was presented to the treatment center with a longstanding complaint of repetitive sprains of both ankles.

Case History: The patient reported that he first sprained his left ankle at the age of 12. Shortly thereafter he sprained his right ankle. He reported that the frequency of ankle sprains increased since and at the time of the first assessment he was avoiding any uneven terrain. He avoided any sporting activities unless he used ankle braces (Aircast) bilaterally. He had pain on the lateral aspect of both ankles during outdoor walking whenever he walked for a distance greater than 1.5 kilometres (VAS left-3/10, right-4/10). He also reported fatigue on the lateral aspect of both calves and a mild burning sensation along the tendons of the peronei bilaterally after prolonged walking.

Physical Examination: On observation there was mild swelling on the anterior aspect of the right and the left malleoli. Both feet were in a mildly hypersupinated alignment. One leg stand was 5 sec. on the right and 8 sec. on the left. Romberg test showed increased postural sway with the eyes closed. Ankle ranges of motion were full bilaterally. Combined inversion and plantar flexion produced pain along the anterior talo-fibular ligament (ATFL). Anterior drawer tests for the ankle were negative bilaterally. Clinical gait assessment revealed hypersupination and an early heel rise in the right and the left legs.

Imaging and Gaitlab: Talar tilt X-rays were negative for mechanical instability (right-4 degrees, left-4 degrees). Anterior drawer X-rays were negative for anterior instability (right-3 mm, left-2 mm). There was no evidence of joint damage on X-ray. Gaitlab parameters were: velocity 123.0 cm/sec., left step length-64.8 cm., right step length-65.3 cm., left single limb support-37.2%, right single limb support-37.5%.

Therapy: bulbous protuberances (B.P.s) with C convexity and "soft" resilience (hardness) were connected and fixed under the hind-foot and fore-foot of the left and right footwear. A 100 gr. weighted spacer (disc) of 2.5 mm height was attached and fixed between the right and left shoes and the posterior right and left B.P.s.

Balancing: The patients system was calibrated and fine tuned during repeated clinical gait assessments with the footwear. During this process care is taken to reduce the eversion and inversion during heel strike, loading response, mid-stance and toe-off.

Rationale: Maintain plantar flexion through disc due to early heel rise bilaterally in barefoot gait. Since the peronei brace in FAI leading to an increased angular velocity toward inversion at heel strike and a concentric eversion moment during stance their activity needs to be supported. Therefore a lateral calibration of posterior B.P.s. is beneficial. This also ensured prevention of respraining the ankle while wearing the system.

Since it was apparent that the invertors had a weaker eccentric power generation in FAI, strengthening in an eccentric manner was required. This is also achieved by lateral calibration of posterior B.P.s.

Pain: The patient did not complain of pain.

Heel-Rise Timing: The patient was asked to walk 20 m in order to confirm that he is still balanced and the heel-rise is well timed in the gait cycle. It was observed that the early-heel rise seen in barefoot gait was corrected.

Treatment Plan: The patient was briefed about the safety instructions of the therapy and was asked to wear the system at home for 45 minutes a day on each day of the first week of the treatment. During this time he was instructed to be seated for most (80%) of the time, getting up occasionally to do daily activities such as answering the phone or getting a drink. Accumulative weight bearing time per day in the first week was 7 to 9 minutes (20% of total time with the system). The patient was instructed to increase the total wearing time by 15 minutes per week maintaining an accumulative 20% of weight bearing time with the footwear. The patient was seen for follow-up consultations at the center 4 weeks after his first visit, 10 weeks after his first visit, and 5 months after his first visit.

Treatment Progression: In the first follow up consultation the patient reported that he felt more comfortable performing indoors daily activities with the system than with his regular shoes. Gaitlab data is provided in table number 1. He was then asked to increase the total wearing time of the system by 15 minutes per week and maintain the 20% accumulative weight bearing time. In the second follow up consultation the patient has reached a total weight bearing time of 3 hours. He reported that he has ceased to feel unstable when walking outside for over 1.5 hours and the burning pain he felt on the lateral aspect of his ankles was gone. Gait lab data (provided in table number 1) shows increases in gait velocity, right and left step lengths. The data also shows an increase in right and left single limb support. His system was therefore calibrated so that the convexity of the anterior and the posterior right and left B.P.s was increased to D level of convexity. The patient was instructed to add to the current total weight bearing time 10 minutes of outdoor walking. He was asked to increase the outdoor walking by 5 minutes each week to a limit of 30 minutes. In the third follow up consultation the patient reported that he went on a hike and did not require the support of the ankle brace. The posterior B.P.s were therefore calibrated to a position 3 mm more medial to the former position. This increased the activity of the ankle evertor muscles and further tuned the timing of their contraction.

TABLE 1

Patient Gaitlab Data

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1st (initial) | 123.0 | 64.8 | 65.3 | 37.2 | 37.5 |
| 2nd (first follow-up) | 125.2 | 65.4 | 65.6 | 37.6 | 38.0 |
| 3rd (second follow-up) | 137.3 | 68.2 | 68.1 | 38.8 | 39.0 |

Example 2: Prevention Program to Prevent an ACL Tear in an Athlete

A 20 years old female professional basketball player was presented to the treatment canter. The patient was a professional basketball player performing 10 basketball practices a week. at the time of the assessment she was had no physical complaints. The team physiotherapist had noticed that when she lands from a jump and changes direction during running, her knees fall into a significant valgus alignment. It is known that such lack of movement control, specifically in female athletes, significantly increases the risk for ACL tear.

Physical Examination: On observation the patient had hyperpronating feet and both the right and the left knees were in a valgus alignment (estimated as 15 degrees). Muscle mass appeared good and there were no apparent asymmetries. Knee and ankle joint stability tests were all negative (Knee: anterior drawer test, valgus stress test, varus stress test, Lachman's test. Ankle: anterior drawer test). Clinical gait assessment did not reveal any significant findings except for the valgus in the knees. Drop vertical jump (stair hop) test was positive. Beighton's scale was positive for hyper mobility.

Imaging and Gaitlab Data: There was no imaging available. Gaitlab parameters were: velocity 120.8 cm/sec., left step length-63.8 cm., right step length-61.9 cm., left single limb support-43.1%, right single limb support-42.8%.

Therapy: B.P.s with C convexity and "hard" resilience were connected and fixed under the hind-foot and fore-foot of the left and right footwear. A 100 gr. weighted spacer (disc) of 2.5 mm height was attached and fixed between the right and left shoes and the posterior right and left B.P.s.

Balancing: The patients system was calibrated and fine tuned during repeated clinical gait assessments with the footwear. During this process care is taken to reduce the eversion and inversion during heel strike, loading response, mid-stance and toe-off.

Rationale: Tuning of the timing of various muscles (specifically the hip abductors and hip external rotators) can improve the control over the proximal part of the knee (the femur) and thus prevent excessive valgus of the in various activities. The posterior B.P. of the right and left system is therefore calibrated and fixed 6 mm. medial to the neutral position.

Increasing the activity of the quadriceps muscle will ensure greater shock absorption by the muscle, thus decreasing the load on the knee. The posterior B.P. of both the right and the left systems is therefore calibrated and fixed 10 mm. posterior to the neutral position.

Balancing: The patients system was calibrated and fine tuned during repeated clinical gait assessments with the footwear. During this process care is taken to reduce the eversion and inversion during heel strike, loading response, mid-stance and toe-off.

Pain: The patient did not complain of pain.

Heel-Rise Timing: The patient was asked to walk 20 m in order to confirm that he is still balanced and the heel-rise is well timed in the gait cycle. No abnormalities in heel-rise timing were observed.

Treatment Plan: The patient was briefed about the safety instructions of therapy and was asked to wear the system at home for 45 minutes a day on each day of the first week of the treatment. During this time she was instructed to be seated for most (80%) of the time, getting up occasionally to do daily activities such as answering the phone or getting a drink. Accumulative weight bearing time per day in the first week was 7 to 9 minutes (20% of total time with the system). The patient was instructed to increase the total wearing time by 15 minutes per week maintaining an accumulative 20% of weight bearing time with the footwear. The patient was seen for follow-up consultations at the center 3 weeks after her first visit, 6 weeks after her first visit, and 12 months after his first visit.

Treatment Progression: In the first follow up consultation the patient reported that she felt comfortable performing indoors daily activities with the system. Gaitlab data is provided in table number 1. She was then instructed to perform squats with the system (10 repetitions per set, 4 sets per day), and lunges with the system (10 repetitions for each leg per set, 4 sets for each leg per day). She was also asked to increase the total wearing time of the system by 15 minutes a week, maintaining 20% of accumulative weight bearing time. On the second follow up consultation she has reached a total wearing time of 3 hours and reported that performing the squats and the lunges was easy. Drop vertical jump (stair hop) test was performed with less valgus at the knees. The convexity of the anterior and posterior B.P. of the left and right systems was changed to D level of convexity. She was instructed to continue with the squat and lunge exercise and add practicing jump shots, dribbling and other basketball drills.

On the third follow up the drop vertical jump (stair hop) test was negative.

TABLE 2

Patient Gaitlab Data

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 120.8 | 63.8 | 61.9 | 43.1 | 42.8 |
| $2^{nd}$ (first follow-up) | 125.2 | 64.1 | 63.4 | 42.2 | 42.6 |
| $3^{rd}$ (second follow-up) | 132.4 | 67.9 | 66.5 | 41.5 | 42.2 |

The invention claimed is:

1. A device comprising a foot securing means, a support member operably attached to said securing means; an outsole; an anterior protuberance and a posterior protuberance; said posterior protuberance, said anterior protuberance, or both said anterior protuberance and said posterior protuberance, are prepositioned and fixed to a position distanced from a balanced position, said distanced is selected from the group consisting of: (a) 1 mm to 10 mm laterally, (b) 1 mm to 10 mm anteriorly, (c) 1 mm to 10 mm medially, (d) 1 mm to 10 mm posteriorly, (e) 1 mm to 10 mm anteriorly and medially, (f) 1 mm to 10 mm anteriorly and laterally, (g) 1 mm to 10 mm posteriorly and medially, or (h) 1 mm to 10 mm posteriorly and laterally, said balanced position comprises a position: wherein said device is adapted to exert a reduced inversion or a reduced eversion during stance phases to a user's foot, wherein anterior protuberance's peak and posterior protuberance's peak are positioned on opposite sides of a centerline of said support member.

2. The device of claim 1, wherein said posterior protuberance is a bulbous protuberance, said anterior protuberance is a bulbous protuberance, or both said posterior protuberance and said anterior protuberance are bulbous protuberances.

3. The device of claim 1, wherein said anterior protuberance is shaped differently from the outer contour of said posterior protuberance.

4. The device of claim 1, wherein said anterior protuberance is a moveable anterior protuberance, said posterior protuberance is a moveable posterior protuberance, or both said posterior protuberance and said anterior protuberance are moveable.

5. The device of claim 4, wherein said (a) moveable anterior protuberance, (b) said moveable posterior protuberance, or (a) and (b) are moveable along an outer surface of said outsole within an area of 1 $cm^2$ to 18 $cm^2$.

6. The device of claim 4, wherein said posterior protuberance is movable within a calcaneus support portion of said support member.

7. The device of claim 4, wherein said anterior protuberance is movable within phalanges or metatarsals support portion of said support member.

8. The device of claim 1, wherein said anterior protuberance, said posterior protuberance, or both said posterior protuberance and said anterior protuberance, comprise a cross-section with a shape of a conic section, said conic section comprising at least one of a circle, ellipse, parabola and hyperbola.

* * * * *